US005401624A

United States Patent [19]

Sato et al.

[11] Patent Number: 5,401,624

[45] Date of Patent: Mar. 28, 1995

[54] DYE FORMING COUPLERS AND SILVER HALIDE COLOR PHOTOSENSITIVE MATERIAL CONTAINING THE SAME

[75] Inventors: Kozo Sato; Yoshio Ishii; Katsuyoshi Yamakawa, all of Kanagawa, Japan

[73] Assignee: Fuji Photo Film Co., Ltd., Kanagawa, Japan

[21] Appl. No.: 145,630

[22] Filed: Nov. 4, 1993

Related U.S. Application Data

[60] Division of Ser. No. 14,419, Feb. 5, 1993, which is a continuation-in-part of Ser. No. 798,114, Nov. 26, 1991, abandoned.

[30] Foreign Application Priority Data

Nov. 30, 1990 [JP] Japan .................................. 2-336807
Feb. 19, 1992 [JP] Japan .................................. 4-69854

[51] Int. Cl.[6] ............................................ G03C 7/38
[52] U.S. Cl. .................................... 430/558; 430/384; 430/385
[58] Field of Search ........................ 430/558, 384, 385

[56] References Cited

U.S. PATENT DOCUMENTS 4,950,585 8/1988 Tachibana et al. ................. 430/385
5,187,057 2/1993 Ikosu et al. ......................... 430/558
5,208,141 5/1993 Ikesu et al. .......................... 430/558

FOREIGN PATENT DOCUMENTS 2-304438 12/1990 Japan ................................... 430/558

OTHER PUBLICATIONS

*Patent Abstract of Japan*, vol. 16, No. 540 (P-1450), Nov. 10, 1992.

*Primary Examiner*—Lee C. Wright
*Attorney, Agent, or Firm*—Sughrue, Mion, Zinn, Macpeak & Seas

[57] ABSTRACT

A silver halide color photosensitive material which forms a cyan dye that has superior heat resistance and that will not readily fade in a reducing atmosphere. The silver halide color photosensitive material contains in at least one layer on a support at least one coupler represented by formula (I):

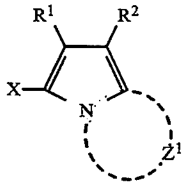

(I)

wherein $R^1$ represents hydrogen atom or a substituent; $R^2$ represents a substituent; X represents hydrogen atom or a group releasable on a coupling reaction with an oxidation product of a color developing agent; $Z^1$ represents a nonmetallic atom group necessary for forming a nitrogen-containing, six-membered, heterocyclic ring which has at least one dissociative group: $Z^1$ cannot be —C(=O)—N(R)—C(=O)—NH—; and R represents a substituent.

Also disclosed is a novel dye forming coupler which exhibits a high coupling activity and which gives a dye having a large molar extinction coefficient and superior stability, the coupler being represented by the following formula (XX) or (XXI). Also disclosed is a silver halide color photosensitive material which contains at least one of the dye forming couplers of formulae (XX) and (XXI) and which provides sharp dye images with high fastness properties.

(XX)

(Abstract continued on next page.)

ABSTRACT
-continued
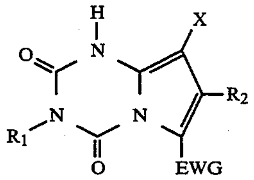
(XXI)
-continued
wherein EWG represents an electron withdrawing group having a Hammett's $\sigma_p$ value of not less than 0.3; $R_1$ and $R_2$ each represent a substituent; and X represents hydrogen atom or a group releasable on a coupling reaction with an oxidation product of an aromatic primary amine developing agent.
10 Claims, 1 Drawing Sheet

DYE FORMING COUPLERS AND SILVER HALIDE COLOR PHOTOSENSITIVE MATERIAL CONTAINING THE SAME

This is a divisional of application Ser. No. 08/014,419, filed Feb. 5, 1993, which is a continuation-in-part of application Ser. No. 07/798,114, now abandoned, which was filed Nov. 26, 1991.

BACKGROUND OF THE INVENTION

The present invention relates to novel dye forming couplers for use, for example, in silver halide color photosensitive materials and to a silver halide color photosensitive material containing the same.

One type of silver halide color photosensitive material in which a color image is formed by making use of a reaction of a color developing agent with dye forming couplers which develop yellow, magenta and cyan is now most widely put into practical use.

In recent years, studies have been actively conducted to improve dye forming couplers for silver halide color photosensitive materials in terms of color reproducibility and stability of dye image. However, no satisfactory improvement has yet been made, due to, for example, limitations relating to the color development agent. Particularly, for cyan couplers, phenol cyan couplers or naphthol cyan couplers have heretofore continuously been employed, but dyes which are formed from these cyan couplers have undesired absorption in the blue and green regions, which is a serious obstacle to an improvement in color reproducibility. In addition, it is disadvantageous to the improvement in sharpness of the resulting images that the cyan dyes that are formed from the conventional cyan couplers have a small molar extinction coefficient.

Recently, cyan dye forming couplers with a novel skeleton having a nitrogen-containing heterocyclic ring have been actively studied, and various heterocyclic compounds have been proposed: for example, a diphenylimidazole coupler disclosed in Japanese Patent Application Laid-Open (KOKAI) No. 63-226653 (1988), and pyrazoloazole couplers disclosed in Japanese Patent Application Laid-Open (KOKAI) Nos. 63-199352 (1988), 63-250649 (1988), 63-250650 (1988), 64-554 (1989), 64-555 (1989), 1-105250 (1989), 1-105251 (1989), etc. These couplers are expressly improved in color reproducibility and are characterized by excellent absorption characteristics of the dyes formed therefrom.

The above-described conventional couplers suffer, however, from the disadvantages that the cyan dyes that are formed therefrom have absorption in the shorter wavelength region and are inferior in stability to light and heat, and further involve the serious problem in practical application that the coupling activities of the couplers themselves are low.

Dark fading of cyan dyes obtained from the above in a reducing atmosphere is reported, for example, in the Journal of NSG (Japan Society of Photography) No. 50,183 (1987).

OBJECTS OF THE INVENTION

A first object of the present invention is to provide a silver halide color Photosensitive material containing a novel cyan coupler and capable of forming a cyan dye having a high color density and excellent spectral extinction characteristics.

A second object of the present invention is to provide a silver halide color photosensitive material capable of forming cyan dye images which are superior in heat resistance and which will not readily fade in a reducing atmosphere.

A third object of the present invention is to provide a novel coupler which exhibits a high coupling activity and which gives a dye having a large molar extinction coefficient.

A fourth object of the present invention is to provide a novel coupler which gives a dye having excellent stability.

A fifth object of the present invention is to provide a silver halide color photosensitive material containing an improved coupler which has solved the above-described problems of the conventional couplers so as to provide sharp dye images with high fastness properties.

SUMMARY OF THE INVENTION

In one aspect of the present invention, the present invention provides a silver halide color photosensitive material comprising a support having thereon at least one hydrophilic colloidal layer containing at least one dye forming coupler represented by formula (I):

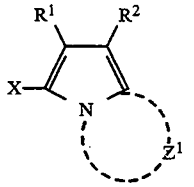

(I)

wherein $R^1$ represents hydrogen atom or a substituent; $R^2$ represents a substituent; X represents hydrogen atom or a group releasable on a coupling reaction with an oxidation product of a color developing agent; $Z^1$ represents a nonmetallic atom group necessary for forming a nitrogen-containing, six-membered, heterocyclic ring which has at least one dissociative group: $Z^1$ cannot be —C(=O)—N(R)—C(=O)—NH—; and R represents a substituent.

Cyan dye images obtained from the coupler of formula (I) of the present invention are superior in both resistance to light and stability to heat. The silver halide color photosensitive material of the present invention, which contains the novel coupler of formula (I), provides dye images that are stable to light, heat and moisture and exhibit a high dye forming speed and a high maximum color density in a color developer. The dye forming speed and the maximum color density are satisfactorily high even in a color developer with benzyl alcohol removed therefrom. In addition, the silver halide color photosensitive material of the present invention makes it possible to attain a silver halide color photosensitive material processing method wherein there is substantially no lowering in the density when the photosensitive material is processed with a processing solution having a bleaching agent of weak oxidizing power (e.g., a processing solution having a bleaching agent containing EDTA iron (III) Na salt or EDTA iron (III) $NH_4$ salt) or a processing solution having bleaching power which has become exhausted.

In another aspect of the present invention, the present invention provides a dye forming coupler represented by formula (XX) or (XXI):

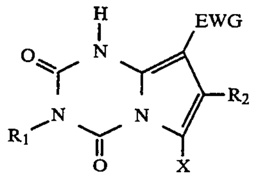

(XX)

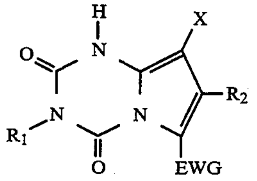

(XXI)

wherein EWG represents an electron withdrawing group having a Hammett's $\sigma_p$ value of not less than 0.3; $R_1$ and $R_2$ each represent a substituent; and X represents a hydrogen atom or a group releasable on a coupling reaction with an oxidation product of an aromatic primary amine developing agent.

In addition, the present invention provides a silver halide color photosensitive material which contains at least one of the dye forming couplers of formulae (XX) and (XXI).

The dye forming coupler of formula (XX) or (XXI) of the present invention has a high coupling activity and gives a dye which has a large molar extinction coefficient and which is superior in stability. The photosensitive material of the present invention, which contains the dye forming coupler of formula (XX) or (XXI), provides sharp dye images with high fastness properties.

Figure 1:
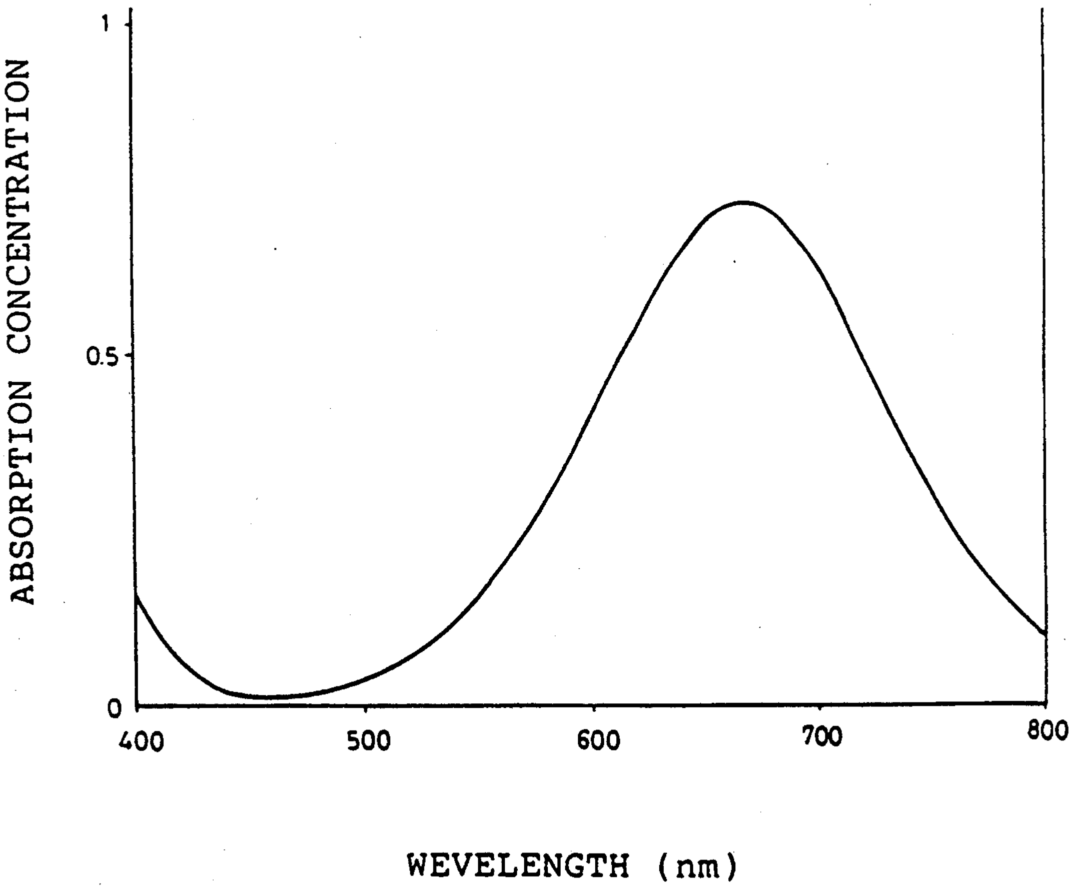
FIG. 1 shows an absorption spectrum in ethyl acetate of a dye produced by an oxidative coupling reaction of a compound of formula (XX), e.g., Compound (1), and 2-methyl-4-(N-ethyl-N-methanesulfonylethylamino) aniline.

DESCRIPTION OF PREFERRED EMBODIMENTS RELATING TO DYE FORMING COUPLERS OF FORMULA (I)

The silver halide color photosensitive material of the present invention will be described below in detail.

In formula (I), $R^1$ represents hydrogen atom or a substituent, and R and $R^2$ each represent a substituent. Examples of the substituents represented by R, $R^1$ and $R^2$ include an aryl group, an alkyl group, cyano group, an acyl group, formyl group, a carbamoyl group, an alkoxycarbonyl group, an aryloxycarbonyl group, formylamino group, an acylamino group, an alkoxycarbonylamino group, an aryloxycarbonylamino group, a sulfonamido group, a ureido group, a sulfamoylamino group, an alkylamino group, an arylamino group, an alkoxy group, an aryloxy group, a heteryloxy group, an alkylthio group, an arylthio group, a heterylthio group, a heterocyclic group, a halogen atom, hydroxyl group, nitro group, a sulfamoyl group, a sulfonyl group, an acyloxy group, a sulfonyloxy group, a carbamoyloxy group, an imido group, a sulfinyl group, a phosphoryl group, carboxyl group, phosphono group, and a non-substituted amino group. Among the above, any group which can have another substituent may be substituted with one of the above-described groups.

Specific examples of substituents represented by R, $R^1$ and $R^2$ include an aryl group (preferably having from 6 to 30 carbon atoms, e.g., phenyl, naphthyl, m-acetylaminophenyl, p-methoxyphenyl, etc.), an alkyl group (preferably having from 1 to 30 carbon atoms, e.g., methyl, trifluoromethyl, ethyl, isopropyl, heptafluoropropyl, t-butyl, n-octyl, n-dodecyl, etc.), cyano group, an alkyl, aryl or heteryl acyl group (preferably having from 1 to 30 carbon atoms, e.g., acetyl, pivaloyl, benzoyl, furoyl, 2-pyridylcarbonyl, etc.), formyl group, a carbamoyl group (preferably having from 1 to 30 carbon atoms, e.g., methylcarbamoyl, ethylcarbamoyl, dimethylcarbamoyl, n-octylcarbamoyl, etc.), an alkoxycarbonyl group (preferably having from 1 to 30 carbon atoms, e.g., methoxycarbonyl, ethoxycarbonyl, isopropoxycarbonyl, etc.), an aryloxycarbonyl group (preferably having from 7 to 30 carbon atoms, e.g., phenoxycarbonyl, p-methoxyphenoxycarbonyl, m-chlorophenoxycarbonyl, o-methoxyphenoxycarbonyl, etc.), formylamino group, an acylamino group [e.g., an alkylcarbonylamino group preferably having from 1 to 30 carbon atoms (acetylamino, propionylamino, cyanoacetylamino, etc.), an arylcarbonylamino group preferably having from 7 to 30 carbon atoms (e.g., benzoylamino, p-toluylamino, pentafluorobenzoylamino, m-methoxybenzoylamino, etc.), and a heterylcarbonyl amino group preferably having from 4 to 30 carbon atoms (e.g., 2-pyridylcarbonylamino, 3-pyridylcarbonylamino, furoylamino, etc.)], an alkoxycarbonylamino group (preferably having from 2 to 30 carbon atoms, e.g., methoxycarbonylamino, ethoxycarbonylamino, methoxyethoxycarbonylamino, etc.), an aryloxycarbonylamino group (preferably having from 7 to 30 carbon atoms, e.g., phenoxycarbonylamino, p-methoxyphenoxycarbonylamino, p-methylphenoxycarbonylamino, m-chlorophenoxycarbonylamino, etc.), a sulfonamido group (preferably having from 1 to 30 carbon atoms, e.g., methanesulfonamido, benzenesulfonamido, p-toluenesulfonamido, etc.), a ureido group (preferably having from 1 to 30 carbon atoms, e.g., methylureido, dimethylureido, p-cyanophenylureido, etc.), a sulfamoylamino group (preferably having from 1 to 30 carbon atoms, e.g., methylaminosulfonylamino, ethylaminosulfonylamino, anilinosulfonylamino, etc.), an alkylamino group (preferably having from 0 to 30 carbon atoms, e.g., amino, methylamino, dimethylamino, ethylamino, diethylamino, n-butylamino, etc.) an arylamino group (preferably having from 6 to 30 carbon atoms, e.g., anilino, N-methylanilino, etc.), an alkoxy group (preferably having from 1 to 30 carbon atoms, e.g., methoxy, ethoxy, isopropoxy, n-butoxy, 2-methoxyethoxy, n-dodecyloxy, etc.), an aryloxy group (preferably having from 6 to 30 carbon atoms, e.g., phenoxy, m-chlorophenoxy, p-methoxyphenoxy, o-methoxyphenoxy, etc.), a heteryloxy group (preferably having from 3 to 30 carbon atoms, e.g., tetrahydropyranyloxy, 3-pyridyloxy, 2-(1,3-benzimidazolyl)oxy), an alkylthio group (preferably having from 1 to 30 carbon atoms, e.g., methylthio, ethylthio, n-butylthio, t-butylthio, etc.), an arylthio group (preferably having from 6 to 30 carbon atoms, e.g., phenylthio), a heterylthio group (preferably having from 3 to 30 carbon atoms, e.g., 2-pyridylthio, 2-(1,3-benzoxazolyl)thio, 1-hexadecyl-1,2,3,4-tetrazolyl-5-thio, 1-(3-N-octadecylcarbamoyl)-phenyl-1,2,3,4-tetrazolyl-5-thio), a heterocyclic group (preferably having from 3 to 30 carbon atoms, e.g., 2-benzoxazolyl, 2-benzothiazolyl, 1-phenyl-2-benzimidazolyl, 5-chloro-1-tetrazolyl, 1-pyrrolyl, 2-furanyl, 2-pyridyl, 3-pyridyl, etc.), halogen atoms (fluorine, chlorine, and bromine), hydroxyl group, nitro group, a sulfamoyl group (preferably having from 0 to 30 carbon atoms, e.g., methylsulfamoyl, dimethylsulfamoyl, et.), an alkyl, aryl or heteryl sulfonyl group (preferably having from 1 to 30 carbon atoms, e.g., methanesulfonyl, benzenesulfonyl, toluenesulfonyl, etc.), an alkyl, aryl or heteryl acyloxy group. (preferably having from 1 to 30 carbon atoms, e.g., formyloxy, acetyloxy, benzoyloxy, etc.), an alkyl, aryl or heteryl sulfonyloxy group (preferably having from 1 to 30 carbon atoms, e.g., methanesulfonyloxy, etc.), a carbamoyloxy group (preferably having from 1 to 30 carbon atoms, e.g., methylcarbamoyloxy, diethylcarbamoyloxy, etc.), an imido group (preferably having from 4 to 30 carbon atoms, e.g., succinic acid imido, phthalimido, etc.), an alkyl or aryl sulfinyl group (preferably having from 1 to 30 carbon atoms, e.g., diethylaminosulfinyl), a phosphoryl group (preferably having from 0 to 30 carbon atoms, e.g., dimethoxyphosphoryl), carboxyl group, phosphono group, and a non-substituted amino group.

Preferably, at least either one of $R^1$ and $R^2$, preferably $R^1$, more preferably both $R^1$ and $R^2$, is an electron withdrawing group having a Hammett's $\sigma_p$ value of 0.35 or higher. More preferably, at least either one of $R^1$ and $R^2$, preferably $R^1$, is an electron withdrawing group having a Hammett's $\sigma_p$ value of 0.60 or higher. Particularly preferably, at least either one of $R^1$ and $R^2$, preferably $R^1$, is cyano group.

Hammett's substituent constant that is employed in this specification in connection with couplers of formula (I) will be explained below briefly. Hammett's rule is an empirical rule proposed by L. P. Hammett in 1935 to discuss quantitatively the effect of substituents on the reaction or equilibrium of benzene derivatives. At present, this rule is generally accepted as valid. There are two substituent constants, that is, $\sigma_p$ value and $\sigma_m$ value, obtained by the Hammett's rule. These values can be found in many general literatures on chemistry, and they are particularly detailed, for example, in "Lange's Handbook of Chemistry" 12th edition, edited by J. A Dean, 1979 (McGraw-Hill), and "Field of Chemistry", extra issue, No. 122, pp. 96–103, 1979 (Nankodo). Although in the present invention relating to formula (I) various substituents are specified or explained by using the Hammett's $\sigma_p$ value, it should be noted that substituents usable in the present invention are not necessarily limited to those which have Hammetts' values known in the above-described literatures and that the present invention, needless to say, includes substituents whose values are unknown in the literatures but will fall within the range of Hammett's $\sigma_p$ values when measured according to the Hammett's rule.

Preferable examples of electron withdrawing groups (including atoms) having a Hammett's $\sigma_p$ value of 0.35 or higher include cyano group ($\sigma_p$ value: 0.66), nitro group (0.78), carboxyl group (0.45), a perfluoroalkyl group (e.g., trifluoromethyl (0.54), perfluorobutyl, etc.), an acyl group (e.g. , acetyl (0.50), benzoyl (0.43), etc.), formyl group (0.42), a sulfonyl group (e.g., trifluoromethanesulfonyl (0.92), methanesulfonyl (0.72), benzenesulfonyl (0.70), etc.) , a sulfinyl group (e.g., methanesulfinyl (0.49)), a carbamoyl group (e.g., carbamoyl (0.36), methylcarbamoyl (0.36), phenylcarbamoyl, 2-chlorophenylcarbamoyl, etc.), an alkoxycarbonyl group (e.g., methoxycarbonyl (0.45), ethoxycarbonyl, diphenylmethylcarbonyl, etc.), an aryloxycarbonyl group (e.g., phenoxycarbonyl (0.44)), a heterocyclic group (e.g., pyrazolyl (0.37), 1-tetrazolyl (0.50), etc.) , an alkylsulfonyloxy group (e.g., methanesulfonyloxy (0.36) , a phosphoryl group (e.g., dimethoxyphosphoryl (0.60), diphenylphosphoryl, etc.), a sulfamoyl group (e.g., sulfamoyl (0.57)), pentachlorophenyl group, pentafluorophenyl group or a sulfonyl group substituted phenyl group (e.g., 2,4-dimethanesulfonylphenyl), and so forth.

Preferable examples of electron withdrawing groups having a Hammett's $\sigma_p$ value of 0.60 or higher include cyano group, nitro group, and a sulfonyl group.

X represents hydrogen atom or a group releasable on a coupling reaction with an oxidation product of a color developing agent, for example, an aromatic primary amine developing agent, (hereinafter referred to as "releasable group").

Specific examples of the releasable group include a halogen atom (e.g., fluorine, chlorine, bromine, etc.), an alkoxy group (e.g., ethoxy, dodecyloxy, methoxyethylcarbamoylmethoxy, carboxypropyloxy, methylsulfonylethoxy, etc.), an aryloxy group (e.g., 4-chlorophenoxy, 4-methoxyphenoxy, 4-carboxyphenoxy, etc.), an alkyl, aryl or heteryl acyloxy group (e.g., acetoxy, tetradecanoyloxy, benzoyloxy, etc.), an alkyl, aryl or heteryl sulfonyloxy group (e.g., a methanesulfonyloxy, toluenesulfonyloxy, etc.), an acylamino group (e.g., dichloroacetylamino, heptafluorobutyrylamino, etc.), a sulfonamido group (e.g., methanesulfonamido, p-toluenesulfonamido, etc.), an alkoxycarbonyloxy group (e.g., ethoxycarbonyloxy, benzyloxycarbonyloxy, etc.), an aryloxycarbonyloxy group (e.g., phenoxycarbonyloxy), an alkylthio group (e.g., carboxymethylthio), an arylthio group (e.g., 2-butoxy-5-tert-octylphenylthio), a heterocyclic thio group (e.g., tetrazolylthio), a carbamoylamino group (e.g., N-methylcarbamoylamino, N-phenylcarbamoylamino, etc.), a 5- or 6-membered nitrogen-containing heterocyclic group (e.g., imidazolyl, pyrazolyl, triazolyl, tetrazolyl, 1,2-dihydro-2-oxo-1-pyridyl, etc.), an imido group (e.g., succinimido, hydantoinyl, etc.), an aryl azo group (e.g., phenylazo), an alkyl, aryl or heteryl sulfinyl group (e.g., 2-butoxy-5-tert-octylphenylsulfinyl), an alkyl, aryl or heteryl sulfonyl group (e.g., 2-butoxy-5-tert-octylphenylsulfonyl), and so forth. These groups may be substituted with the substituent(s) allowed for $R_1$.

Releasable groups bonded via a carbon atom further include bis-form couplers which are obtained by condensation of a four-equivalent coupler by an aldehyde or a ketone. The releasable groups which are usable in the present invention may contain a photographically useful group such as a residue of a development inhibitor or a development accelerator.

Preferable examples of X are a hydrogen atom, a halogen atom, an aryloxy group and an arylthio group, more preferable examples of X are a hydrogen atom and a chlorine atom.

$Z^1$ represents a nonmetallic atom group necessary for forming a nitrogen-containing, six-membered, heterocyclic ring which has at least one dissociative group.

Examples of the four divalent coupling groups for forming a nitrogen-containing, six-membered, heterocyclic ring include —NH—, —N(R)—, —N═, —CH(R)—, —CH═, —C(R)═, —CO—, —S—, —SO—, and $—SO_2—$ (wherein R represents a substituent, which may be selected from among those mentioned for $R^1$).

Examples of the dissociative group are groups having an acid proton, e.g., —NH—, —CH(R)—, etc., preferably those having a pKa value of from 3 to 12 in water.
The dye forming couplers of formula (I) are preferably those which are represented by formulae (II) to (XIX):
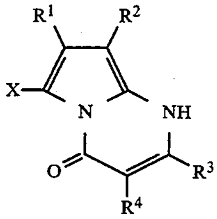
(II)
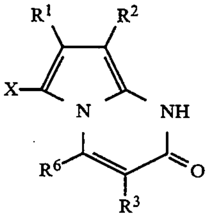
(III)
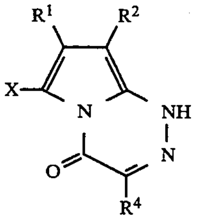
(IV)
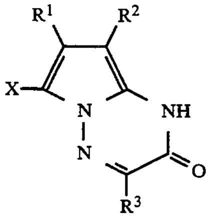
(V)
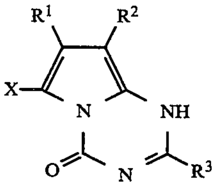
(VI)
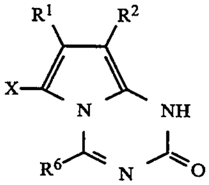
(VII)
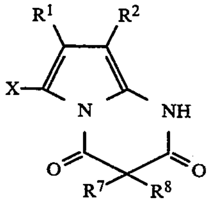
(IX)
-continued
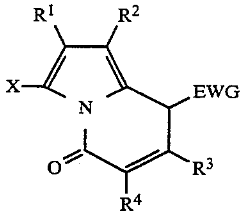
(X)
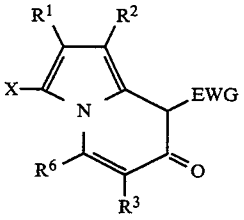
(XI)
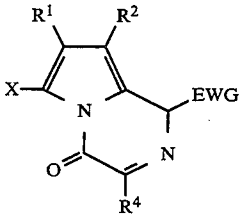
(XII)
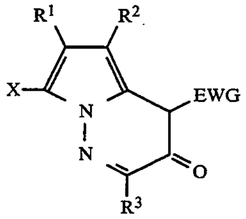
(XIII)
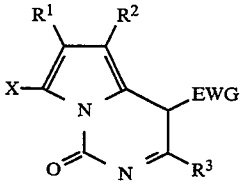
(XIV)
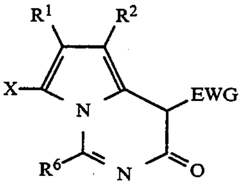
(XV)
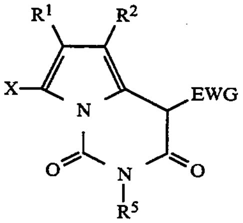
(XVI)

-continued (XVII)

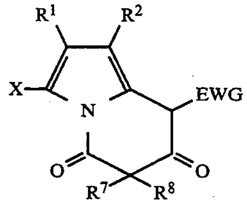

(XVIII)

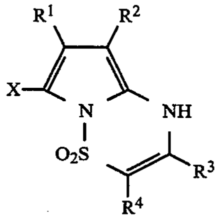

(XIX)

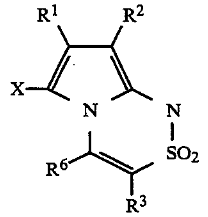

In the above formulae, $R^1$ and $R^2$ are the same as those in formula (I). $R^3$, $R^5$, $R^6$, $R^7$ and $R^8$ each represent hydrogen atom or a substituent, and $R^4$ represents a substituent. EWG represents an electron withdrawing group having a Hammett's $\sigma_p$ value of 0.35 or higher.

Examples of the substituents represented by $R^3$, $R^4$, $R^5$, $R^6$, $R^7$, $R^8$, and are the same as those mentioned for $R^1$.

The couplers represented by formula (I) may form dimers or other polymers having a coupler residue of formula (I) in the groups represented by $R_1$ to $R_8$. Alternatively, the couplers may form monopolymers or copolymers in which the groups of $R_1$ to $R_8$ have polymer chains. Typical examples of such mono or copolymers are those of addition polymer ethylene type unsaturated compounds having a coupler residue of formula (I). In this case, the polymers may contain one or more color developing repeating units having a coupler residue of formula (I). The polymers may be copolymers containing as a copolymerization component one or more non-color developing ethylene type monomers such as acrylic esters, methacrylic esters and maleates.

The couplers of formula (I) of the present invention are effectively used as cyan couplers.

Typical examples of compounds of formula (I) usable as couplers in the present invention will be shown below for illustrative purposes only, but the present invention is not limited to these examples.

Substituents employed in the compound examples will be shown below in numerical order.

H ①

F ②

Cl ③

Br ④

I ⑤

-continued

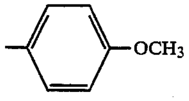
⑥

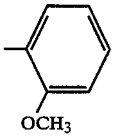
⑦

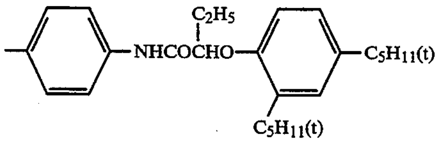
⑧

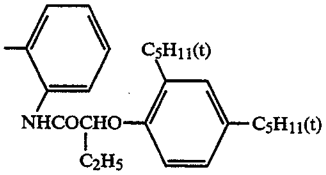
⑨

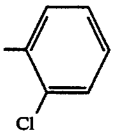
⑩

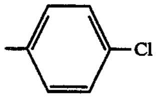
⑪

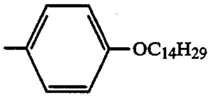
⑫

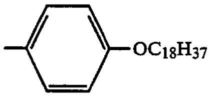
⑬

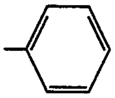
⑭

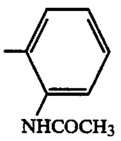
⑮

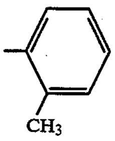
⑯

-continued
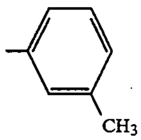
(17)
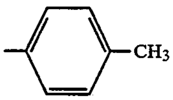
(18)
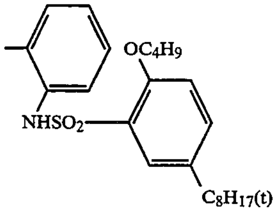
(19)
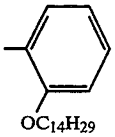
(20)
$CH_3$ (21)
$C_2H_5$ (22)
$-C_3H_7(i)$ (23)
$-C_4H_9(t)$ (24)
$-CF_3$ (25)
$-C_3F_7$ (26)
$-(CH_2)_3OC_{12}H_{25}$ (27)
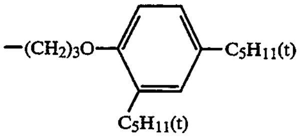
(28)
$-C_{16}H_{33}$ (29)
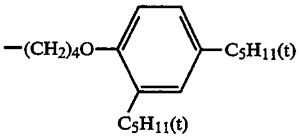
(30)
$-CN$ (31)
$-COCH_3$ (32)
$-COC_{15}H_{31}$ (33)
$-COC_4H_9(t)$ (34)
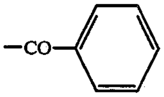
(35)
$-CONH_2$ (36)
-continued
$-CONHC_{16}H_{33}$ (37)
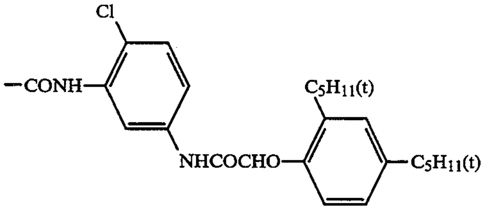
(38)
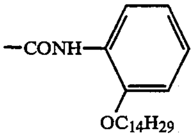
(39)
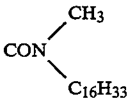
(40)
$-CO_2CH_3$ (41)
$-CO_2C_{16}H_{33}$ (42)
$-CO_2C_2H_5$ (43)
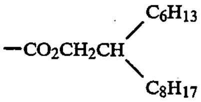
(44)
$-CO_2CH_2(CF_2)_6F$ (45)
$-NHCOCH_3$ (46)
$-NHCOCH_2CN$ (47)
$-NHCOC_4H_9(t)$ (48)
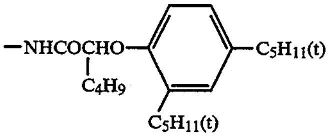
(49)
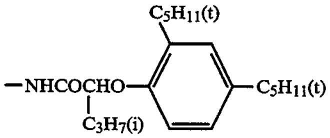
(50)
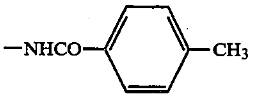
(51)
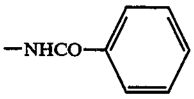
(52)

-continued
(53)
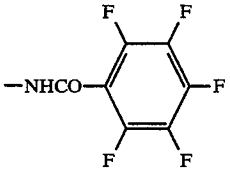
(54)
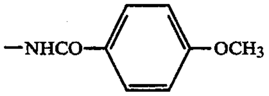
(55)
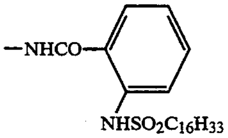
$-NHCO_2C_2H_5$ (56)
$-NHCO_2C_4H_9(i)$ (57)
(58)
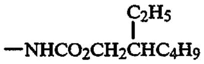
$-NHSO_2CH_3$ (59)
$-NHSO_2C_{16}H_{33}$ (60)
(61)
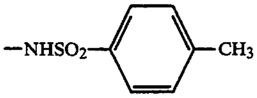
(62)
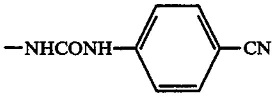
(63)
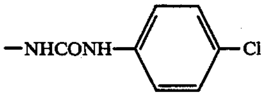
(64)
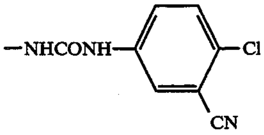
(65)
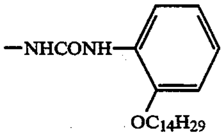
(66)
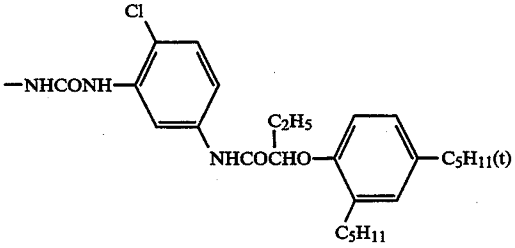
-continued
(67)
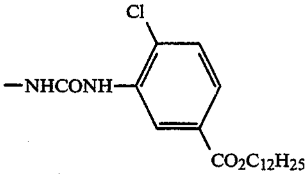
(68)
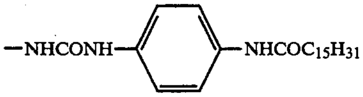
$-N(CH_3)_2$ (69)
(70)
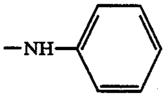
$-OCH_3$ (71)
$-OC_2H_5$ (72)
$-OCH_2CH_2OCH_3$ (73)
$-OCH_2CH_2OH$ (74)
$-OCH_2CH_2SCH_2CH_2OH$ (75)
(76)
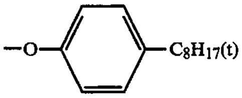
(77)
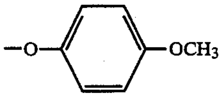
(78)
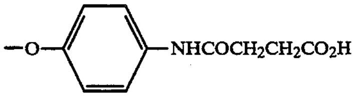
$-SCH_2CH_2OH$ (79)
$-SCH_2CO_2H$ (80)
$-SCH_2CH_2CO_2H$ (81)
(82)
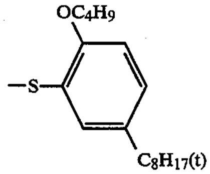
(83)
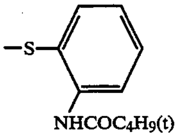
(84)
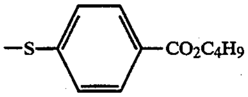

-continued (85)

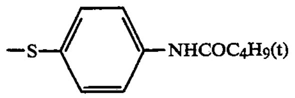

(86)

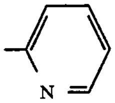

(87)

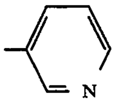

(88)

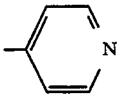

(89)

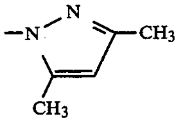

(90)

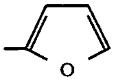

(91)

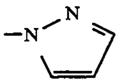

(92)

—OH (93)

$—NO_2$ (94)

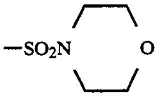

(95)

$—SO_2NH(CH_2)_3OC_{12}H_{25}$ (96)

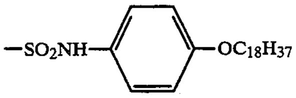

(97)

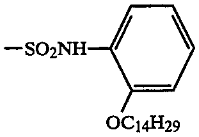

(98)

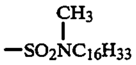

(99)

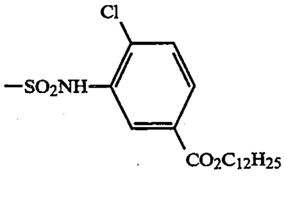

(100)

$—SO_2CH_3$

-continued (101)

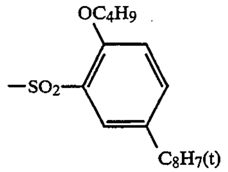

(102)

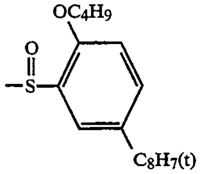

(103)

$—SO_2C_4H_9$

Tables below show typical examples of compounds usable as couplers of formula (I) in the present invention for illustrative purposes only, but the present invention is not limited to these examples.

TABLE 1

| Coupler No. | $R^1$ | $R^2$ | $R^3$ | $R^4$ | $R^5$ | $R^6$ | $R^7$ | $R^8$ | X |
|---|---|---|---|---|---|---|---|---|---|
| (II)-1 | 14 | 31 | 13 | 21 | — | — | — | — | 1 |
| (II)-2 | 14 | 31 | 13 | 21 | — | — | — | — | 3 |
| (II)-3 | 88 | 31 | 28 | 21 | — | — | — | — | 3 |
| (II)-4 | 42 | 31 | 12 | 21 | — | — | — | — | 3 |
| (II)-5 | 12 | 31 | 15 | 21 | — | — | — | — | 3 |
| (II)-6 | 31 | 31 | 19 | 21 | — | — | — | — | 3 |
| (II)-7 | 31 | 31 | 20 | 21 | — | — | — | — | 3 |
| (II)-8 | 16 | 40 | 13 | 21 | — | — | — | — | 1 |
| (II)-9 | 9 | 31 | 14 | 21 | — | — | — | — | 3 |
| (II)-10 | 8 | 31 | 14 | 21 | — | — | — | — | 3 |
| (II)-11 | 43 | 43 | 13 | 21 | — | — | — | — | 3 |
| (II)-12 | 14 | 31 | 19 | 23 | — | — | — | — | 84 |
| (II)-13 | 25 | 31 | 19 | 23 | — | — | — | — | 77 |
| (II)-14 | 14 | 45 | 67 | 23 | — | — | — | — | 79 |
| (II)-15 | 25 | 31 | 66 | 23 | — | — | — | — | 83 |
| (II)-16 | 14 | 31 | 68 | 23 | — | — | — | — | 91 |

TABLE 2

| Coupler No. | $R^1$ | $R^2$ | $R^3$ | $R^4$ | $R^5$ | $R^6$ | $R^7$ | $R^8$ | X |
|---|---|---|---|---|---|---|---|---|---|
| (III)-1 | 14 | 31 | 44 | — | — | 21 | — | — | 1 |
| (III)-2 | 14 | 31 | 44 | — | — | 21 | — | — | 3 |
| (III)-3 | 14 | 31 | 44 | — | — | 1 | — | — | 1 |
| (III)-4 | 18 | 31 | 45 | — | — | 1 | — | — | 3 |
| (III)-5 | 31 | 31 | 45 | — | — | 1 | — | — | 3 |
| (III)-6 | 31 | 31 | 42 | — | — | 1 | — | — | 1 |
| (III)-7 | 14 | 31 | 37 | — | — | 1 | — | — | 3 |
| (III)-8 | 15 | 31 | 38 | — | — | 1 | — | — | 3 |
| (III)-9 | 16 | 31 | 39 | — | — | 1 | — | — | 3 |
| (III)-10 | 43 | 43 | 39 | — | — | 1 | — | — | 3 |
| (III)-11 | 31 | 43 | 44 | — | — | 1 | — | — | 3 |
| (III)-12 | 45 | 31 | 44 | — | — | 1 | — | — | 3 |
| (III)-13 | 7 | 31 | 44 | — | — | 72 | — | — | 3 |
| (III)-14 | 14 | 31 | 38 | — | — | 72 | — | — | 3 |
| (III)-15 | 10 | 44 | 1 | — | — | 69 | — | — | 3 |
| (III)-16 | 87 | 31 | 44 | — | — | 1 | — | — | 82 |
| (III)-17 | 14 | 31 | 44 | — | — | 1 | — | — | 83 |
| (III)-18 | 88 | 31 | 38 | — | — | 1 | — | — | 76 |
| (III)-19 | 14 | 31 | 37 | — | — | 1 | — | — | 80 |
| (III)-20 | 14 | 31 | 40 | — | — | 1 | — | — | 91 |

TABLE 3

| Coupler No. | $R^1$ | $R^2$ | $R^3$ | $R^4$ | $R^5$ | $R^6$ | $R^7$ | $R^8$ | X |
|---|---|---|---|---|---|---|---|---|---|
| (IV)-1 | 14 | 31 | — | 13 | — | — | — | — | 1 |
| (IV)-2 | 25 | 31 | — | 19 | — | — | — | — | 3 |
| (IV)-3 | 43 | 31 | — | 28 | — | — | — | — | 80 |
| (IV)-4 | 31 | 14 | — | 27 | — | — | — | — | 83 |
| (V)-1 | 14 | 31 | 13 | — | — | — | — | — | 1 |

TABLE 3-continued

| Coupler No. | $R^1$ | $R^2$ | $R^3$ | $R^4$ | $R^5$ | $R^6$ | $R^7$ | $R^8$ | X |
|---|---|---|---|---|---|---|---|---|---|
| (V) - 2 | 25 | 31 | 20 | — | — | — | — | — | 3 |
| (V) - 3 | 43 | 31 | 30 | — | — | — | — | — | 79 |
| (V) - 4 | 31 | 14 | 29 | — | — | — | — | — | 84 |
| (VI) - 1 | 14 | 31 | 28 | — | — | — | — | — | 1 |
| (VI) - 2 | 25 | 31 | 27 | — | — | — | — | — | 3 |
| (VI) - 3 | 43 | 31 | 19 | — | — | — | — | — | 81 |
| (VI) - 4 | 31 | 14 | 12 | — | — | — | — | — | 82 |
| (VII) - 1 | 14 | 31 | — | — | — | 9 | — | — | 1 |
| (VII) - 2 | 25 | 31 | — | — | — | 13 | — | — | 3 |
| (VII) - 3 | 43 | 31 | — | — | — | 27 | — | — | 80 |
| (VII) - 4 | 31 | 14 | — | — | — | 28 | — | — | 85 |
| (IX) - 1 | 14 | 31 | — | — | — | — | 27 | 27 | 1 |
| (IX) - 2 | 25 | 31 | — | — | — | — | 27 | 27 | 3 |
| (IX) - 3 | 43 | 31 | — | — | — | — | 28 | 28 | 81 |
| (IX) - 4 | 31 | 14 | — | — | — | — | 28 | 28 | 84 |

TABLE 4

| Coupler No. | $R^1$ | $R^2$ | $R^3$ | $R^4$ | $R^5$ | $R^6$ | $R^7$ | $R^8$ | EWG | X |
|---|---|---|---|---|---|---|---|---|---|---|
| (X) - 1 | 14 | 31 | 13 | 21 | — | — | — | — | 31 | 1 |
| (X) - 2 | 25 | 31 | 19 | 23 | — | — | — | — | 31 | 3 |
| (X) - 3 | 43 | 31 | 67 | 23 | — | — | — | — | 43 | 79 |
| (X) - 4 | 31 | 14 | 68 | 23 | — | — | — | — | 31 | 82 |
| (XI) - 1 | 14 | 31 | 44 | — | — | 21 | — | — | 31 | 1 |
| (XI) - 2 | 25 | 31 | 45 | — | — | 1 | — | — | 43 | 3 |
| (XI) - 3 | 43 | 31 | 44 | — | — | 72 | — | — | 31 | 80 |
| (XI) - 4 | 31 | 14 | 1 | — | — | 69 | — | — | 31 | 83 |
| (XII) - 1 | 14 | 31 | — | 19 | — | — | — | — | 43 | 1 |
| (XII) - 2 | 25 | 31 | — | 13 | — | — | — | — | 31 | 3 |
| (XII) - 3 | 43 | 31 | — | 27 | — | — | — | — | 31 | 81 |
| (XII) - 4 | 31 | 14 | — | 28 | — | — | — | — | 43 | 84 |
| (XIII) - 1 | 14 | 31 | 20 | — | — | — | — | — | 31 | 1 |
| (XIII) - 2 | 25 | 31 | 13 | — | — | — | — | — | 31 | 3 |
| (XIII) - 3 | 43 | 31 | 29 | — | — | — | — | — | 43 | 79 |
| (XIII) - 4 | 31 | 14 | 30 | — | — | — | — | — | 31 | 85 |
| (XIV) - 1 | 14 | 31 | 19 | — | — | — | — | — | 31 | 1 |
| (XIV) - 2 | 25 | 31 | 12 | — | — | — | — | — | 43 | 3 |
| (XIV) - 3 | 43 | 31 | 27 | — | — | — | — | — | 31 | 80 |
| (XIV) - 4 | 31 | 14 | 28 | — | — | — | — | — | 31 | 82 |

TABLE 5

| Coupler No. | $R^1$ | $R^2$ | $R^3$ | $R^4$ | $R^5$ | $R^6$ | $R^7$ | $R^8$ | EWG | X |
|---|---|---|---|---|---|---|---|---|---|---|
| (XV) - 1 | 14 | 31 | — | — | — | 13 | — | — | 43 | 1 |
| (XV) - 2 | 25 | 31 | — | — | — | 9 | — | — | 31 | 3 |
| (XV) - 3 | 43 | 31 | — | — | — | 28 | — | — | 31 | 81 |
| (XV) - 4 | 31 | 14 | — | — | — | 27 | — | — | 43 | 83 |
| (VXI) - 1 | 14 | 31 | — | — | 8 | — | — | — | 31 | 1 |
| (VXI) - 2 | 25 | 31 | — | — | 9 | — | — | — | 31 | 3 |
| (VXI) - 3 | 43 | 31 | — | — | 13 | — | — | — | 43 | 79 |
| (VXI) - 4 | 31 | 14 | — | — | 19 | — | — | — | 31 | 84 |
| (XVII) - 1 | 14 | 31 | — | — | — | — | 27 | 27 | 31 | 1 |
| (XVII) - 2 | 25 | 31 | — | — | — | — | 27 | 27 | 43 | 3 |
| (XVII) - 3 | 43 | 31 | — | — | — | — | 28 | 28 | 31 | 80 |
| (XVII) - 4 | 31 | 14 | — | — | — | — | 28 | 28 | 31 | 85 |
| (XVIII) - 1 | 14 | 31 | 13 | 21 | — | — | — | — | — | 1 |
| (XVIII) - 2 | 25 | 31 | 28 | 21 | — | — | — | — | — | 3 |
| (XVIII) - 3 | 43 | 31 | 19 | 23 | — | — | — | — | — | 81 |
| (XVIII) - 4 | 31 | 14 | 67 | 23 | — | — | — | — | — | 83 |
| (XIX) - 1 | 14 | 31 | 44 | — | — | 21 | — | — | — | 1 |
| (XIX) - 2 | 25 | 31 | 45 | — | — | 1 | — | — | — | 3 |
| (XIX) - 3 | 43 | 31 | 38 | — | — | 72 | — | — | — | 79 |
| (XIX) - 4 | 31 | 14 | 40 | — | — | 1 | — | — | — | 84 |

Synthesis examples of typical couplers of formula (I) according to the present invention will be described below.

SYNTHESIS EXAMPLE 1

Synthesis of Coupler (III)-1

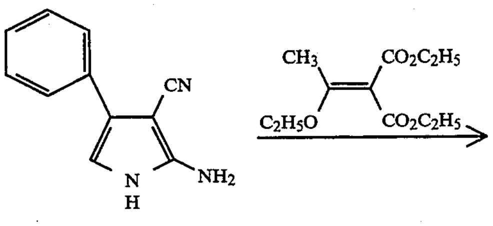

Compound a

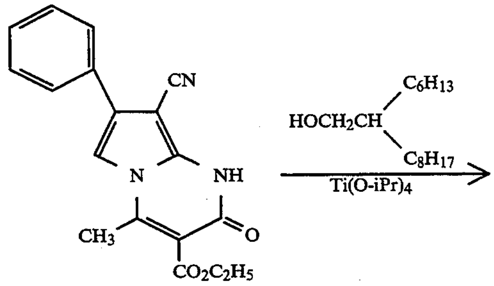

Compound b

Coupler (III)-1

18.3 g of 2-amino-3-cyano-4-phenylpyrrole (compound a), readily obtained by condensation of 2-aminoacetophenone hydrochloride and malononitrile in the presence of an alkali, and 25.3 g of ethoxyethylidene diethyl malonate were dispersed in 300 ml of ethanol, and 22.0 ml of a solution of 28% sodium methylate in methanol was added to the resulting dispersion, followed by heating under reflux for 5 hours. Thereafter, the reaction mixture was allowed to cool, and ethyl acetate was added thereto. After washing with water, the organic solvent was concentrated to precipitate crystals, which were then collected by filtration to obtain 11.6 g of compound b. Subsequently, 50 ml of fine oxocol and 2.0 g of titanium isopropoxide (Ti(O—i—Pr)$_4$) were added to the compound b, and the resulting mixture was heated for 6 hours at an oil-bath temperature of 130° C. to 140° C. After being allowed to cool, the reaction mixture was purified by silica gel chromatography (hexane/ethyl acetate=1/1) to obtain 14.7 g of coupler (III)-1 in the form of lemon yellow oily matter.

SYNTHESIS EXAMPLE 2

Synthesis of Coupler (III)-3

Compound a 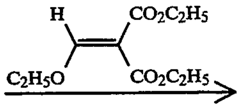

-continued

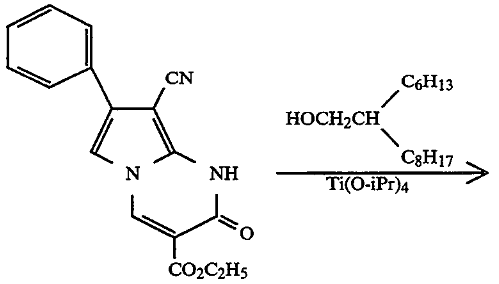

Compound c

Coupler (III)-3

18.3 g of 2-amino-3-cyano-4-phenylpyrrole (compound a) and 24.0 g of ethoxymethylene diethyl malonate were dispersed in 400 ml of ethanol, and 22.0 ml of a solution of 28% sodium methylate in methanol was added to the resulting dispersion, followed by heating under reflux for 1 hour. After the reaction mixture was allowed to cool, precipitated crystals were collected by filtration to obtain 28.0 g of compound c. Subsequently, 150 ml of fine oxocol 1600 and 4.0 g of Ti(O—i—Pr)$_4$ were added to the compound c, and the resulting mixture was heated for 2 hours at an oil-bath temperature of 130° C. to 140° C. After being allowed to cool, the reaction mixture was purified by silica gel chromatography to obtain 36.2 g of coupler (III)-3.

SYNTHESIS EXAMPLE 3

Synthesis of Coupler (II)-1

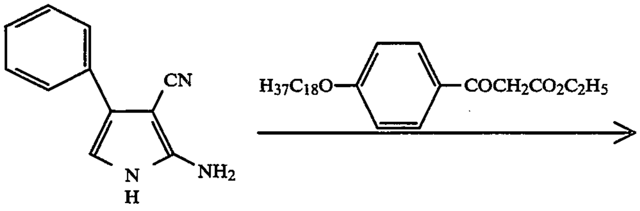

Coupler (II)-1

Compound a 18.3 g of 2-amino-3-cyano-4-phenylpyrrole (compound a) and 46.0 g of p-octadecyloxybenzoylethyl acetate were dispersed in 300 ml of acetic acid, and the resulting dispersion was heated under reflux for 8 hours. After the reaction mixture was allowed to cool, 1 liter of ethyl acetate and 1 liter of water were added thereto to precipitate crystals, which were then collected by filtration to obtain 29.0 g of coupler (II)-1.

The releasable group may be introduced by the following four different methods depending upon the kind of releasable group.

(1) When the releasable group is a halogen atom

The most common halogen atom is chlorine atom, and such a releasable group can be obtained by chlorinating a four-equivalent coupler containing a hydrogen atom as X with sulfuryl chloride, N-chlorosuccinimide, etc. in a halogeno hydrocarbon solution (e.g., chloroform, methylene chloride, etc.).

(2) When the releasable group is bonded to the coupling position via an oxygen atom (i) In one method, the coupling position of a four-equivalent coupler is halogenated and reacted with a phenol compound in the presence of a base. (ii) In another method, a hydroxyl group at the coupling position of a four-equivalent coupler is reacted with an active halide compound in the presence of a base.

(3) When the releasable group is bonded to the coupling position via a sulfur atom (i) In one method, a four-equivalent coupler and sulfenyl chloride which is to be a releasable group are reacted with each other in the presence or absence of a base. (ii) In another method, a mercapto group is introduced to the coupling position of a four-equivalent coupler so that a halide reacts on this mercapto group.

(4) When the releasable group is bonded to the coupling position via a nitrogen atom (i) In one method, the coupling position of a four-equivalent coupler is nitrosated by a proper nitrosating agent, reduced by a proper method (e.g., a hydrogenation method that uses, for example, Pd-carbon, as a catalyst, or a chemical reduction method that uses stannous chloride) and thereafter allowed to react with one of various halides; (ii) in another method, the coupling position of a four-equivalent coupler is halogenated by a proper halogenating agent (e.g., sulfuryl chloride) and thereafter substituted with a nitrogen heteroring in the presence of a proper basic catalyst according to the method described in Japanese Patent Application Post-Exam. Publication No. 56-45135 (1981); and (iii) in another method, a 6 $\pi$ or 10 $\pi$ electronic aromatic nitrogen heteroring is introduced into a halogenated coupler in the presence or absence of an aprotic polar solvent.

The above releasable group introducing methods are described, for example, in U.S. Pat. Nos. 3,894,875, 3,933,501, 4,296,199, 3,227,554, 3,476,563, 4,296,200, 4,234,678, 4,228,233, 4,351,897, 4,264,723, 4,366,237, 3,408,194, 3,725,067, 3,419,391 and 3,926,631, Japanese Patent Application Post-Exam. Publication Nos. 56-45135 (1981) and 57-36577 (1982), and Japanese Patent Application Laid-Open (KOKAI) Nos. 57-70871 (1982), 57-96343 (1982), 53-52423 (1983), 51-105820 (1976), 53-129035 (1978) and 54-48540 (1979).

The other compounds can also be synthesized by a similar method.

The photosensitive material of the present invention has at least one layer containing the coupler of formula (I) of the present invention on a support. Any hydrophilic colloidal layer on the support can contain the coupler of the present invention. General color photosensitive materials can be formed by coating a support with at least one blue-sensitive silver halide emulsion layer, at least one green-sensitive silver halide emulsion layer and at least one red-sensitive silver halide emulsion layer in the mentioned order or any order different therefrom. An infrared-sensitive silver halide emulsion layer may be used in place of at least one of the above-described photosensitive emulsion layers. Each of these photosensitive emulsion layers contains a silver halide emulsion having sensitivity to the corresponding wavelength region and a color coupler capable of forming a dye of a color complementary to the light to which it is sensitive, thereby enabling color reproduction by the subtractive color process. However, the arrangement may also be such that the photosensitive layers and the developed hues of the couplers do not have the above-described relationship.

When the coupler of formula (I) of the present invention is applied to a color photosensitive material, it is particularly preferable to use it in a red-sensitive silver halide emulsion layer.

The coupler of formula (I) of the present invention is added to a photosensitive material in an amount of form $1\times10^{-3}$ to 1 mol, preferably from $2\times10^{-3}$ to $3\times10^{-1}$ mol, per mol of silver halide.

The coupler of formula (I) of the present invention can be introduced into a photosensitive material by various known dispersion methods. It is preferable to employ an oil-in-water dispersion method wherein the coupler is dissolved in a high-boiling organic solvent (together with a low-boiling organic solvent, if necessary), dispersed in an aqueous gelatin solution, and added to a silver halide emulsion.

Examples of high-boiling solvents which are usable in the oil-in-water dispersion method are described, for example, in U.S. Pat. No. 2,322,027. The steps and effects of a latex dispersion method, as one polymer dispersion method, and specific examples of latices for impregnation are described in U.S. Pat. No. 4,199,363, West German Patent Application (OLS) Nos. 2,541,274 and 2,541,230, Japanese Patent Application Post-Exam. Publication No. 53-41091 (1978), and European Patent Publication No. 029104. A dispersion method using an organic solvent-soluble polymer is described in PCT No. W088/00723.

Specific examples of high-boiling organic solvents which are usable in the oil-in-water dispersion method are phthalic esters (e.g., dibutyl phthalate, dioctyl phthalate, dicyclohexyl phthalate, di-2-ethylhexyl phthalate, decyl phthalate, bis(2,4-di-tert-amylphenyl) isophthalate, bis(1,1-diethylpropyl) phthalate, etc.), phosphoric or phosphonic esters (e.g., diphenyl phosphate, triphenyl phosphate, tricresyl phosphate, 2-ethylhexyldiphenyl phosphate, dioctylbutyl phosphate, tricyclohexyl phosphate, tri-2-ethylhexyl phosphate, tridodecyl phosphate, di-2-ethylhexylphenyl phosphate, etc.), benzoic acid esters (e.g., 2-ethylhexyl benzoate, 2,4-dichlorobenzoate, dodecyl benzoate, 2-ethylhexyl-p-hydroxybenzoate, etc.), amides (e.g., N,N-diethyldodecanamide, N,N-diethyllaurylamide, etc.) , alcohols or phenols (e.g., isostearyl alcohol, 2,4-di-tert-amylphenol, etc.) , aliphatic esters (e.g., dibutoxyethyl succinate, di-2-ethylhexyl succinate, 2-hexyldecyl tetradecanoate, tributyl citrate, diethyl azelate, isostearyl lactate, trioctyl citrate, etc.), aniline derivatives (e.g., N,N-dibutyl- 2-butoxy-5-tert-octylaniline), chlorinated paraffins (e.g., paraffins having a chlorine content of from 10 to 80%), trimesic esters (e.g., tributyl trimesate), dodecylbenzene, diisopropylnaphthalene, phenols (e.g., 2,4-di-tert-amylphenol, 4-dodecyloxyphenol, 4-dodecyloxycarbonylphenol, 4-(4-dodecyloxyphenylsulfonyl)phenol, etc.), carboxylic acids (e.g., 2-(2,4-di-tert-amylphenoxybutyric acid, 2-ethoxyoctanedecanoic acid, etc.), and alkylphosphates (e.g., di-(2-ethylhexyl) phosphate, diphenyl phosphate, etc.). Organic solvents having a boiling point of from 30° C. to about 160° C. may be used in combination as an auxiliary solvent. Typical examples of such an auxiliary solvent are ethyl acetate, butyl acetate, ethyl propionate, methyl ethyl ketone, cyclohexanone, 2-ethoxyethyl acetate, and dimethylformamide.

The high-boiling organic solvent is used in an amount of from 0 to 10.0 times, preferably from 0 to 4.0 time, the weight of the coupler.

There is no particular restriction on the number of silver halide emulsion layers and non-photosensitive layers in the photosensitive material of the present invention. A typical example of the photosensitive material has on a support at least one photosensitive layer comprising a plurality of silver halide emulsion layers which are substantially the same in color sensitivity but different in photosensitivity. The photosensitive layer is a unit photosensitive layer having color sensitivity to one of blue light, green light and red light. In a multilayer silver halide color photosensitive material, unit photosensitive layers are generally arranged in the following order from the support side: a red-sensitive layer, a green-sensitive layer and a blue-sensitive layer. However, the order in which the unit photosensitive layers are arranged may be reversed according to each particular purpose. It is also possible to arrange the unit photosensitive layers such that a photosensitive layer of one color is sandwiched between a pair of photosensitive layers of another color.

It is also possible to provide various kinds of non-photosensitive layer, for example, an interlayer, in between a pair of silver halide photosensitive layers and on the top and bottom of the photosensitive material as uppermost and lowermost layers.

The interlayer may contain a coupler, a DIR compound, etc. such as those described in the specifications of Japanese Patent Application Laid-Open (KOKAI) Nos. 61-43748 (1986), 59-113438 (1984), 59-113440 (1984), 61-20037 (1986) and 61-20038 (1986). The interlayer may also contain a color amalgamation preventing agent as in the common practice.

A plurality of silver halide emulsion layers that constitute each unit photosensitive layer can preferably employ a double-layer configuration comprising a high-sensitivity emulsion layer and a low-sensitivity emulsion layer, as described in West German Patent No. 1,121,470 and British Patent No. 923,045. In general, it is preferable to arrange silver halide emulsion layers so that the photosensitivity lowers gradually toward the support. In addition, a non-photosensitive layer may be provided between each pair of halide emulsion layers. It is also possible to install a low-sensitivity emulsion layer at the side remote from the support and a high-sensitivity emulsion layer at the side closer to the support, as described in Japanese Patent Application Laid-Open (KOKAI) Nos. 57-112751 (1982), 62-200350 (1987), 62-206541 (1987), 62-206543 (1987), etc.

As specific examples, a plurality of silver halide emulsion layers may be installed in the following order from the side remote from the support: a low-sensitivity blue-sensitive layer (BL)/a high-sensitivity blue-sensitive layer (BH)/a high-sensitivity green-sensitive layer (GH)/a low-sensitivity green-sensitive layer (GL)/a high-sensitivity red-sensitive layer (RH)/a low-sensitivity red-sensitive layer (RL); or BH/BL/GL/GH/RH/RL; or BH/BL/GH/GL/RL/RH.

Further, it is possible to arrange a plurality of silver halide emulsion layers in the following order from the side remote from the support: a blue-sensitive layer/GH/RH/GL/RL, as described in Japanese Patent Application Post-Exam Publication No. 55-34932 (1980). It is also possible to arrange a plurality of silver halide emulsion layers in the following order from the side remote from the support: a blue-sensitive layer/GL/RL/GH/RH, as described in Japanese Patent Application Laid-Open (KOKAI) Nos. 56-25738 (1981) and 62-63936 (1987).

In addition, it is possible to employ a layer configuration in which a silver halide emulsion layer having the highest sensitivity forms an upper layer, a silver halide emulsion layer having a lower sensitivity than that of the upper layer forms a middle layer, and a silver halide emulsion layer having a lower sensitivity than that of the middle layer forms a lower layer, thereby constituting a layer configuration comprising three layers having different sensitivities so that the sensitivity gradually lowers toward the support, as described in Japanese Patent Application Post-Exam Publication No. 49-15495 (1974). Even in such a layer configuration, which comprises three layers having different sensitivities, the three layers may be disposed in the same color sensitive layer in the following order from the side remote from the support: a medium-sensitivity emulsion layer/a high-sensitivity emulsion layer/a low-sensitivity emulsion layer, as described in Japanese Patent Application Laid-Open (KOKAI) No. 59-202464 (1984).

The three layers may also be arranged in the order: a high-sensitivity emulsion layer/a low-sensitivity emulsion layer/a medium-sensitivity emulsion layer, or a low-sensitivity emulsion layer/a medium-sensitivity emulsion layer/a high-sensitivity emulsion layer. In the case of a layer configuration comprising four or more layers also, the arrangement of the layers may be changed as described above.

For improvement in color reproduction, it is preferable to dispose adjacently or in close proximity to the main photosensitive layer an interlayer effect donor layer (CL), which is different in spectral sensitivity distribution from the main photosensitive layer, e.g., BL, GL, RL, etc. as described in U.S. Pat. Nos. 4,663,271, 4,705,744 and 4,707,436, and Japanese Patent Application Laid-Open (KOKAI) Nos. 62-160448 (1987) and 63-89850 (1988).

Thus, a variety of layer configurations and arrangements can be selected according to various purposes of the photosensitive material.

Silver halides which are usable in the present invention are silver chloride, silver bromide, silver chlorobromide, silver iodochlorobromide, silver iodobromide, silver iodochloride, etc.

A preferred halogen composition depends on the desired type of photosensitive material. For example, a silver chlorobromide emulsion is preferred for use in color papers; a silver iodobromide emulsion having a silver iodide content of from 0.5 to 30 mol % (preferably from 2 to 25 mol %) is preferred in photosensitive materials for photography, such as color negative films and color reversal films; and a silver bromide emulsion or a silver chlorobromide emulsion is preferred in direct positive color photosensitive materials. In photosensitive materials suited for rapid processing, an emulsion having a high silver chloride content (hereinafter referred to as "high silver chloride emulsion) is preferably used. Such a high silver chloride emulsion preferably has a silver chloride content of 90 mol % or more, more preferably 95 mol % or more.

Silver halide grain in the high silver chloride emulsion preferably has localized silver bromide phases in the inside and/or on the surface of the individual grains in layer or non-layer form, as described above. The localized phase preferably has a silver bromide content of at least 10 mol %, more preferably more than 20 mol %. These localized phases may be present in the inside of the grains or on the surface (e.g., edges, corners, or planes) of the grains. One preferred example of such localized phases is an epitaxially grown portion on the corner(s) of grains.

In the present invention, a silver chlorobromide or silver chloride emulsion containing substantially no silver iodide is preferably employed. The expression "containing substantially no silver iodide" as used herein means that the silver iodide content is not more than 1 mol %, more preferably not more than 0.2 mol %.

While the halogen composition of a silver halide emulsion may be either the same or different among individual grains, use of an emulsion having the same halogen composition among grains makes it easy to obtain grains having uniform properties. The halogen composition may be uniformly distributed throughout the individual grains (homogeneous grains), or the individual grains may have a non-uniformly distributed halogen composition to form a laminate structure comprising a core and a single-layered or multi-layered outer shell or may have a non-layered portion differing in halogen composition in the inside or on the surface thereof (when such a portion is on the surface, it is fused on the edge, corner or plane of the grain). Either of the latter two types of grain is preferred to the homogeneous grains in order to obtain high sensitivity and also from the standpoint of preventing pressure marks. In these heterogeneous grains, layers or portions differing in halogen composition may have a clear boundary therebetween or may form a mixed crystal to have a vague boundary therebetween. Further, the structure may be so designed as to have a continuously varying halogen composition.

The silver halide grains in the silver halide emulsions used in the present invention have a mean grain size preferably of from 0.1 to 2 μm, more preferably of from 0.15 to 1.5 μm (the mean grain size is a number average of a diameter of a circle equivalent to a projected area of a grain) with a size distribution having a coefficient of variation (a quotient obtained by dividing a standard deviation by a mean grain size) of not more than 20%, preferably not more than 15% (so-called monodispersed grains). For the purpose of obtaining a broad latitude, two or more different kinds of monodispersed emulsion described above may be blended and coated in the same layer or may be separately coated in different layers.

Silver halide grains contained in photographic emulsions may have a regular crystal form such as a cubic form, an octahedral form or a tetradecahedral form, an irregular crystal form such as a spherical form or a tabular form, a crystal form having a crystal defect, e.g., a twinning plane, or a composite crystal form of these crystal forms.

Silver halide grains usable in the present invention range from fine grains having a grain size not larger than about 0.2 μm to large-sized grains having a projected area diameter of about 10 μm. The silver halide photographic emulsion may be either a monodisperse emulsion or a polydisperse emulsion.

Silver halide photographic emulsions which are usable in the present invention can be prepared by processes described, for example, in Research Disclosure (RD) No. 17643 (Dec. 1978), pp. 22–23, "I. Emulsion Preparation and Types", and ibid., No. 18716 (Nov. 1979), p. 648, P. Glafkides, Chemie et Phisique Photographique, Paul Montel (1967), G. F. Duffin, Photographic Emulsion Chemistry, Focal Press (1966), and V. L. Zelikman et al., Making and Coating Photographic Emulsion, Focal Press (1964).

Monodisperse emulsions described, for example, in U.S. Pat. Nos. 3,574,628 and 3,655,394 and British Patent No. 1,413,748 are also preferably used.

Tabular grains having an aspect ratio of about 3 or more are also usable in the present invention. Such tabular grains can be readily prepared by processes described, for example, in Gutoff, Photographic Science and Engineering, Vol. 14, pp. 248–257 (1970), U.S. Pat. Nos. 4,434,226, 4,414,310, 4,433,048 and 4,439,520, and British Patent No. 2,112,157.

The silver halide grains may be homogeneous grains having a uniform crystal structure throughout the individual grains or heterogeneous grains including those in which the inside and the outer shell have different halogen compositions, those in which the halogen composition differs among layers, and those having silver halides of different halogen composition epitaxially joined together. Silver halide grains joined to compounds other than silver halides, for example, silver rhodanide or lead oxide may also be used. It is also possible to employ a mixture of grains of various crystal forms.

The above-described emulsions may be either a surface latent image type which forms a latent image predominantly on the grain surface or an internal latent image type which forms a latent image predominantly in the inside of the grains, but they must be negative emulsions. A core/shell type internal latent image type emulsion described in Japanese Patent Application Laid-Open (KOKAI) No. 63-264740 (1988) may also be employed. A method of preparing this core/shell type internal latent image type emulsion is described in Japanese Patent Application Laid-Open (KOKAI) No. 59-133542 (1984). The thickness of the shell of this emulsion is preferably in the range of 3 nm to 40 nm, particularly preferably in the range of 5 nm to 20 nm, although it depends on the developing process employed.

The silver halide emulsions are usually used after physical ripening, chemical ripening and spectral sensitization. Additives which are usable in physical ripening, chemical ripening and spectral sensitization of the silver halide emulsion and other known photographic additives which can be used in the present invention are described in Research Disclosure Nos. 17643, 18716 and 30710, as tabulated below.

In the photosensitive material of the present invention, it is possible to use in the same layer a mixture of two or more different kinds of emulsion which are different in at least one of the properties, that is, the grain size of the photosensitive silver halide emulsion, the grain size distribution, the halogen composition, the grain shape, and sensitivity.

It is possible to use silver halide grains fogged at the surface thereof, as described in U.S. Pat. No. 4,082,553, silver halide grains fogged at the inside thereof, as described in U.S. Pat. No. 4,626,498 and Japanese Patent Application Laid-Open (KOKAI) No. 59-214852 (1984), or colloidal silver for a photosensitive silver halide emulsion layer and/or a substantially non-photosensitive hydrophilic colloidal layer. The silver halide grains fogged at the inside or surface thereof enable uniform (non-imagewise) development whether the exposed or unexposed regions of the photosensitive material. A method of preparing silver halide grains fogged at the inside or surface thereof is described in U.S. Pat. No. 4,626,498 and Japanese Patent Application Laid-Open (KOKAI) No. 59-214852 (1984).

The halogen composition of a silver halide, which forms the internal nuclei of core/shell type silver halide grains fogged at the inside thereof, may be the same as or different from that of the silver halide grains. For the silver halide grains fogged at the inside or surface thereof, any of silver chloride, silver chlorobromide, silver iodobromide, and silver chloroiodobromide may be employed. There is no particular restriction on the grain shape of these fogged silver halide grains. However, the mean grain size is preferably in the range of 0.01 μm to 0.75 μm, particularly preferably in the range of 0.05 μm to 0.6 μm. There is no particular restriction on the grain shape, either. The silver halide grains may have a regular crystal form. Further, the silver halide grains may form a polydisperse emulsion, but it is preferable for them to form a monodisperse emulsion (in which at least 95% of the overall weight of the silver halide grains or of the total number of grains have a grain size within ±40% of the mean grain size).

It is preferable in the present invention to use a non-photosensitive fine-grain silver halide. The non-photosensitive fine-grain silver halide comprises silver halide fine grains which are not sensitive to imagewise exposure light for obtaining a dye image and which are not substantially developed in the developing process. It is preferable that the silver halide fine grains should not to be fogged in advance.

The fine-grain silver halide preferably has a silver bromide content in the range of 0 to 100 mol % and may contain silver chloride and/or silver iodide according to need. Preferably, the fine-grain silver halide has a silver iodide content in the range of 0.5 mol % to 10 mol %.

The fine-grain silver halide in the present invention preferably has a mean grain size in the range of 0.01 μm to 0.5 μm, more preferably in the range of 0.02 μm to 0.2 μm (the mean grain size is an average of diameters of circles equivalent to the projected areas of grains).

The fine-grain silver halide can be prepared in the same method as in the case of the ordinary photosensitive silver halide. In this case, the surfaces of the silver halide grains need not be chemically sensitized. No spectral sensitization is needed, either. However, it is preferable to add thereto a known stabilizer, e.g., a triazole, azaindene, benzothiazole or mercapto compound, or a zinc compound, in advance of addition of the silver halide grains to the coating solution. The fine-grain silver halide containing layer can preferably contain colloidal silver.

Known photographic additives which can be used in the present invention are also described in Research Disclosure Nos. 17643, 18716 and 30710, as tabulated below.

| Additives | RD 17643 | RD 18716 | RD 307105 |
|---|---|---|---|
| 1. Chemical sensitizer | p. 23 | p. 648, right column (RC) | p. 866 |
| 2. Sensitivity increasing agent | | p. 648, RC | |
| 3. Spectral sensitizer supersensitizer | pp. 23-24 | p. 648, RC to p. 649, RC | pp. 866-868 |
| 4. Brightening agent | p. 24 | p. 647, RC | p. 868 |
| 5. Antifoggant and stabilizer | pp. 24-25 | p. 649, RC | pp. 868-870 |
| 6. Light absorber, filter dye, ultra-violet absorber | pp. 25-26 | p. 649, RC to p. 650, left column (LC) | p. 873 |
| 7. Stain inhibitor | p. 25, RC | p. 650, LC to RC | p. 872 |
| 8. Dye image stabilizer | p. 25 | p. 650, LC | p. 872 |
| 9. Hardening agent | p. 26 | p. 651, LC | pp. 874-875 |
| 10. Binder | p. 26 | p. 651, LC | pp. 873-874 |
| 11. Plasticizer, lubricant | p. 27 | p. 650, RC | p. 876 |
| 12. Coating aid, surface active agent | pp. 26-27 | p. 650, RC | pp. 875-876 |
| 13. Antistatic agent | p. 27 | p. 650, RC | pp. 876-877 |
| 14. Matting agent | | | pp. 878-879 |

In order to prevent photographic performance deterioration due to contact with formaldehyde gas, the photosensitive material of the present invention preferably contains a compound capable of reacting with formaldehyde to fix it, as described in U.S. Pat. Nos. 4,411,987 and 4,435,503.

It is preferable for the photosensitive material of the present invention to contain a mercapto compound as described in U.S. Pat. Nos. 4,740,454 and 4,788,132, and Japanese Patent Application Laid-Open (KOKAI) Nos. 62-18539 (1987) and 1-283551 (1989).

In addition, it is preferable for the photosensitive material of the present invention to contain a compound which releases a fogging agent, a development accelerator, a silver halide solvent or precursors thereof irrespective of the amount of developed silver, resulting from the developing process, as described in Japanese Patent Application Laid-Open (KOKAI) No. 1-106052 (1989).

In addition, it is preferable for the photosensitive material of the present invention to contain a dye dispersed by a method as described in International Publication No. W088/04794 and Japanese Patent Application Laid-Open (KOKAI) No. 1-502912, or a dye as described in EP No. 317,308A, U.S. Pat. No. 4,420,555 and Japanese Patent Application Laid-Open (KOKAI) No. 1-259358 (1989).

Various color couplers can be used in the photosensitive material of the present invention in combination with the coupler of formula (I) of the present invention. Specific examples of usable color couplers are described in patents cited in Research Disclosure No. 17643, supra, VII-C to G and ibid., No. 307105, VII-C to G.

Examples of suitable yellow couplers are described, for example, in U.S. Pat. Nos. 3,933,501, 4,022,620, 4,326,024, 4,401,752 and 4,248,961, Japanese Patent Application Post-Exam. Publication No. 58-10739 (1983), British Patent Nos. 1,425,020 and 1,476,760, U.S. Pat. Nos. 3,973,968, 4,314,023 and 4,511,649, and European Patent No. 249,473A.

Examples of suitable magenta couplers include 5-pyrazolone couplers and pyrazoloazole couplers. Examples of particularly preferred magenta couplers are described in U.S. Pat. Nos. 4,310,619 and 4,351,897, European Patent No. 73,636, U.S. Pat. Nos. 3,061,432 and 3,725,067, Research Disclosure No. 24220 (Jun. 1984), Japanese Patent Application Laid-Open (KOKAI) No. 60-33552 (1985), Research Disclosure No. 24230 (Jun. 1984), Japanese Patent Application Laid-Open (KOKAI) Nos. 60-43659 (1985), 61-72238 (1986), 60-35730 (1985), 55-118034 (1980) and 60-185951 (1985), U.S. Pat. Nos. 4,500,630, 4,540,654 and 4,556,630, and International Publication No. W088/04795.

As a cyan coupler, phenol and naphthol couplers may be used jointly. Examples of suitable cyan couplers are described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011 and 4,327,173, West German Patent Publication No. 3,329,729, European Patent Nos. 121,365A and 249,453A, U.S. Pat. Nos. 3,446,622, 4,333,999, 4,775,616, 4,451,559, 4,427,767, 4,690,889, 4,254,212 and 4,296,199, and Japanese Patent Application Laid-Open (KOKAI) No. 61-42658 (1986). It is also possible to use jointly pyrazoloazole couplers described in Japanese Patent Application Laid-Open (KOKAI) Nos. 64-553 (1989), 64-554 (1989), 64-555 (1989) and 64-556 (1989), and imidazole couplers described in U.S. Pat. No. 4,818,672.

Typical examples of polymerized dye forming couplers are described, for example, in U.S. Pat. Nos. 3,451,820, 4,080,211, 4,367,282, 4,409,320 and 4,576,910, British Patent No. 2,102,137, and European Patent No. 341,188A.

Examples of preferred couplers which develop a dye having moderate diffusibility are described in U.S. Pat. No. 4,366,237, British Patent No. 2,125,570, European Patent No. 96,570, and West German Patent (OLS) No. 3,234,533.

It is possible to use colored couplers for correcting unnecessary absorption of a developed dye. Preferred examples of such couplers are described in Research Disclosure No. 17643, VII-G, ibid., No. 307105, VII-G, U.S. Pat. No. 4,163,670, Japanese Patent Application Post-Exam Publication No. 57-39413 (1982), U.S. Pat. Nos. 4,004,929 and 4,138,258, and British Patent No. 1,146,368. It is also preferable to use coupler capable of releasing a fluorescent dye upon coupling by which unnecessary absorption of a developed dye is corrected, as described in U.S. Pat. No. 4,774,181, and couplers having a dye precursor group as a releasable group which is capable of reacting with a developing agent to form a dye, as described in U.S. Pat. No. 4,777,120.

Couplers capable of releasing a photographically useful residue on coupling are also usable in the present invention. Examples of preferred DIR couplers which release a development inhibitor are described in patents cited in Research Disclosure No. 17643, VII-F, ibid., No. 307105, VII-F, Japanese Patent Application Laid-Open (KOKAI) Nos. 57-151944 (1982), 57-154234 (1982), 60-184248 (1985), 63-37346 (1988) and 63-37350 (1988), and U.S. Pat. Nos. 4,248,962 and 4,782,012.

Couplers capable of releasing a bleaching accelerator as described in Research Disclosure Nos. 11449 and 24241, and Japanese Patent Application Laid-Open (KOKAI) No. 61-201247 (1986) are effective in shortening the time required for the processing step having bleaching power, particularly when added to a photosensitive material that employs the above-described tabular silver halide grains. Examples of preferred couplers which imagewise release a nucleating agent or a development accelerator at the time of development are described in British Patent Nos. 2,097,140 and 2,131,188, and Japanese Patent Application Laid-Open (KOKAI) Nos. 59-157638 (1984) and 59-170840 (1984). Other compounds preferably used in the present invention include compounds which release a fogging agent, a development accelerator, a silver halide solvent, etc. on a reduction-oxidation reaction with an oxidation product of a color developing agent, as described in Japanese Patent Application Laid-Open (KOKAI) Nos. 60-107029 (1985), 60-252340 (1985), 1-44940 (1989) and 1-45687 (1989).

Other couplers which can be used in the photosensitive material of the present invention include competing couplers as described in U.S. Pat. No. 4,130,427; polyequivalent couplers as described in U.S. Pat. Nos. 4,283,472, 4,338,393 and 4,310,618; a DIR redox compound-releasing coupler, a DIR coupler-releasing coupler, a DIR coupler-releasing redox compound, or a DIR redox-releasing redox compound as described in Japanese Patent Application Laid-Open (KOKAI) Nos. 60-185950 (1985) and 62-24252 (1987); couplers capable of releasing a dye which recolors after release as described in European Patent Nos. 173,302A and 313,308A; couplers capable of releasing a ligand as described in U.S. Pat. No. 4,553,477; couplers capable of releasing a leuco dye as described in Japanese Patent Application Laid-Open (KOKAI) No. 63-75747 (1988); and couplers capable of releasing a fluorescent dye as described in U.S. Pat. No. 4,774,181.

The coupler of formula (I) of the present invention can be introduced into a photosensitive material by various known dispersion methods as described above.

The standard amount of color couplers usable in combination with the coupler of formula (I) of the present invention ranges from 0,001 to 1 mol per mol of photosensitive silver halide. Preferably, yellow couplers are used in an amount of from 0.01 to 0.5 mol; magenta couplers from 0.003 to 0.3 mol; and cyan couplers from 0.002 to 0.3 mol.

The photosensitive material of the present invention may contain a hydroquinone derivative, an aminophenol derivative, a gallic acid derivative, an ascorbic acid derivative, etc. as a color fog inhibitor.

The photosensitive material of the present invention may also contain various discoloration inhibitors. Typical examples of suitable organic discoloration inhibitors for cyan, magenta and/or yellow images include hydroquinones, 6-hydroxychromans, 5-hydroxycoumarans, spirochromans, p-alkoxyphenols, hindered phenols chiefly including bisphenols, gallic acid derivatives, methylenedioxybenzenes, aminophenols, hindered amines, and ether or ester derivatives of these phenol compounds obtained by silylating or alkylating the phenolic hydroxyl group thereof. Metal complexes such as bissalicylaldoximatonickel complexes and bis-N,N-dialkyldithiocarbamatonickel complexes are also usable.

Specific examples of these organic discoloration inhibitors include hydroquinones as described in U.S. Pat. Nos. 2,360,290, 2,418,613, 2,700,453, 2,701,197, 2,728,659, 2,732,300, 2,735,765, 3,982,944 and 4,430,425, British Patent No. 1,363,921, and U.S. Pat. Nos. 2,710,801 and 2,816,028; 6-hydroxychromans, 5-hydroxycoumarans, and spirochromans, as described in U.S. Pat. Nos. 3,432,300, 3,573,050, 3,574,627, 3,698,909 and 3,764,337, and Japanese Patent Application Laid-Open (KOKAI) No. 52-152225 (1977); spiroindanes as described in U.S. Pat. No. 4,360,589; p-alkoxyphenols as described in U.S. Pat. No. 2,735,765, British Patent No. 2,066,975, Japanese Patent Application Laid-Open (KOKAI) No. 59-10539 (1984), and Japanese Patent Application Post-Exam. Publication No. 57-19765 (1982); hindered phenols as described in U.S. Pat. Nos. 3,700,455 and 4,228,235, Japanese Patent Application Laid-Open (KOKAI) No. 52-72224 (1977), and Japanese Patent Application Post-Exam. Publication No. 52-6623 (1977); gallic acid derivatives as described in U.S. Pat. No. 3,457,079; methylenedioxybenzenes as described in U.S. Pat. No. 4,332,886; aminophenols as described in Japanese Patent Application Post-Exam. Publication No. 56-21144 (1981); hindered amines as described in U.S. Pat. Nos. 3,336,135 and 4,268,593, British Patent Nos. 1,326,889, 1,354,313 and 1,410,846, Japanese Patent Application Post-Exam. Publication No. 51-1420 (1976), Japanese Patent Application Laid-Open (KOKAI) Nos. 58-114036 (1983), 59-53846 (1984) and 59-78344 (1984); and metal complexes as described in U.S. Pat. Nos. 4,050,938 and 4,241,155, and British Patent No. 2,027,731(A). These compounds are co-emulsified together with the corresponding color coupler in an amount usually from 5 to 100% by weight based on the coupler and added to a photosensitive layer, thereby attaining the purpose. To prevent fading of a cyan dye image to heat and particularly light, it is more effective to incorporate an ultraviolet absorbent into a cyan-forming layer and two layers adjacent thereto.

Examples of suitable ultraviolet absorbents include benzotriazole compounds having an aryl substituent as described, for example, in U.S. Pat. No. 3,533,794; 4-thiazolidone compounds as described, for example, in U.S. Pat. Nos. 3,314,794 and 31,352,681; benzophenone compounds as described, for example, in Japanese Patent Application Laid-Open (KOKAI) No. 46-2784 (1971); cinnamic ester compounds as described, for example, in U.S. Pat. Nos. 3,705,805 and 3,707,395; butadiene compounds as described, for example, in U.S. Pat. No. 4,045,229; and benzoxazol compounds as described, for example, in U.S. Pat. Nos. 3,406,070 and 4,271,307. Ultraviolet absorbing couplers (e.g., -naphthol type cyan-forming couplers) or ultraviolet absorbing polymers are also usable. These ultraviolet absorbents may be mordanted in a specific layer.

Of these ultraviolet absorbents, benzotriazole compounds having an aryl substituent are preferred.

Binders or protective colloids which are usable in the emulsion layers of the photosensitive material of the present invention include gelatin to an advantage. Other hydrophilic colloids may also be used alone or in combination with gelatin.

Gelatin usable in the present invention may be either lime-processed gelatin or acid-processed gelatin. The details of the preparation of gelatin are described in Arthot Vice, The Macromolecular Chemistry of Gelatin, Academic Press (1964).

The photosensitive material of the present invention preferably contains various antiseptics or antifungal agents, e.g., phenethyl alcohol and those described in Japanese Patent Application Laid-Open (KOKAI) Nos. 63-257747 (1988), 62-272248 (1987) and 1-80941 (1989), such as 1,2-benzisothiazoline-3-one, n-butyl p-hydroxybenzoate, phenol, 4-chloro-3,5-dimethylphenol, 2-phenoxyethanol, and 2-(4-thiazolyl)-benzimidazole.

Direct positive color photosensitive materials according to the present invention can also contain a nucleating agent, such as hydrazine compounds and quaternary heterocyclic compounds, and a nucleation accelerator for enhancing the effect of the nucleating agent as described in Research Disclosure No. 22534 (Jan. 1983).

The present invention is applicable to various color photosensitive materials. Typical examples include ordinary color negative films, color negative films for movies, color reversal films for slides or television, color print papers, color positive films, and color reversal print papers.

Supports which can suitably be used in the present invention are described, for example, in the above-mentioned RD. No 17643, p. 28; RD. No. 18716, from the right-hand column, p. 647, to the left-hand column, p. 648; and RD. No. 307105, p. 879.

Supports which can be generally used in the present invention include a transparent film commonly employed in photographic photosensitive materials, for example, a cellulose nitrate film and a polyethylene terephthalate film, and a reflective support. A reflective support is preferred for accomplishing the object of the present invention.

The terminology "reflective support" as used herein means a support having increased reflecting properties to make a dye image formed in the silver halide emulsion layers more distinct. Such a reflective support includes a support coated with a hydrophobic resin having dispersed therein a light-reflecting substance, e.g., titanium oxide, zinc oxide, calcium carbonate, calcium sulfate, etc.; and a support made from a hydrophobic resin having the above-mentioned light-reflecting substance dispersed therein. Specific examples of suitable reflective supports include baryta paper, polyethylene-coated paper, polypropylene synthetic paper; and a transparent support, e.g., a glass plate, a polyester film (e.g., polyethylene terephthalate, cellulose triacetate, cellulose nitrate), a polyamide film, a polycarbonate film, a polystyrene film, and a vinyl chloride resin film, having thereon a reflective layer or containing therein a reflective substance.

In the photosensitive material of the present invention, the sum total of the film thicknesses of all hydrophilic colloidal layers on the side where an emulsion layer is provided is preferably not larger than 28 μm, more preferably not larger than 23 μm, even more preferably not larger than 18 μm, and particularly preferably not larger than 16 μm. The film swelling speed $T_{\frac{1}{2}}$ is preferably not more than 30 seconds, more preferably not more than 20 seconds. The terminology "film thickness" as used herein means a film thickness measured at 25° C. and a relative humidity of 55% under moisture-conditioned circumstances (2 days). The film swelling speed $T_{\frac{1}{2}}$ can be measured by a means known in the technical field concerned. For example, it can be measured by using a swellometer (oedometer) of the type described in A. Green et al. "Photographic Science and Engineering" Vol. 19, No. 2, pp. 124–129. $T_{\frac{1}{2}}$ is defined as a length of time required to reach ½ of the saturated film thickness, which is defined as 90% of the maximum swell film thickness reached when processing is carried out for 3 minutes and 15 seconds at 30° C. with a color developing solution.

The film swelling speed $T_{\frac{1}{2}}$ can be controlled by adding a hardening agent to gelatin used as a binder, or changing aging conditions after the coating process. The degree of swelling is preferably in the range of 150% to 400%. The degree of swelling can be calculated from the maximum swell film thickness under the above-described conditions according to the expression: (maximum swell film thickness − film thickness)/film thickness.

In the photosensitive material of the present invention, a hydrophilic colloidal layer (hereinafter referred to as "backing layer") in which the sum total of dry film thicknesses is in the range of 2 μm to 20 μm is preferably provided on the side reverse to the side where the emulsion layer is provided. It is preferable for the backing layer to contain the above-described light absorber, filter dye, ultraviolet absorber, antistatic agent, hardening agent, binder, plasticizer, lubricant, coating aid, surface active agent, etc. The degree of swelling of the backing layer is preferably in the range of 150% to 500%.

The color photosensitive material according to the present invention can be developed by any of the conventional methods described in the above-mentioned RD No. 17643, pp. 28–29, RD No. 18716, from the left-hand column to the right-hand column, p. 651, and RD No. 307105, pp. 880–881.

For example, color development processing consists of color development, desilvering, and washing. Reversal development processing consists of black-and-white development, washing or rinsing, reversing, and color development. Desilvering consists of bleach with a bleaching bath and fixing with a fixing bath or, alternatively, bleach-fix with a bleach-fix bath. Bleach, fixing, and bleach-fix may be combined in an arbitrary order. Washing may be replaced with stabilization, or washing may be followed by stabilization. Color development, bleach, and fixing may be carried out in a development-bleach-fix monobath. These processing systems may further be combined with pre-hardening, neutralization after pre-hardening, stop-fixing, after-hardening, compensation, intensification, or a like step. Between two of these steps, an intermediate washing step may be inserted. Color development may be replaced with so-called activator treatment.

A color developing solution which is usable for development processing of the photosensitive material of the present invention is preferably an alkaline aqueous solution containing an aromatic primary amine color developing agent. Useful color developing agents include aminophenol compounds and preferably p-phenylenediamine compounds. Typical examples of p-phenylenediamine compounds are 3-methyl-4-amino-N,N-diethylaniline, 3-methyl-4-amino-N-ethyl-N-β-hydroxyethylaniline, 3-methyl-4-amino-N-ethyl-N-β-methanesulfonamidoethylaniline, 3-methyl-4-amino-N-ethyl-β-methoxyethylaniline, 4-amino-3-methyl-N-methyl-N-(3-hydroxypropyl)aniline, 4-amino-3-methyl-N-ethyl-N-(3-hydroxypropyl)aniline, 4-amino-3-methyl-N-ethyl-N-(2-hydroxypropyl)aniline, 4-amino-3-ethyl-N-ethyl-N-(3-hydroxypropyl)aniline, 4-amino-3-ethyl-N-ethyl-N-(3-hydroxypropyl)aniline, 4-amino-3-methyl-N-propyl-N-(3-hydroxypropyl)aniline, 4-amino-3-propyl-N-methyl-N- (3-hydroxypropyl)aniline, 4-amino-3-methyl-N-methyl-N- (4-hydroxybutyl-)aniline, 4-amino-3-methyl-N-ethyl-N- (4-hydroxybutyl)aniline, 4-amino-3-methyl-N-propyl-N-(4-hydroxybutyl)aniline, 4-amino-3-ethyl-N-ethyl-N-(3-hydroxy-2-methylpropyl)aniline, 4-amino-3-methyl-N,N-bis(4-hydroxybutyl)aniline, 4-amino-3-methyl-N,N-bis(5-hydroxypentyl)aniline, 4-amino-3-methyl-N-(5-hydroxypentyl)-N-(4-hydroxybutyl)aniline, 4-amino-3-methoxy-N-ethyl-N-(4-hydroxybutyl)aniline, 4- amino-3-ethoxy-N,N-bis (5-hydroxypentyl)aniline, 4-amino-3-propyl-N-(4hydroxybutyl)aniline, and salts thereof (e.g., sulfates, hydrochlorides, and p-toluenesulfonates). Among these compounds, 3-methyl-4-amino-N-ethyl-N-β-hydroxyethylaniline, 4-amino-3-methyl-N-ethyl-N-(3-hydroxypropyl)aniline, 4-amino-3-methyl-N-ethyl-N-(4-hydroxybutyl)aniline and salts thereof (e.g., hydrochlorides, p-toluenesulfonates and sulfates) are particularly preferable. These developing agents may be used either individually or in combination of two or more of them according to the desired purpose.

The color developing solution usually contains pH buffering agents, e.g., carbonates, borates or phosphates of alkali metals, and development inhibitors or antifoggants, e.g., chlorides, bromides, iodides, benzimidazoles, benzothiazoles, and mercapto compounds. If desired, the color developing solution further contains various preservatives such as hydroxylamine, diethylhydroxylamine, sulfites, hydrazines (e.g., N,N-b is-carboxymethylhydrazine), phenyl semicarbazides, triethanol amine, and catecholsulfonic acids; organic solvents, e.g., ethylene glycol and diethylene glycol; development accelerators, e.g., benzyl alcohol, polyethylene glycol, quaternary ammonium salts, and amines; dye forming couplers; competing couplers; auxiliary developing agents (e.g., 1-phenyl-3-pyrazolidone); viscosity-imparting agents; and various chelating agents such as aminopolycarboxylic acids, aminopolyphosphonic acids, alkylphosphonic acids, and phosphonocarboxylic acids (e.g., ethylenediaminetetraacetic acid, nitrilotriacetic acid, ethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di(o-hydroxyphenylacetic acid), and salts thereof).

When reversal development is to be carried out, color development is generally effected after black-and-white (hereinafter abbreviated as B/W) development. For the B/W developing solution, it is possible to use known B/W developing agents solely or in combination, for example, dihydroxybenzenes, e.g., hydroquinone, 3-pyrazolidones, e.g., 1-phenyl-3-pyrazolidone, and aminophenols, e.g., N-methyl-p-aminophenol. These color and B/W developing solutions generally have a pH value in the range of 9 to 12. The rate of replenishment of these developing solutions is generally not more than 3 liters per square meter of the photosensitive material, although it depends on the color photographic material to be processed. The rate of replenishment can be reduced to 500 ml or less by lowering the bromide ion concentration in the replenisher. To reduce the rate of replenishment, it is desirable to prevent evaporation and aerial oxidation of a developing solution by minimizing the contact area of the developing solution with air in the processing tank.

The contact area of the photographic processing solution with air in the processing tank may be expressed by the opening ratio, which is defined below:

$$\text{Opening ratio} = [\text{contact area (cm}^2\text{) of processing solution with air}] \div [\text{volume (cm}^3\text{) of processing solution}]$$

The above-described opening ratio is preferably not higher than 0.1 ($cm^{-1}$), more preferably in the range of 0.01 to 0.05. The opening ratio can be reduced by, for example, putting a barrier, such as a floating cover, on the surface of the photographic processing solution in the processing tank. Reduction of the opening ratio may also be achieved by a method that employs a movable cover, as described in Japanese Patent Application Laid-Open (KOKAI) No. 1-82033 (1989), or a slit development processing method as described in Japanese Patent Application Laid-Open (KOKAI) No. 63-216050 (1988). The technique of reducing the opening ratio is preferably applied not only to color development and B/W development but also to all of the subsequent steps, e.g., bleach, bleach-fix, fixing, washing, and stabilization. Reduction of the replenishment rate may also be achieved by using a means for suppressing the accumulation of bromide ions in the developing solution.

The color development processing time is usually from 2 to 5 minutes. The processing time may be shortened by conducting development processing at an elevated temperature and with an increased pH, using a color developing agent at an increased concentration.

The photographic emulsion layers after color development are usually subjected to bleaching. Bleaching and fixing may be carried out either simultaneously (bleach-fix) or separately. For rapid processing, bleaching may be followed by bleach-fix. Further, the mode of bleaching can be arbitrarily selected according to the end use. For example, bleach-fix may be effected using two tanks connected in series, or fixing may be followed by bleach-fix, or bleach-fix may be followed by bleach. Bleaching agents used in a bleaching bath or bleach-fix bath include compounds of polyvalent metals, e.g., iron (III), peracids, quinones, and nitro compounds. Typical bleaching agents include organic complex salts of iron (III), e.g., aminopolycarboxylic acid iron (III) complex salts, such as ethylenediaminetetraacetic acid, diethylenetriaminepentaacetic acid, cyclohexanediaminetetraacetic acid, methyliminodiacetic acid, 1,3-diaminopropanetetraacetic acid, glycol ether diaminetetraacetic acid, etc., and complex salts of citric acid, tartaric acid, malic acid, etc. Among them, aminopolycarboxylic acid iron (III) complex salts including ethylenediaminetetraacetic acid iron (III) complex salt and 1,3-diaminopropanetetraacetic acid iron (III) complex salt are preferred from the viewpoint of speeding up the processing and preventing environmental pollution. Aminopolycarboxylic acid iron (III) complex salts are particularly useful either in a bleaching bath or in a bleach-fix bath. A bleaching bath or bleach-fix bath containing these aminopolycarboxylic acid iron (III) complex salts usually has a pH between 4.0 and 8.0. However, for rapid processing, the pH value may be lowered.

If desired, the bleaching or bleach-fix bath or a prebath therefor may contain known bleaching accelerators. Specific examples of useful bleaching accelerators include compounds having a mercapto group or a disulfide group as described in U.S. Pat. No. 3,893,858, West German Patent Nos. 1,290,812 and 2,059,988, Japanese Patent Application Laid-Open (KOKAI) Nos. 53-32736 (1978), 53-57831 (1978), 53-37418 (1978), 53-72623 (1978), 53-95630 (1978), 53-95631 (1978), 53-104232 (1978), 53-124424 (1978), 53-141623 (1978) and 53-28426 (1978), and Research Disclosure No. 17129 (Jul. 1978); thiazolidine derivatives as described in Japanese Patent Application Laid-Open (KOKAI) No. 50-140129 (1975); thiourea derivatives as described in Japanese Patent Application Post-Exam Publication No. 45-8506 (1970), Japanese Patent Application Laid-Open (KOKAI) Nos. 52-20832 (1977) and 53-32735 (1978), and U.S. Pat. No. 3,706,561; iodides as described in West German Patent No. 1,127,715 and Japanese Patent Application Laid-Open (KOKAI) No. 58-16235 (1983); polyoxyethylene compounds as described in West German Patent Nos. 966,410 and 2,748,430; polyamine compounds as described in Japanese Patent Application Post-Exam Publication No. 45-8836 (1970); compounds as described in Japanese Patent Application Laid-Open (KOKAI) Nos. 49-40943 (1974), 49-59644 (1974), 53-94927 (1978), 54-35727 (1979), 55-26506 (1980) and 58-163940 (1983); and bromide ion. Among them, compounds having a mercapto group or a disulfide group are preferred because of their high accelerating effect. The compounds disclosed in U.S. Pat. No. 3,893,858, West German Patent No. 1,290,812, and Japanese Patent Application Laid-Open (KOKAI) No. 53-95630 (1978) are particularly preferred. In addition, the compounds disclosed in U.S. Pat. No. 4,552,834 are also preferred. These bleaching accelerators may be incorporated into a photosensitive material. The bleaching accelerators are particularly effective for bleach-fix of color photosensitive materials for photography.

For the purpose of preventing bleach stain, the bleaching or bleach-fix bath preferably contains organic acids. Particularly preferred organic acids used for this purpose are those having an acid dissociation constant (pKa) of from 2 to 5, e.g., acetic acid, propionic acid, hydroxyacetic acid, etc.

Fixing agents which can be used in a fixing or bleach-fix bath include thiosulfates, thiocyanates, thioether compounds, thioureas, and a large quantity of iodide. Among them, thiosulfates are commonly used. In particular, ammonium thiosulfate is usable most widely. It is also preferable to use a thiosulfate in combination with a thiocyanate, a thioether compound, a thiourea, etc. Preferred preservatives for the fixing or bleach-fix bath include sulfites, bisulfites, carbonyl-bisulfite adducts, and sulfinic acid compounds described in European Patent No. 294769A. In addition, for the purpose of stabilization, the fixing or bleach-fix bath preferably contains various aminopolycarboxylic acids or organophosphonic acids.

In the present invention, it is preferable for the fixing or bleach-fix bath to contain a compound whose pKa is in the range of from 6.0 to 9.0, preferably an imidazole such as imidazole, 1-methylimidazole, 1-ethylimidazole, 2-methylimidazole, etc., in an amount of from 0.1 mol to 10 mol per liter.

The total time of desilvering is preferably as short as possible as long as sufficient desilvering results. The preferred desilvering time is from 1 to 3 minutes. The desilvering temperature is from 25° C. to 50° C., preferably from 35° C. to 45° C. In the preferable temperature range, the desilvering speed increases, and staining after the processing is effectively prevented.

It is desirable that desilvering be performed while enhancing stirring as much as possible. Methods or means for achieving enhanced stirring include a method in which a jet stream of a processing solution is made to strike against the surface of the emulsion layer of the photosensitive material as described in Japanese Patent Application Laid-Open (KOKAI) No. 62-183460 (1987), a method in which the stirring effect is enhanced by using a rotating means as described in Japanese Patent Application Laid-Open (KOKAI) No. 62-183461 (1987), a method in which the photosensitive material is moved with the emulsion surface kept in contact with a wiper blade provided in the processing solution so as to make the solution turbulent at the emulsion surface, thereby enhancing the stirring effect, and a method in which the overall circulating flow rate of the processing solution is increased. Such a means for enhancing stirring is effective in any of the bleaching, bleach-fix and fixing baths. It is considered that the enhanced stirring accelerates the supply of the bleaching and fixing agents into the emulsion film, resulting in an increase in the desilvering speed. The above-described stirring enhancing means are even more effective when a bleach accelerator is used. That is, it is possible to enhance the acceleration effect remarkably and to eliminate the fixing inhibiting effect of the bleach accelerator.

An automatic processor that is employed for the photosensitive material of the present invention preferably has a photosensitive material transport means as described in Japanese Patent Application Laid-Open (KOKAI) Nos. 60-191257 (1985), 60-191258 (1985) and 60-191259 (1985). As stated in the above-mentioned Japanese Patent Application Laid-Open (KOKAI) No. 60-191257 (1985), such a transport means enables a marked reduction in the amount of processing solution carried from one bath to the subsequent bath and is therefore highly effective in preventing deterioration in the performance of the processing solution. Such effectiveness is particularly useful to shorten the processing time in each step of the processing and to reduce the amount of processing solution replenished.

The silver halide color photosensitive material of the present invention generally undergoes washing and/or stabilizing step after the delivering process. The amount of washing water used in the washing step is selected from a broad range depending on the characteristics of the photosensitive material (e.g., the kind of photosensitive material such as couplers), the end use of the photosensitive material, the temperature of the washing water, the number of washing tanks (the number of stages), the replenishing system (e.g., counter-flow system or direct-flow system), and other various conditions. For example, a relation between the number of washing tanks and the quantity of water in a multi-stage counter-flow system can be decided by the method described in Journal of the Society of Motion Picture and Television Engineers, Vol. 64, pp. 248–253 (May 1955). According to the multi-stage counter-flow system, described in the above-mentioned literature, the amount of water needed for washing can be reduced by a large margin. However, an increase in the residence time of water in the tank causes propagation of bacteria, and the resulting suspended matter may adhere to the photosensitive material. To solve such a problem, a method of reducing calcium and magnesium ions in the washing water, as described in Japanese Patent Application Laid-Open (KOKAI) No. 62-288838 (1987), can be employed extremely effectively for the processing of the color photosensitive material of the present invention. It is also possible to use chlorine germicides, for example, isothiazolone compounds as described in Japanese Patent Application Laid-Open (KOKAI) No. 57-8542 (1982), cyabendazoles, chlorinated sodium isocyanurate, and other germicides, e.g., benzotriazoles, as described in Hiroshi Horiguchi "Chemistry of Antibacterial and Antifungal Agents" (1986), Sankyo Shuppan, "Microbial Sterilization, Pasteurization and Antifungal Techniques" edited by the Society of Hygienic Technology (1982), Kogyo Gijutsu-Kai, and "Encyclopedia of Antibacterial and Antifungal Agents" edited by the Antibacterial and Antifungal Society of Japan (1986).

Washing water used in the processing of the photosensitive material of the present invention has a pH between 4 and 9, preferably between 5 and 8. Washing conditions, although varying depending on the characteristics or the end use of the photosensitive material and the like, are usually from 15° C. to 45° C. in temperature and from 20 seconds to 10 minutes in time, preferably from 25° C. to 40° C. in temperature and from 30 seconds to 5 minutes in time. The photosensitive material of the present invention may also be processed directly with a stabilizing bath without carrying out the above-described washing. In such a stabilizing process, any of the known methods described in Japanese Patent Application Laid-Open (KOKAI) Nos. 57-8543 (1982), 58-14834 (1983) and 60-220345 (1985) can be used.

The above-described washing may be followed by stabilization using, for example, a stabilizing bath containing a dye stabilizer and a surface active agent as a final bath, which is usually used for color photosensitive materials for photography. Examples of usable dye stabilizers include aldehydes such as formalin, glutaraldehyde, etc., N-methylol compounds such as dimethylol urea, N-methylolpyrazole, N-methylol-1,2,4-triazole, etc., azolylmethylamines such as hexamethylenetetramine, 1,4-bis(1,2,4-triazole-1-ylmethyl)piperazine, and aldehyde sulfurous acid additives. This stabilizing bath may contain various chelate and antifungal agents.

Overflow accompanying replenishment for washing and/or stabilization may be reused in other processing steps, for example, in a desilvering step.

When the above-described processing solutions become concentrated by evaporation in the processing that employs an automatic processor or the like, it is preferable to add water for concentration correction.

For the purpose of simplifying and speeding up the processing, the photosensitive material of the present invention may contain a color developing agent, preferably in the form of a precursor thereof. Examples of color developing agent precursors include iodoaniline compounds described in U.S. Pat. No. 3,342,597, Schiff base compounds described in U.S. Pat. No. 3,342,599 and Research Disclosure Nos. 14,850 and 15,159, aldol compounds described in Research Disclosure No. 13,924, metal complex salts described in U.S. Pat. No. 3,719,492, and urethane compounds described in Japanese Patent Application Laid-Open (KOKAI) No. 53-135628 (1978).

If desired, the photosensitive material of the present invention may further contain various 1-phenyl-3-pyrazolidone compounds for the purpose of accelerating color development. Typical examples of these accelerators are described in Japanese Patent Application Laid-Open (KOKAI) Nos. 56-64339 (1981), 57-144547 (1982) and 58-115438 (1983).

Various kinds of processing solution employed in the present invention are used at a temperature of from 10° C. to 50° C.; in a standard manner, from 33° C. to 38° C. Higher processing temperatures may be employed for reducing the processing time, or lower temperatures may be employed for improving the image quality or stability of the processing solution.

The silver halide color photosensitive material of the present invention manifests its effectiveness even more advantageously when it is applied to a film unit with a lens as described, for example, in Japanese Patent Application Post-Exam Publication No. 2-32615 (1990) and Japanese Utility Model Application Post-Exam Publication No. 3-39784 (1991).

DESCRIPTION OF PREFERRED EMBODIMENTS RELATING TO DYE FORMING COUPLERS OF FORMULA (XX) AND (XXI)

The dye forming couplers of formula (XX) and (XXI) of the present invention will be described below in detail.

In formula (XX) or (XXI), EWG represents an electron withdrawing group having a Hammett's $\sigma_p$ value of not less than 0.3.

The "Hammett's $\sigma_p$ value" as used herein is preferably the value reported by Hansch, C. Leo, et al. (see, e.g., J. Med. Chem., Vol. 16, p. 1207 (1973), ibid., Vol. 20, p. 304 (1977), etc.).

Electron withdrawing groups (including atoms) having a Hammett's $\sigma_p$ value of 0.30 or higher include cyano group, nitro group, an aliphatic or aromatic acyl group (e.g., formyl, acetyl, benzoyl, etc.), a carbamoyl group (e.g., carbamoyl, methylcarbamoyl, etc.), a phosphono group, an alkoxycarbonyl group (e.g., methoxycarbonyl, ethoxycarbonyl, diphenylmethylcarbonyl, etc.), a phosphoryl group (e.g., dimethoxyphosphoryl, diphenylphosphoryl, etc.), an aliphatic or aromatic sulfamoyl group (e.g., N-ethylsulfamoyl, N,N-dipropylsulfamoyl, etc.), an aliphatic or aromatic sulfonyl group (e.g., trifluoromethanesulfonyl, difluoromethanesulfonyl, methanesulfonyl, benzenesulfonyl, toluenesulfonyl, etc.), and a perfluoroalkyl group.

More preferable EWGs are a cyano group, an aliphatic or aromatic sulfonyl group, an aliphatic or aromatic acyl group, a carbamoyl group, and an alkoxycarbonyl group. The most preferable EWGs are a cyano group and a carbamoyl group.

$R_1$ and $R_2$ each represent an aliphatic group preferably having from 1 to 36 carbon atoms, an aromatic group preferably having from 6 to 36 carbon atoms (e.g., a phenyl group, a naphthyl group, etc.), a heterocyclic group (e.g., 3-pyridyl, 2-furyl, etc.), an alkoxy group (e.g., methoxy, 2-methoxyethoxy, etc.), an aryloxy group (e.g., 2,4-di-tert-aminophenoxy, 2-chlorophenoxy, 4-cyanophenoxy, etc.), an alkenyloxy group (e.g., 2-propenyloxy), an amino group (e.g., butylamino, dimethylamino, anilino, N-methylanilino, etc.), an acyl group (e.g., acetyl, benzoyl, etc.), an aliphatic or aromatic oxycarbonyl group (e.g., butoxycarbonyl, phenoxycarbonyl, etc.), an acyloxy group (e.g., acetoxy, benzoyloxy, toluenesulfonyloxy, etc.), an aliphatic or aromatic oxysulfonyl (e.g., butoxysulfonyl), an amido group (e.g., acetylamino), a carbamoyl group (e.g., ethylcarbamoyl, dimethylcarbamoyl, etc.), a sulfonamido group (e.g., methanesulfonamido), a sulfamoyl group (e.g., butylsulfamoyl), a sulfamido group (e.g., dipropylsulfamoylamino), an imido group (e.g., succinimido, hydantoinyl, etc.), a ureido group (e.g., phenylureido, dimethylureido, etc.), an aliphatic or aromatic sulfonyl group (e.g., methanesulfonyl, phenylsulfonyl, etc.), an aliphatic or aromatic thio group (e.g., ethylthio, phenylthio, etc.), a hydroxyl group, a cyano group, a carboxyl group, a nitro group, and a sulfo group.

The terminology "aliphatic group" as used herein means a straight chain, branched or cyclic aliphatic hydrocarbon group, including saturated and substituted ones, for example, an alkyl group, an alkenyl group, and an alkynyl group. Typical examples of such aliphatic hydrocarbon groups are methyl, ethyl, butyl, dodecyl, octadecyl, eicosenyl, isopropyl, tert-butyl, tert-octyl, tert-dodecyl, cyclohexyl, cyclopentyl, allyl, vinyl, 2-hexadecenyl, propargyl, dodecyloxy and cyanothyl groups.

$R_1$ and $R_2$ are preferably substituents which are substantially unreleasable on reaction of the coupler with an oxidation product of a developing agent. More preferable examples of $R_1$ are an aliphatic group and an aromatic group. More preferable examples of $R_2$ are an aliphatic group, an aromatic group, a carbamoyl group, an acylamino group, cyano group, a sulfonamido group, an alkoxycarbonyl group, and a perfluoroalkyl group.

X represents a hydrogen atom or a group releasable on reaction of the coupler with an oxidation product of a developing agent (hereinafter referred to as "releasable group").

Specific examples of the releasable group include a halogen atom (e.g., fluorine, chlorine, bromine, etc.), an alkoxy group (e.g., ethoxy, dodecyloxy, methoxyethylcarbamoylmethoxy, carboxypropyloxy, methylsulfonylethoxy, etc.), an aryloxy group (e.g., 4-chlorophenoxy, 4-methoxyphenoxy, 4-carboxyphenoxy, etc.), an acyloxy group (e.g., acetoxy, tetradecanoyloxy, benzoyloxy, etc.), an aliphatic or aromatic sulfonyloxy group (e.g., a methanesulfonyloxy, toluenesulfonyloxy, etc.), an acylamino group (e.g., dichloroacetylamino, heptafluorobutyrylamino, etc.), an aliphatic or aromatic sulfonamido group (e.g., methanesulfonamido, p-toluenesulfonamido, etc.), an alkoxycarbonyloxy group (e.g., ethoxycarbonyloxy, benzyloxycarbonyloxy, etc.), an aryloxycarbonyloxy group (e.g., phenoxycarbonyloxy), an aliphatic, aromatic or heterocyclic thio group (e.g., ethylthio, phenylthio, tetrazolylthio, etc.), a carbamoylamino group (e.g., N-methylcarbamoylamino, N-phenylcarbamoylamino, etc.), a 5- or 6-membered nitrogen-containing heterocyclic group (e.g., imidazolyl, pyrazolyl, triazolyl, 1,2-dihydro-2-oxo-1-pyridyl, etc.), an imido group (e.g., succinimido, hydantoinyl, etc.), an aromatic azo group (e.g., phenylazo), and a carboxyl group, each of which may be substituted with the substituent(s) allowed for $R_1$ and/or $R_2$. Releasable groups bonded via a carbon atom further include bis-form couplers which are obtained by condensation of a four-equivalent coupler by an aldehyde or a ketone. The releasable groups which are usable in the present invention may contain a photographically useful group such as a residue of a development inhibitor or a development accelerator.

The couplers that are represented by formula (XX) or (XXI) may be used in the form of either substantive couplers which are contained in silver halide color photosensitive materials or non-substantive couplers which are contained in color developers. The couplers that are used as substantive couplers preferably have a chemical composition in which at least one of $R_1$, $R_2$, EWG and X in formula (XX) or (XXI) has from 10 to 50 carbon atoms in total.

The couplers of the present invention are effectively used as cyan couplers.

Specific examples of the couplers of formula (XX) and (XXI) according to the present invention will be shown below for illustrative purposes only, but the present invention is not limited to these examples.

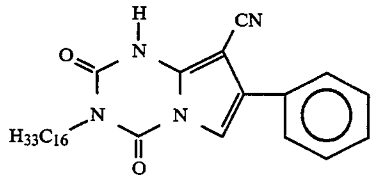

(1)

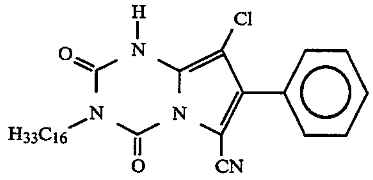

(2)

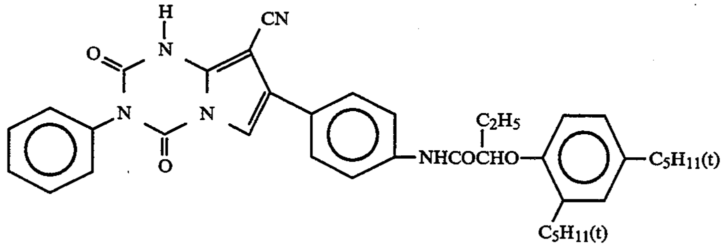

(3)

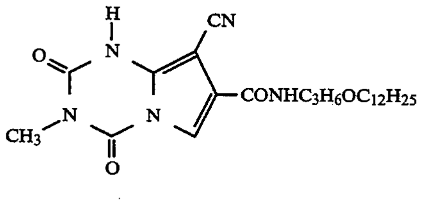

(4)

-continued
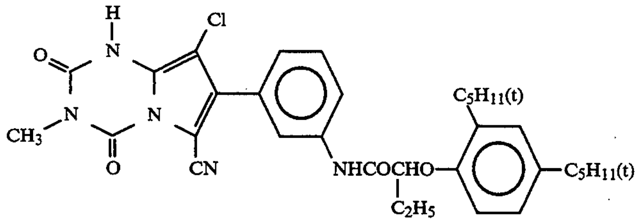
(5)
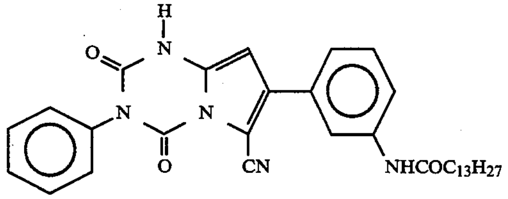
(6)
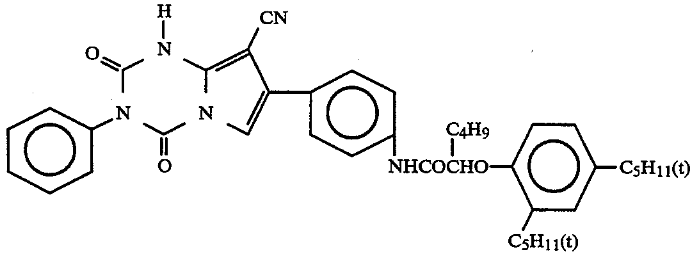
(7)
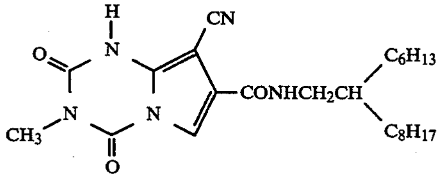
(8)
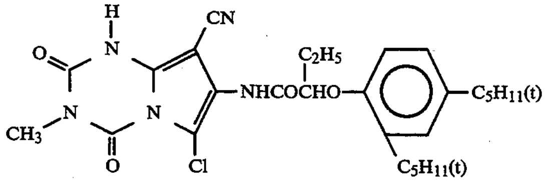
(9)
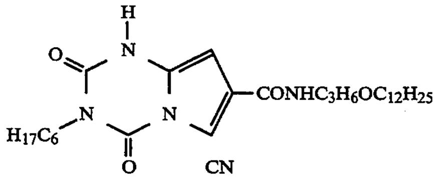
(10)
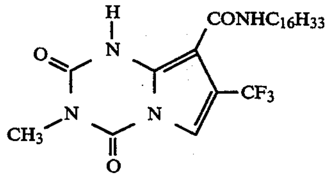
(11)
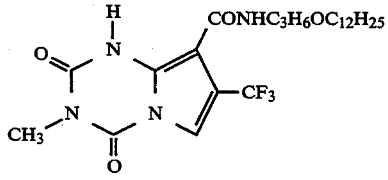
(12)

-continued
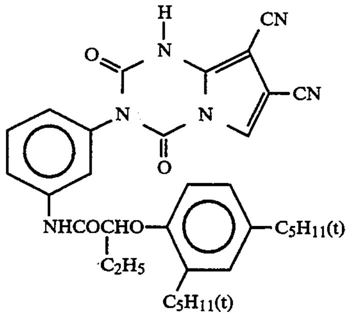
(13)
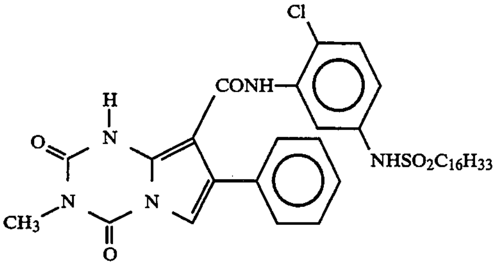
(14)
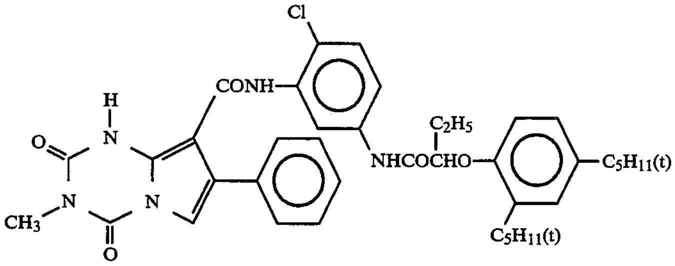
(15)
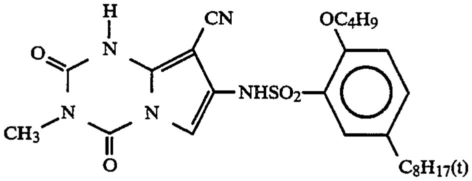
(16)
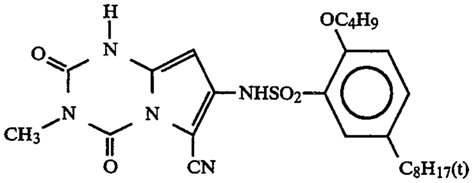
(17)
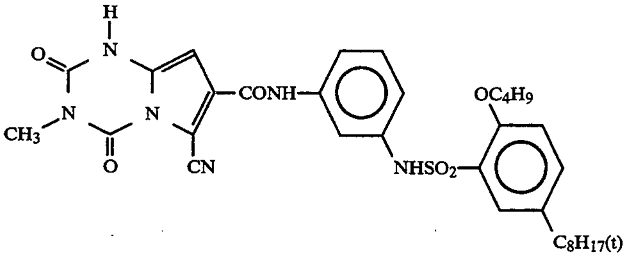
(18)

-continued
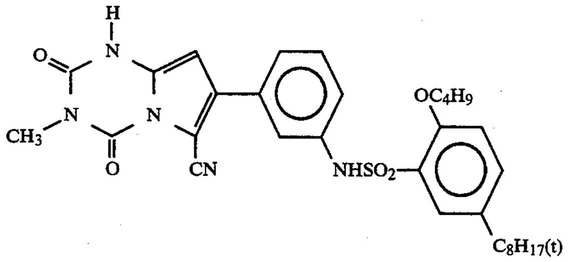
(19)
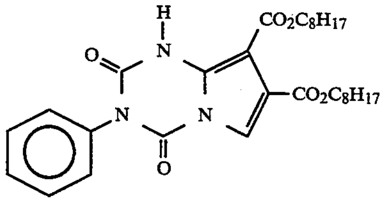
(20)
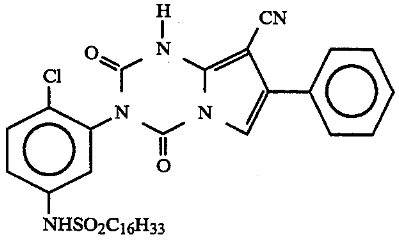
(21)
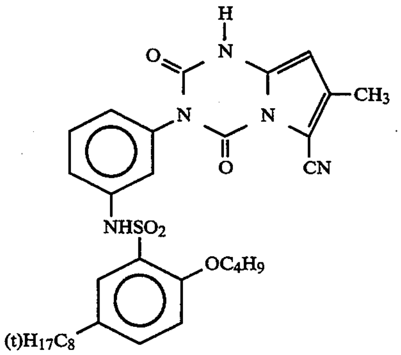
(22)
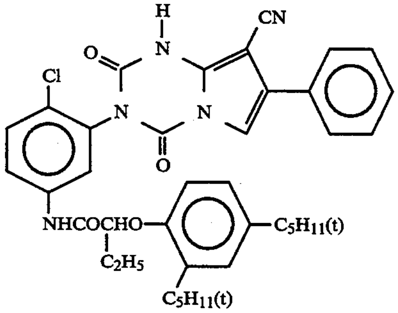
(23)
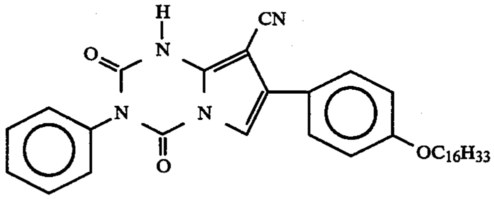
(24)

-continued
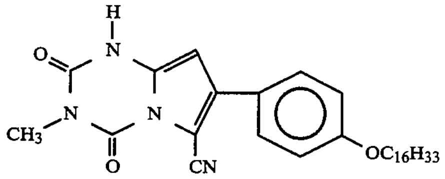
(25)
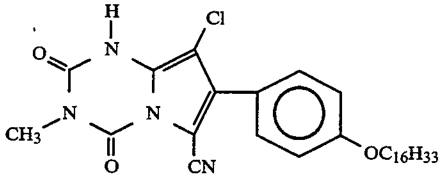
(26)
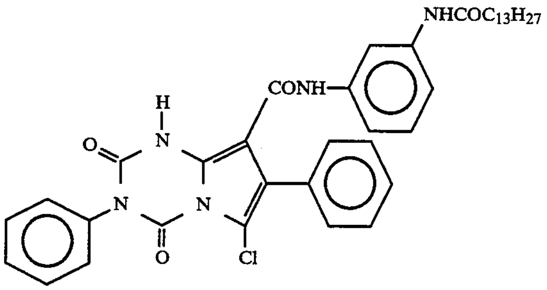
(27)
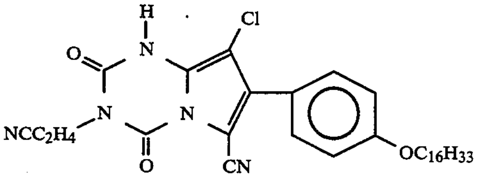
(28)
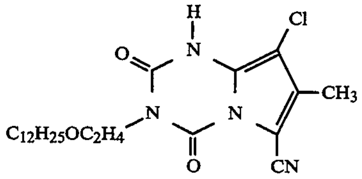
(29)
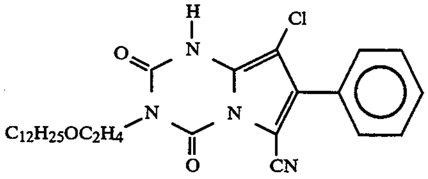
(30)
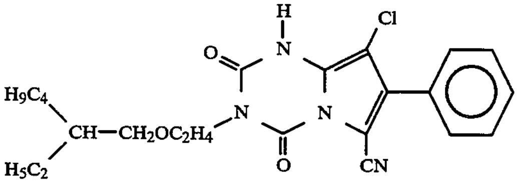
(31)
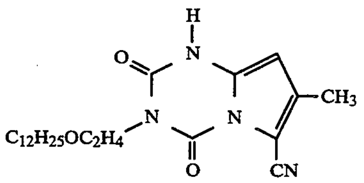
(32)

Table below shows the Hammett's $\sigma_p$ values of the respective substituents EWG in the above-described couplers.

| Couplers | EWG $\sigma_p$ | Couplers | EWG $\sigma_p$ |
|---|---|---|---|
| (1) | 0.66 | (17) | 0.66 |
| (2) | 0.66 | (18) | 0.66 |
| (3) | 0.66 | (19) | 0.66 |
| (4) | 0.66 | (20) | 0.45 |
| (5) | 0.66 | (21) | 0.66 |
| (6) | 0.66 | (22) | 0.66 |
| (7) | 0.66 | (23) | 0.66 |
| (8) | 0.66 | (24) | 0.66 |
| (9) | 0.66 | (25) | 0.66 |
| (10) | 0.66 | (26) | 0.66 |
| (11) | 0.36 | (27) | 0.38 |
| (12) | 0.36 | (28) | 0.66 |
| (13) | 0.66 | (29) | 0.66 |
| (14) | 0.38 | (30) | 0.66 |
| (15) | 0.38 | (31) | 0.66 |
| (16) | 0.66 | (32) | 0.66 |

Synthesis of dye forming couplers of formula (XX) and (XXI) according to the present invention will be described below.

Processes of synthesizing the pyrrolo[1,2-a][1,3,5]triazine-2,4(1H,3H)-dione couplers of the present invention may be roughly divided into two, that is, one in which a 2-aminopyrrole derivative is employed as a starting material, and the other in which a 1,3,5-triazine-2,4(1H,3H)-dione derivative is employed as a starting material. From each of the starting materials, a compound of the present invention can be derived by a method attained by further improving the synthesis procedure disclosed in a reference literature (J. Chem. Soc. Perkin I, 1974, p. 1781-1788).

Specific synthesis examples of the compounds according to the present invention will be shown below.

SYNTHESIS EXAMPLE 4

Synthesis of Compound (1)

Compound (1) was synthesized through the following route:

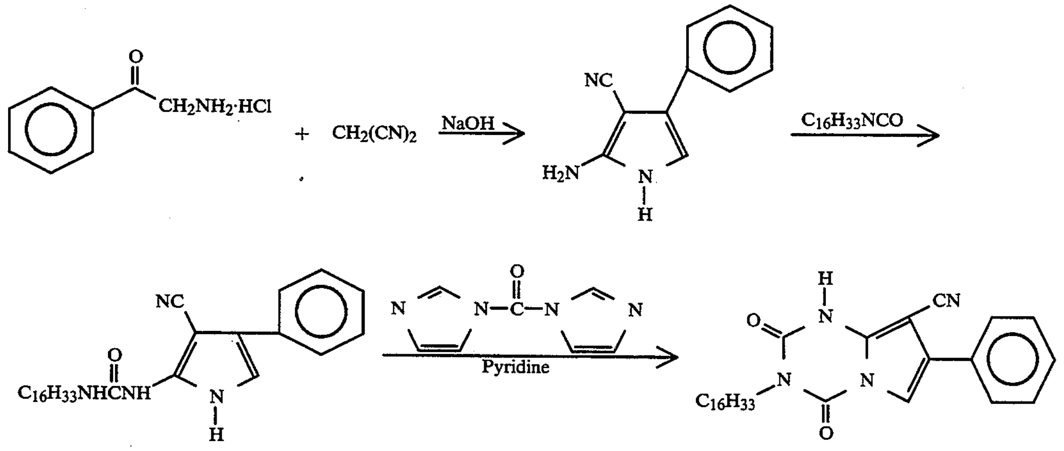

Compound (1)

A solution of 15.4 g of 2-aminoacetophenone in 180 m of a 70% ethanol solution was added dropwise to a mixture of 8 g of malonitrile, 6.6 g of sodium hydroxide and 300 m of a 70% ethanol solution at 60° C., followed by heating for 1 hour at from 70° to 75° C. under stirring. Thereafter, the reaction mixture was allowed to cool and then poured into 600 ml of ice water to form a light gray precipitate, which was collected by filtration, washed with water and dried to obtain 10.4 g of 2-amino-3-cyano-4-phenylpyrrole.

Then, 9.2 g of the pyrrole derivative thus obtained was dissolved in 50 ml of acetonitrile, and 13.4 g of hexadecylisocyanate was added gradually to the resulting solution, followed by stirring at room temperature to form white crystals, which were then collected by filtration to obtain 17.5 g of ureido derivative.

A mixture of 15 g of the above ureido derivative, 16.2 g of carbonyldiimidazole and 50 ml of pyridine was heated under reflux for 10 hours. After being allowed to cool, the reaction mixture was poured into cold diluted hydrochloric acid and then extracted with ethyl acetate. The extract was washed with water and dried. Thereafter, the solvent was removed by vacuum distillation, and the residue was purified by silica gel chromatography (eluate: n-hexane/ethyl acetate=2/1) to obtain 5.8 g (mass spectrum: M+=476) white crystals of compound (1).

SYNTHESIS EXAMPLE 5

Synthesis of Compound (3)

Compound (3) was synthesized through the following route:

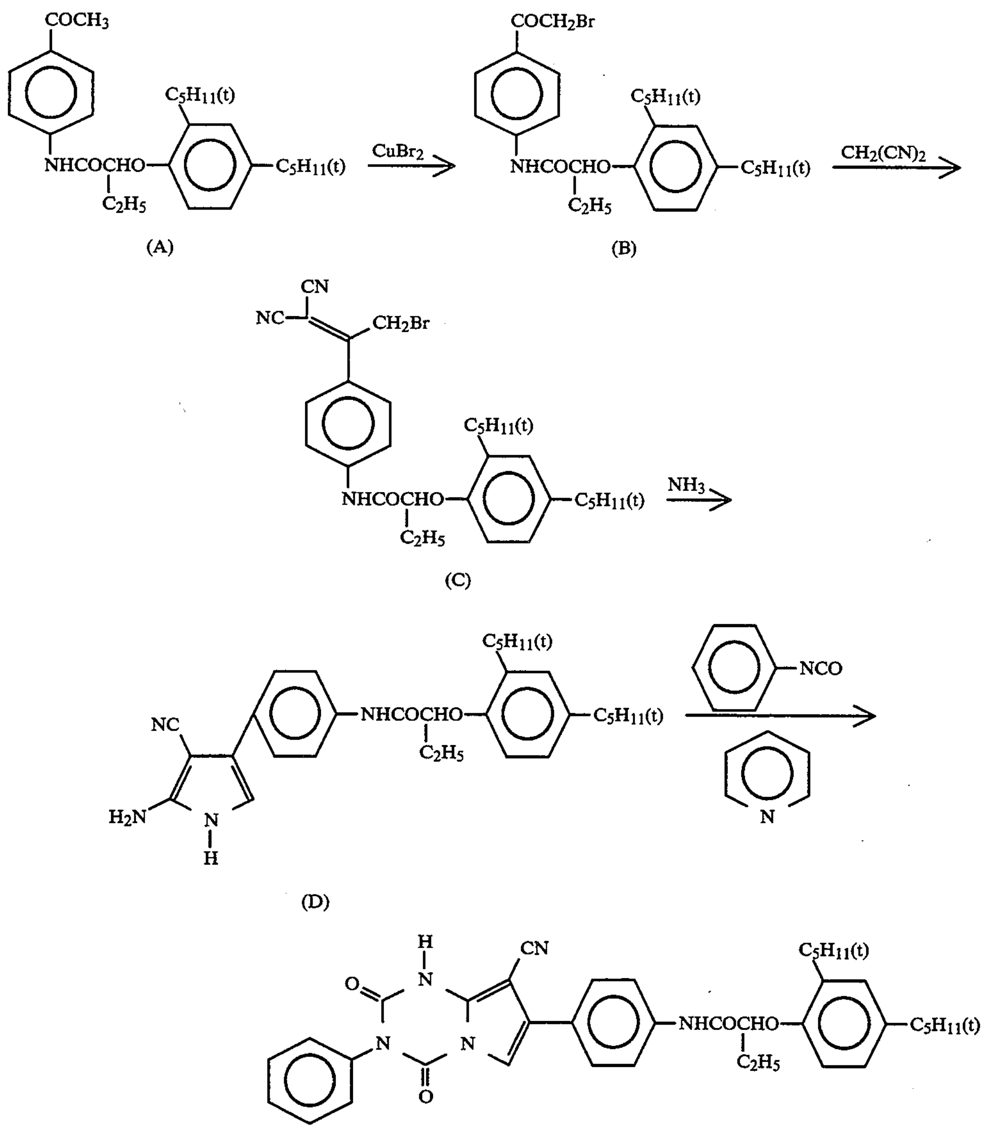

(A) (B) (C) (D)

A mixture of 43.7 g of intermediate compound (A), 34 g of anhydrous cupric bromide and 300 ml of ethyl acetate was heated under reflux for 5 hours under vigorous stirring. After the reaction mixture was allowed to cool, the inorganic matter was separated by filtration, and the solvent was removed from the filtrate by distillation to obtain 48.0 g of crude product from the intermediate compound (B).

Next, the intermediate compound (B) was reacted with malonitrile by a method according to a literature (Chem. Bet., 3571 (1965)) to obtain 36.2 g of an intermediate compound (C). Then, 28.2 g of intermediate compound (C) was added to 300 ml of ethanol saturated with ammonia, and the resulting mixture was heated for 3 hours at 50° to 60° C. After the reaction mixture was allowed to cool, the solvent was removed by distillation, and water and ethyl acetate were added to the residue to separate the organic layer. After washing with water and drying, the ethyl acetate was distilled off to obtain 25.0 g of oily intermediate compound (D).

A mixture of 15.1 g of intermediate compound (D), 11.9 g of phenyl isocyanate and 50 ml of pyridine was heated under reflux for 8 hours. After being allowed to cool, the reaction mixture was poured into cold dilute hydrochloric acid and extracted with ethyl acetate. After washing with water and drying, the solvent was distilled off, and the residue was purified by silica gel chromatography (eluate: n-hexane/ethyl acetate=2/1) to obtain 5.4 g (mass spectrum: M+=645) white crystals of compound (3).

The releasable group may be introduced by the following four different methods depending upon the kind of releasable group.

(1) When the releasable group is a halogen atom

The most common halogen atom is chlorine atom, and such a releasable group can be obtained by chlorinating a four-equivalent coupler containing a hydrogen atom as X with sulfuryl chloride, N-chlorosuccinimide, etc. in a halogeno hydrocarbon solution (e.g., chloroform, methylene chloride, etc.).

(2) When the releasable group is bonded to the coupling position via an oxygen atom (i) In one method, the coupling position of a four-equivalent coupler is halogenated and reacted with a phenol compound in the presence of a base. (ii) In another method, a hydroxyl group at the coupling position of a four-equivalent coupler is reacted with an active halide compound in the presence of a base.

(3) When the releasable group is bonded to the coupling position via a sulfur atom (i) In one method, a four-equivalent coupler and sulfenyl chloride which is to be a releasable group are reacted with each other in the presence or absence of a base. (ii) In another method, a mercapto group is introduced to the coupling position of a four-equivalent coupler so that a halide reacts on this mercapto group.

(4) When the releasable group is bonded to the coupling position via a nitrogen atom (i) In one method, the coupling position of a four-equivalent coupler is nitrosated by a proper nitrosating agent, reduced by a proper method (e.g., a hydrogenation method that uses, for example, Pd-carbon, as a catalyst, or a chemical reduction method that uses stannous chloride) and thereafter allowed to react with one of various halides; (ii) in another method, the coupling position of a four-equivalent coupler is halogenated by a proper halogenating agent (e.g., sulfuryl chloride) and thereafter substituted with a nitrogen heteroring in the presence of a proper basic catalyst according to the method described in Japanese Patent Application Post-Exam. Publication No. 56-45135 (1981); and (iii) in another method, a 6 π or 10 π electronic aromatic nitrogen heteroring is introduced into a halogenated coupler in the presence or absence of an aprotic polar solvent.

The above releasable group introducing methods are described, for example, in U.S. Pat. Nos. 3,894,875, 3,933,501, 4,296,199, 3,227,554, 3,476,563, 4,296,200, 4,234,678, 4,228,233, 4,351,897, 4,264,723, 4,366,237, 3,408,194, 3,725,067, 3,419,391 and 3,926,631, Japanese Patent Application Post-Exam. Publication Nos. 56-45135 (1981) and 57-36577 (1982), and Japanese Patent Application Laid-Open (KOKAI) Nos. 57-70871 (1982), 57-96343 (1982), 53-52423 (1983), 51-105820 (1976), 53-129035 (1978) and 54-48540 (1979).

The coupler of formula (XX) or (XXI)of the present invention forms a dye through a coupling reaction with an oxidation product of an aromatic primary amine developing agent. The cyan dye thus formed may be used for various purposes (e.g., as a filter, a paint, an ink, a dye for image or information recording or printing).

When the coupler of formula (XX)or (XXI)of the present invention is applied to silver halide photosensitive materials, the support of such a photosensitive material has at least one layer containing the coupler of the present invention. Any hydrophilic colloidal layer on the support can contain the coupler of the present invention. General color photosensitive materials can be formed by coating a support with at least one blue-sensitive silver halide emulsion layer, at least one green-sensitive silver halide emulsion layer and at least one red-sensitive silver halide emulsion layer in the mentioned order or any order different therefrom. An infrared-sensitive silver halide emulsion layer may be used in place of at least one of the above-described photosensitive emulsion layers. Each of these photosensitive emulsion layers contains a silver halide emulsion having sensitivity to the corresponding wavelength region and a color coupler capable of forming a dye of a color complementary to the light to which it is sensitive, thereby enabling color reproduction by the subtractive color process. However, the arrangement may also be such that the photosensitive layers and the developed hues of the couplers do not have the above-described relationship.

When the coupler of formula (XX) or (XXI) of the present invention is applied to a color photosensitive material, it is particularly preferable to use it in a red-sensitive silver halide emulsion layer.

The coupler of formula (XX) or (XXI) of the present invention is added to a photosensitive material in an amount of form $1\times10^{-3}$ to 1 mol, preferably from $2\times10^{-3}$ to $3\times101$ mol, per mol of silver halide.

If the coupler of formula (XX) or (XXI) of the present invention is soluble in an alkaline aqueous solution, it may be dissolved in an alkaline aqueous solution together with a developing agent and other necessary additives to form a coupler-in-developer-type color film for formation of a dye image. In such a case, the coupler is used in an amount of from 0.0005 to 0.05 mol, preferably from 0,005 to 0.02 mol, per liter of color developing solution.

The coupler of formula (XX) or (XXI) of the present invention can be introduced into a photosensitive material by various known dispersion methods. It is preferable to employ an oil-in-water dispersion method wherein the coupler is dissolved in a high-boiling organic solvent (together with a low-boiling organic solvent, if necessary), dispersed in an aqueous gelatin solution, and added to a silver halide emulsion.

Examples of high-boiling solvents which are usable in the oil-in-water dispersion method are described, for example, in U.S. Pat. No. 2,322,027. The steps and effects of a latex dispersion method, as one polymer dispersion method, and specific examples of latices for impregnation are described in U.S. Pat. No. 4,199,363, West German Patent Application (OLS) Nos. 2,541,274 and 2,541,230, Japanese Patent Application Post-Exam. Publication No. 53-41091 (1978), and European Patent Publication No. 029104. A dispersion method using an organic solvent-soluble polymer is described in PCT No. W088/00723.

Specific examples of high-boling organic solvents which are usable in the oil-in-water dispersion method are phthalic esters (e.g., dibutyl phthalate, dioctyl phthalate, dicyclohexyl phthalate, di-2-ethylhexyl phthalate, decyl phthalate, bis(2,4-di-tert-amylphenyl) isophthalate, bis(1,1-diethylpropyl) phthalate, etc.), phosphoric or phosphonic esters (e.g., diphenyl phosphate, triphenyl phosphate, tricresyl phosphate, 2-ethylhexyldiphenyl phosphate, dioctylbutyl phosphate, tricyclohexyl phosphate, tri-2-ethylhexyl phosphate, tridodecyl phosphate, di-2-ethylhexylphenyl phosphonate, etc.), benzoic acid esters (e.g., 2-ethylhexyl benzoate, 2,4-dichlorobenzoate, dodecyl benzoate, 2-ethylhexyl-p-hydroxybenzoate, etc.), amides (e.g., N,N-diethyldodecanamide, N,N-diethyllaurylamide, etc.), alcohols or phenols (e.g., isostearyl alcohol, 2,4-di-tert-amylphenol, etc.), aliphatic esters (e.g., dibutoxyethyl succinate, di-2-ethylhexyl succinate, 2-hexyldecyl tetradecanoate, tributyl citrate, diethyl azelate, isostearyl lactate, trioctyl citrate, etc.), aniline derivatives (e.g., N,N-dibutyl-2-butoxy-5-tert-octylaniline), chlorinated paraffins (e.g., paraffins having a chlorine content of from 10 to 80%), trimesic esters (e.g., tributyl trimesate), dodecylbenzene, diisopropylnaphthalene, phenols (e.g., 2,4-di-tert-amylphenol, 4-dodecyloxyphenol, 4-dodecyloxycarbonylphenol, 4-(4-dodecyloxyphenylsulfonyl)phenol, etc.), carboxylic acids (e.g., 2-(2,4-di-tert-amylphenoxybutyric acid, 2-ethoxyoctanedecanoic acid, etc.), and alkylphosphates (e.g., di-(2-ethylhexyl) phosphate, diphenyl phosphate, etc.). Organic solvents having a boiling point of from 30° C. to about 160° C. may be used in combination as an auxiliary solvent. Typical examples of such an auxiliary solvent are ethyl acetate, butyl acetate, ethyl propionate, methyl ethyl ketone, cyclohexanone, 2-ethoxyethyl acetate, and dimethylformamide.

The high-boiling organic solvent is used in an amount of from 0 to 2.0 times, preferably from 0 to 1.0 time, the weight of the coupler.

The couplers of formula (XX) and (XXI) of the present invention are applicable to color papers, color reversal papers, direct positive color photosensitive materials, color negative films, color positive films, color reversal films, etc. Among these uses, it is particularly preferable to apply the couplers to color photosensitive materials having a reflective support (e.g., color papers, color reversal papers, etc.).

Silver halide emulsions which are usable in the present invention may have any halogen composition, for example, silver iodobromide, silver iodochlorobromide, silver bromide, silver chlorobromide, and silver chloride.

A preferred halogen composition depends on the desired type of photosensitive material. For example, a silver chlorobromide emulsion is preferred for use in color papers; a silver iodobromide emulsion having a silver iodide content of from 0.5 to 30 mol % (preferably from 2 to 25 mol %) is preferred in photosensitive materials for photography, such as color negative films and color reversal films; and a silver bromide emulsion or a silver chlorobromide emulsion is preferred in direct positive color photosensitive materials. In photosensitive materials suited for rapid processing, an emulsion having a high silver chloride content (hereinafter referred to as "high silver chloride emulsion) is preferably used. Such a high silver chloride emulsion preferably has a silver chloride content of 90 mol % or more, more preferably 95 mol % or more.

Silver halide grain in the high silver chloride emulsion preferably has localized silver bromide phases in the inside and/or on the surface of the individual grains in layer or non-layer form, as described above. The localized phase preferably has a silver bromide content of at least 10 mol %, more preferably more than 20 mol %. These localized phases may be present in the inside of the grains or on the surface (e.g., edges, corners, or planes) of the grains. One preferred example of such localized phases is an epitaxially grown portion on the corner(s) of grains.

In the present invention, a silver chlorobromide or silver chloride emulsion containing substantially no silver iodide is preferably employed. The expression "containing substantially no silver iodide" as used herein means that the silver iodide content is not more than 1 mol %, more preferably not more than 0.2 mol %.

While the halogen composition of a silver halide emulsion may be either the same or different among individual grains, use of an emulsion having the same halogen composition among grains makes it easy to obtain grains having uniform properties. The halogen composition may be uniformly distributed throughout the individual grains (homogeneous grains), or the individual grains may have a non-uniformly distributed halogen composition to form a laminate structure comprising a core and a single-layered or multi-layered outer shell or may have a non-layered portion differing in halogen composition in the inside or on the surface thereof (when such a portion is on the surface, it is fused on the edge, corner or plane of the grain). Either of the latter two types of grain is preferred to the homogeneous grains in order to obtain high sensitivity and also from the standpoint of preventing pressure marks. In these heterogeneous grains, layers or portions differing in halogen composition may have a clear boundary therebetween or may form a mixed crystal to have a vague boundary therebetween. Further, the structure may be so designed as to have a continuously varying halogen composition.

The silver halide grains in the silver halide emulsions used in the present invention have a mean grain size preferably of from 0.1 to 2 μm, more preferably of from 0.15 to 1.5 μm (the mean grain size is a number average of a diameter of a circle equivalent to a projected area of a grain) with a size distribution having a coefficient of variation (a quotient obtained by dividing a standard deviation by a mean grain size) of not more than 20%, preferably not more than 15% (so-called monodispersed grains). For the purpose of obtaining a broad latitude, two or more different kinds of monodispersed emulsion described above may be blended and coated in the same layer or may be separately coated in different layers.

Silver halide grains contained in photographic emulsions may have a regular crystal form such as a cubic form, a tetradecahedral form or an octahedral form, an irregular crystal form such as a spherical form or a plate form, or a composite crystal form of these crystal forms. Tabular grains can also be used.

Silver halide emulsions which are usable in the present invention may be either a surface latent image type which forms latent image predominantly on the grain surface or an internal latent image type which forms a latent image predominantly in the inside of the grains.

Silver halide photographic emulsions which are usable in the present invention can be prepared by processes described, for example, in Research Disclosure (RD) No. 17643 (Dec. 1978), pp. 22–23, "I. Emulsion Preparation and Types" and ibid , No 18716 (Nov. 1979), p 648, P. Glafkides, Chemie et Phisique Photographique, Paul Montel (1967), G. F. Duffin, Photographic Emulsion Chemistry, Focal Press (1966), and V. L. Zelikman et al., Making and Coating Photographic Emulsion, Focal Press (1964).

Monodispersed emulsions described, for example, in U.S. Pat. Nos. 3,574,628 and 3,655,394 and British Patent No. 1,413,748 are also preferably used.

Tabular grains having an aspect ratio of about 5 or more are also usable in the present invention. Such tabular grains can be readily prepared by processes described, for example, in Gutoff, Photographic Science and Engineering, Vol. 14, pp. 248–257 (1970), U.S. Pat. Nos. 4,434,226, 4,414,310, 4,433,048 and 4,439,520, and British Patent No. 2,112,157.

The silver halide grains may be homogeneous grains having a uniform crystal structure throughout the individual grains or heterogeneous grains including those in which the inside and the outer shell have different halogen compositions, those in which the halogen composition differs among layers, and those having a silver halide of different halogen composition epitaxially joined thereto. Silver halide grains joined to compounds other than silver halides, for example, silver rhodanide or lead oxide may also be used.

It is also possible to employ a mixture of grains of various crystal forms.

In the present invention, these silver halide emulsions are usually used after physical ripening, chemical ripening and spectral sensitization.

During grain formation or physical ripening, various polyvalent metal ion impurities may be introduced into silver halide emulsions used in the present invention. Examples of usable compounds include salts of cadmium, zinc, lead, copper, thallium, etc., and salts or complexes of the group VIII metals, for example, iron, ruthenium, rhodium, palladium, osmium, iridium, and platinum.

Additives which are usable in physical ripening, chemical ripening and spectral sensitization of the silver halide emulsion and other known photographic additives which can be used in the present invention are described in Research Disclosure Nos. 17643, 18716 and 30710, as tabulated below.

| Additives | RD 17643 | RD 18716 | RD 307105 |
|---|---|---|---|
| 1. Chemical sensitizer | p. 23 | p. 648, right column (RC) | p. 866 |
| 2. Sensitivity increasing agent | | p. 648, RC | |
| 3. Spectral sensitizer supersensitizer | pp. 23–24 | p. 648, RC to p. 649, RC | pp. 866–868 |
| 4. Brightening agent | p. 24 | p. 647, RC | p. 868 |
| 5. Antifoggant and stabilizer | pp. 24–25 | p. 649, RC | pp. 868–870 |
| 6. Light absorber, filter dye, ultraviolet absorber | pp. 25–26 | p. 649, RC to p. 650, left column (LC) | p. 873 |
| 7. Stain inhibitor | p. 25, RC | p. 650, LC to RC | p. 872 |
| 8. Dye image stabilizer | p. 25 | p. 650, LC | p. 872 |
| 9. Hardening agent | p. 26 | p. 651, LC | pp. 874–875 |
| 10. Binder | p. 26 | p. 651, LC | pp. 873–874 |
| 11. Plasticizer, lubricant | p. 27 | p. 650, RC | p. 876 |
| 12. Coating aid, surface active agent | pp. 26–27 | p. 650, RC | pp. 875–876 |
| 13. Antistatic agent | p. 27 | p. 650, RC | pp. 876–877 |
| 14. Matting agent | | | pp. 878–879 |

In order to prevent photographic performance deterioration due to contact with formaldehyde gas, the photosensitive material of the present invention may contain a compound capable of reacting with formaldehyde to fix it, as described in U.S. Pat. Nos. 4,411,987 and 4,435,503.

Various color couplers can be used in the photosensitive material of the present invention in combination with the coupler of formula (XX) or (XXI) of the present invention. Specific examples of usable color couplers patents cited in Research Disclosure No. 17643, supra, VII-C to G and ibid., No. 307105, VII-C to G.

Examples of suitable yellow couplers are described, for example, in U.S. Pat. Nos. 3,933,501, 4,022,620, 4,326,024, 4,401,752 and 4,248,961, Japanese Patent Application Post-Exam. Publication No. 58-10739 (1983), British Patent Nos. 1,425,020 and 1,476,760, U.S. Pat. Nos. 3,973,968, 4,314,023 and 4,511,649, and European Patent No. 249,473A.

The coupler of formula (XX) or (X/I) of the present invention is preferably used in combination with yellow couplers which produce a dye having its maximum absorption wavelength in the shorter wavelength region and showing a sharply descending absorption in the longer wavelength region exceeding 500 nm. Examples of such yellow couplers are described, for example, in Japanese Patent Application Laid-Open (KOKAI) Nos. 63-123047 (1988) and 01-173499 (1989).

Examples of suitable magenta couplers include 5-pyrazolone couplers and pyrazoloazole couplers. Examples of particularly preferred magenta couplers are described in U.S. Pat. Nos. 4,310,619 and 4,351,897, European Patent No. 73,636, U.S. Pat. Nos. 3,061,432 and 3,725,067, Research Disclosure No. 24220 (Jun. 1984), Japanese Patent Application Laid-Open (KOKAI) No. 60-33552 (1985), Research Disclosure No. 24230 (Jun. 1984), Japanese Patent Application Laid-Open (KOKAI) Nos. 60-43659 (1985), 61-72238 (1986), 60-35730 (1985), 55-118034 (1980) and 60-185951 (1985), U.S. Pat. Nos. 4,500,630, 4,540,654 and 4,556,630, and International Publication No. W088/04795.

Cyan couplers include phenol couplers and naphthol couplers. Examples of suitable cyan couplers are described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011 and 4,327,173, West German Patent Publication No. 3,329,729, European Patent Nos. 121,365A and 249,453A, U.S. Pat. Nos. 3,446,622, 4,333,999, 4,775,616, 4,451,559, 4,427,767, 4,690,889, 4,254,212 and 4,296,199, and Japanese Patent Application Laid-Open (KOKAI) No. 61-42658 (1986).

It is possible to use colored couplers for correcting unnecessary absorption of a developed dye. Preferred examples of such couplers are described in Research Disclosure No. 17643, VII-G, U.S. Pat. No. 4,163,670, Japanese Patent Application Post-Exam. Publication No. 57-39413 (1982), U.S. Pat. Nos. 4,004,929 and 4,138,258, and British Patent No. 1,146,368. It is also preferable to use coupler capables of releasing a fluorescent dye upon coupling by which unnecessary absorption of a developed dye is corrected, as described in U.S. Pat. No. 4,774,181, and couplers having a dye precursor group as a releasable group which is capable of reacting with a developing agent to form a dye, as described in U.S. Pat. No. 4,777,120.

Examples of preferred couplers which develop a dye having moderate diffusibility are described in U.S. Pat. No. 4,366,237, British Patent No. 2,125,570, European Patent No. 96,570, and West German Patent (OLS) No. 3,234,533.

Typical examples of polymerized dye forming couplers are described, for example, in U.S. Pat. Nos. 3,451,820, 4,080,211, 4,367,282, 4,409,320 and 4,576,910, and British Patent No. 2,102,173.

Couplers capable of releasing a photographically useful residue on coupling are also usable in the present invention. Examples of preferred DIR couplers which release a development inhibitor are described in patents cited in Research Disclosure No. 17643, VII-F, Japanese Patent Application Laid-Open (KOKAI) Nos. 57-151944 (1982), 57-154234 (1982), 60-184248 (1985) and 63-37346 (1988), and U.S. Pat. Nos. 4,248,962 and 4,782,012.

Examples of preferred couplers which imagewise release a nucleating agent or a development accelerator at the time of development are described in British Patent Nos. 2,097,140 and 2,131,188, and Japanese Patent Application Laid-Open (KOKAI) Nos. 59-157638 (1984) and 59-170840 (1984).

Other couplers which can be jointly used in the photosensitive material of the present invention include competing couplers as described in U.S. Pat. No. 4,130,427; poly-equivalent couplers as described in U.S.

Pat. Nos. 4,283,472, 4,338,393 and 4,310,618; couplers capable of releasing a DIR redox compound, a DIR coupler-releasing redox compound, or a DIR redox-releasing redox compound as described in Japanese Patent Application Laid-Open (KOKAI) Nos. 60-185950 (1985) and 62-24252 (1987); couplers capable of releasing a dye which restores its color after release as described in European Patent No. 173,302A; couplers capable of releasing a bleaching accelerator as described in Research Disclosure Nos. 11449 and 24241, and Japanese Patent Application Laid-Open (KOKAI) No. 61-201247 (1986); couplers capable of releasing a ligand as described in U.S. Pat. No. 4,553,477; couplers capable of releasing a leuco dye as described in Japanese Patent Application Laid-Open (KOKAI) No. 63-75747 (1988); and couplers capable of releasing a fluorescent dye as described in U.S. Pat. No. 4,774,181.

The standard amount of color couplers usable in combination with the couplers of the present invention ranges from 0,001 to 1 mol per mol of photosensitive silver halide. Preferably, yellow couplers are used in an amount of from 0.01 to 0.5 mol; magnet couplers from 0.003 to 0.3 mol; and cyan couplers from 0.002 to 0.3 mol.

These couplers usable in combination can be introduced into a photosensitive material by the above-described various known dispersion methods.

The photosensitive material of the present invention may contain a hydroquinone derivative, an aminophenol derivative, a gallic acid derivative, an ascorbic acid derivative, etc. as a color fog inhibitor.

The photosensitive material of the present invention may also contain various discoloration inhibitors. Typical examples of suitable organic discoloration inhibitors for cyan, magenta and/or yellow images include hydroquinones, 6-hydroxychromans, 5-hydroxycoumarans, spirochromans, p-alkoxyphenols, hindered phenols chiefly including bisphenols, gallic acid derivatives, methylenedioxybenzenes, aminophenols, hindered amines, and ether or ester derivatives of these phenol compounds obtained by silylating or alkylating the phenolic hydroxyl group thereof. Metal complexes such as bissalicylaldoximatonickel complexes and bis-N,N-dialkyldithiocarbamatonickel complexes are also usable.

Specific examples of these organic discoloration inhibitors include hydroquinones as described in U.S. Pat. Nos. 2,360,290, 2,418,613, 2,700,453, 2,701,197, 2,728,659, 2,732,300, 2,735,765, 3,982,944 and 4,430,425, British Patent No. 1,363,921, and U.S. Pat. Nos. 2,710,801 and 2,816,028; 6-hydroxychromans, 5-hydroxycoumarans, and spirochromans, as described in U.S. Pat. Nos. 3,432,300, 3,573,050, 3,574,627, 3,698,909 and 3,764,337, and Japanese Patent Application Laid-Open (KOKAI) No. 52-152225 (1977); spiroindanes as described in U.S. Pat. No. 4,360,589; p-alkoxyphenols as described in U.S. Pat. No. 2,735,765, British Patent No. 2,066,975, Japanese Patent Application Laid-Open (KOKAI) No. 59-10539 (1984), and Japanese Patent Application Post-Exam. Publication No. 57-19765 (1982); hindered phenols as described in U.S. Pat. Nos. 3,700,455 and 4,228,235, Japanese Patent Application Laid-Open (KOKAI) No. 52-72224 (1977), and Japanese Patent Application Post-Exam. Publication No. 52-6623 (1977); gallic acid derivatives as described in U.S. Pat. No. 3,457,079; methylenedioxybenzenes as described in U.S. Pat. No. 4,332,886; aminophenols as described in Japanese Patent Application Post-Exam. Publication No. 56-21144 (1981); hindered amines as described in U.S. Pat. Nos. 3,336,135 and 4,268,593, British Patent Nos. 1,326,889, 1,354,313 and 1,410,846, Japanese Patent Application Post-Exam. Publication No. 51-1420 (1976), Japanese Patent Application Laid-Open (KOKAI) Nos. 58-114036 (1983), 59-53846 (1984) and 59-78344 (1984); and metal complexes as described in U.S. Pat. Nos. 4,050,938 and 4,241,155, and British Patent No. 2,027,731(A). These compounds are co-emulsified together with the corresponding color coupler in an amount usually from 5 to 100% by weight based on the coupler and added to a photosensitive layer, thereby attaining the purpose. To prevent fading of a cyan dye image to heat and particularly light, it is more effective to incorporate an ultraviolet absorbent into a cyan-forming layer and two layers adjacent thereto.

Examples of suitable ultraviolet absorbents include benzotriazole compounds having an aryl substituent as described, for example, in U.S. Pat. No. 3,533,794; 4-thiazolidone compounds as described, for example, in U.S. Pat. Nos. 3,314,794 and 3,352,681; benzophenone compounds as described, for example, in Japanese Patent Application Laid-Open (KOKAI) No. 46-2784 (1971); cinnamic ester compounds as described, for example, in U.S. Pat. Nos. 3,705,805 and 3,707,395; butadiene compounds as described, for example, in U.S. Pat. No. 4,045,229; and benzoxazol compounds as described, for example, in U.S. Pat. Nos. 3,406,070 and 4,271,307. Ultraviolet absorbing couplers (e.g., $\alpha$-naphthol type cyan-forming couplers) or ultraviolet absorbing polymers are also usable. These ultraviolet absorbents may be mordanted in a specific layer.

Of these ultraviolet absorbents, benzotriazole compounds having an aryl substituent are preferred.

Binders or protective colloids which are usable in the emulsion layers of the photosensitive material of the present invention include gelatin to an advantage. Other hydrophilic colloids may also be used alone or in combination with gelatin.

Gelatin usable in the present invention may be either lime-processed gelatin or acid-processed gelatin. The details of the preparation of gelatin are described in Arthot Vice, The Macromolecular Chemistry of Gelatin, Academic Press (1964).

The photosensitive material of the present invention preferably contains various antiseptics or antifungal agents as described in Japanese Patent Application Laid-Open (KOKAI) Nos. 63-257747 (1988), 62-272248 (1987) and 01-80941 (1989), such as 1,2-benzisothiazolin-3-one, n-butyl p-hydroxybenzoate, phenol, 4-chloro-3,5-dimethylphenol, 2-phenoxyethanol, and 2-(4-thiazolyl)-benzimidazole.

Direct positive color photosensitive materials according to the present invention can also contain a nucleating agent, such as hydrazine compounds and quaternary heterocyclic compounds, and a nucleation accelerator for enhancing the effect of the nucleating agent as described in Research Disclosure No. 22534 (Jan. 1983).

Supports which can be generally used in the present invention include a transparent film commonly employed in photographic photosensitive materials, for example, a cellulose nitrate film and a polyethylene terephthalate film, and a reflective support. A reflective support is preferred for accomplishing the object of the present invention.

The terminology "reflective support" as used herein means a support having increased reflecting properties to make a dye image formed in the silver halide emulsion layers more distinct. Such a reflective support includes a support coated with a hydrophobic resin having dispersed therein a light-reflecting substance, e.g., titanium oxide, zinc oxide, calcium carbonate, calcium sulfate, etc.; and a support made from a hydrophobic resin having the above-mentioned light-reflecting substance dispersed therein. Specific examples of suitable reflective supports include baryta paper, polyethylene-coated paper, polypropylene synthetic paper; and a transparent support, e.g., a glass plate, a polyester film (e.g., polyethylene terephthalate, cellulose triacetate, cellulose nitrate), a polyamide film, a polycarbonate film, a polystyrene film, and a vinyl chloride resin film, having thereon a reflective layer or containing therein a reflective substance.

The photosensitive materials according to the present invention can be subjected to development processing by a usual method as described in Research Disclosure No. 17643, pp. 28–29 and ibid. No. 18716, p. 615, left to right columns. For example, color development processing consists of color development, desilvering, and washing. Reversal development processing consists of black-and-white development, washing or rinsing, reversing, and color development. Desilvering consists of bleach with a bleaching bath and fixing with a fixing bath or, alternatively, bleach-fix with a bleach-fix bath. Bleach, fixing, and bleach-fix may be combined in an arbitrary order. Washing may be replaced with stabilization, or washing may be followed by stabilization. Color development, bleach, and fixing may be carried out in a development-bleach-fix monobath. These processing systems may further be combined with pre-hardening, neutralization after pre-hardening, stop-fixing, after-hardening, compensation, intensification, or a like step. Between two of these steps, an intermediate washing step may be inserted. Color development may be replaced with so-called activator treatment.

A color developing solution which is usable for development processing of the photosensitive material of the present invention is an alkaline aqueous solution containing an aromatic primary amine color developing agent. Useful color developing agents include aminophenol compounds and preferably p-phenylenediamine compounds. Typical examples of p-phenylenediamine compounds are 3-methyl-4-amino-N,N-diethylaniline, 3-methyl-4-amino-N-ethyl-N-β-hydroxyethylaniline, 4-amino-N-ethyl-N-β-hydroxyethylaniline, 3-methyl-4-amino-N-ethyl-N-β-methanesulfonamidoethylaniline, 3-methyl-4-amino-N-ethyl-N-β-methoxyethylaniline, and salts thereof (e.g., sulfates, hydrochlorides, and p-toluenesulfonates). These developing agents may be used either individually or in combination of two or more of them according to the desired purpose.

The color developing solution usually contains pH buffering agents, e.g., carbonates, borates or phosphates of alkali metals, and development inhibitors or antifoggants, e.g., chlorides, bromides, iodides, benzimidazoles, benzothiazoles, and mercapto compounds. If desired, the color developing solution further contains various preservatives such as hydroxylamine, diethylhydroxylamine, sulfites, hydrazines (e.g., N,N-bis-carboxymethylhydrazine), phenyl semicarbazides, triethanolamine, and catecholsulfonic acids; organic solvents, e.g., ethylene glycol and diethylene glycol; development accelerators, e.g., benzyl alcohol, polyethylene glycol, quarternary ammonium salts, and amines; dye forming couplers; competing couplers; auxiliary developing agents (e.g., 1-phenyl-3-pyrazolidone); nucleating agents, e.g., sodium borohydride and hydrazine compounds; viscosity-imparting agents; various chelating agents such as aminopolycarboxylic acids, aminopolyphosphonic acids, alkylphosphonic acids, and phosphonocarboxylic acids (e.g., ethylenediaminetetraacetic acid, nitrilotriacetic acid, ethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di(o-hydroxyphenylacetic acid), and salts thereof); fluorescent brightening agents, e.g., 4,4'-diamino-2,2'-disulfostilbene compounds; and various surface active agents, e.g., alkylsulfonic acids, arylsulfonic acids, aliphatic carboxylic acids, and aromatic carboxylic acids.

It is preferable that a color developing solution used in the present invention contain substantially no benzyl alcohol. The expression "contain substantially no benzyl alcohol" as used herein means that the benzyl alcohol concentration is preferably not more than 2 ml/l, more preferably not more than 0.5 ml/l, and most preferably zero.

It is also preferable that a color developing solution used in the present invention contain substantially no sulfite ion. The expression "contain substantially no sulfite ion" as used herein means that the sulfite ion concentration is preferably not more than $3.0\times10^{-3}$ mol/l, more preferably zero.

It is also preferable that a color developing solution used in the present invention contain substantially no hydroxylamine. The expression "contain substantially no hydroxylamine" as used herein means that the hydroxylamine concentration is preferably not more than $5.0\times10^{-3}$ mol/l, more preferably zero. The color developing solution used in the present invention preferably contains an organic preservative other than hydroxylamine or sulfite ion, for example, hydroxylamine derivatives or hydrazine derivatives.

The color developing solution generally has a pH between 9 and 12.

Color reversal development processing generally consists of black-and-white (hereinafter abbreviated as B/W) development, washing or rinsing, reversing, and color development. Reversing is carried out by using a reversing bath containing a fogging agent or by reversal exposure. The reversing step may be omitted by incorporating a fogging agent into a color developing solution.

A B/W developing solution used for B/W development is a B/W developing solution usually known for processing of B/W photosensitive materials, which contains various known additives.

Typical additives include B/W developing agents, e.g., 1-phenyl-3-pyrazolidone, N-methyl-p-aminophenol, and hydroquinone; preservatives, e.g., sulfites; pH buffering agents comprising a water-soluble acid, e.g., acetic acid and boric acid; pH buffering agents or development accelerators comprising an alkali, e.g., sodium hydroxide, sodium carbonate and potassium carbonate; organic or inorganic development inhibitors, e.g., potassium bromide, 2-methylbenzimidazole, and methylbenzothiazole; water softeners, e.g., ethylenediaminetetraacetic acid and polyphosphoric acid salts; antioxidants, e.g., ascorbic acid and diethanolamine;

organic solvents, e.g., triethylene glycol and cellosolve; and surface overdevelopment inhibitors, e.g., a trace amount of iodides, and mercapto compounds.

To reduce the rate of replenishment of these developing solutions, it is desirable to prevent evaporation and aerial oxidation of a developing solution by minimizing the contact area of the developing solution with air. The contact area between a developing solution and air can be minimized by, for example, putting a barrier, such as a floating cover, on the liquid surface. This technique is preferably applied not only to color development and B/W development but also to all of the subsequent steps. Reduction of the replenishment rate may also be achieved by using a means for suppressing the accumulation of bromide ions in the developing solution.

The color development processing time is usually from 2 to 5 minutes. The processing time may be shortened by conducting development processing at an elevated temperature and with an increased pH, using a color developing agent at an increased concentration.

The photographic emulsion layers after color development are usually subjected to desilvering process consisting of bleach and fixing. Bleach and fixing may be carried out either simultaneously (bleach-fix) or separately. For rapid processing, bleach may be followed by bleach-fix. Further, the mode of desilvering can be arbitrarily selected according to the end use. For example, bleach-fix may be effected using two tanks connected in series, or fixing may be followed by bleach-fix, or bleach-fix may be followed by bleach. The advantageous effects of the present invention are effectively manifested by conducting bleach-fix immediately after color development.

Bleaching agents used in a bleaching bath or bleach-fix bath include compounds of polyvalent metals, e.g., iron (III), peracids, quinones, and iron salts. Typical bleaching agents include iron chloride, ferricyanides, bichromates, organic complex salts of iron (III), e.g., complex salts with aminopolycarboxylic acids (e.g., ethylenediaminetetraacetic acid, diethylenetriaminepentaacetic acid, 1,3-diaminopropanoltetraacetic acid, etc.), and persulfates. Among them, aminopolycarboxylic acid iron (III) complexes are preferred from the viewpoint of effectively manifesting the advantageous effects of the present invention. Aminopolycarboxylic acid iron (III) complex salts are particularly useful either in a bleaching bath or in a bleach-fix monobath. A bleaching bath or bleach-fix bath containing these aminopolycarboxylic acid iron (III) complex salts usually has a pH between 3.0 and 8.0.

The fixing bath or bleach-fix bath may contain known additives such as re-halogenating agents, e.g., ammonium bromide and ammonium chloride, pH buffering agents, e.g., ammonium nitrate, and metal corrosion inhibitors, e.g., ammonium sulfate.

For the purpose of preventing bleach stain, the bleaching or bleach-fix bath preferably contains organic acids. Particularly preferred organic acids used for this purpose are those having an acid dissociation constant (pKa) of from 2 to 5.5, e.g., acetic acid and propionic acid.

Fixing agents which can be used in a fixing or bleach-fix bath include thiosulfates, thiocyanates, thioether compounds, thioureas, and a large quantity of iodide. Among them, thiosulfates are commonly used. In particular, ammonium thiosulfate is usable most widely. It is also preferable to use a thiosulfate in combination with a thiocyanate, a thioether compound, a thiourea, etc.

Preferred preservatives for the fixing or bleach-fix bath include sulfites, bisulfites, carbonyl-bisulfite adducts, and sulfinic acid compounds described in European Patent No. 294769A. In addition, for the purpose of stabilization, the fixing or bleach-fix bath preferably contains various aminopolycarboxylic acids or organophosphonic acids, e.g., 1-hydroxyethylidene-1,1-diphosphonic acid and N,N,N',N'-ethylenediaminetetraphosphonic acid.

The fixing or bleach-fix bath can also contain various fluorescent brightening agents, defoaming agents, surface active agents, polyvinyl pyrrolidone, methanol, etc.

If desired, the bleaching or bleach-fix bath or a prebath therefor may contain known bleaching accelerators. Specific examples of useful bleaching accelerators include compounds having a mercapto group or a disulfide group as described in U.S. Pat. No. 3,893,858, West German Patent Nos. 1,290,812 and 2,059,988, Japanese Patent Application Laid-Open (KOKAI) Nos. 53-32736 (1978), 53-57831 (1978), 53-37418 (1978), 53-72623 (1978), 53-95630 (1978), 53-95631 (1978), 53-104232 (1978), 53-124424 (1978), 53-141623 (1978) and 53-28426 (1978), and Research Disclosure No. 17129 (Jul. 1978); thiazolidine derivatives as described in Japanese Patent Application Laid-Open (KOKAI) No. 50-140129 (1975); thiourea derivatives as described in Japanese Patent Application Post-Exam. Publication No. 45-8506 (1970), Japanese Patent Application Laid-Open (KOKAI) Nos. 52-20832 (1977) and 53-32735 (1978), and U.S. Pat. No. 3,706,561; iodides as described in West German Patent No. 1,127,715 and Japanese Patent Application Laid-Open (KOKAI) No. 58-16235 (1983); polyoxyethylene compounds as described in West German Patent Nos. 966,410 and 2,748,430; polyamine compounds as described in Japanese Patent Application Post-Exam. Publication No. 45-8836 (1970); compounds as described in Japanese Patent Application Laid-Open (KOKAI) Nos. 49-42434 (1974), 49-59644 (1974), 53-94927 (1978), 54-35727 (1979), 55-26506 (1980) and 58-163940 (1983); and bromide ion. Among them, compounds having a mercapto group or a disulfide group are preferred because of their high accelerating effect. The compounds disclosed in U.S. Pat. No. 3,893,858, West German Patent No. 1,290,812, and Japanese Patent Application Laid-Open (KOKAI) No. 53-95630 (1978) are particularly preferred. In addition, the compounds disclosed in U.S. Pat. No. 4,552,834 are also preferred. These bleaching accelerators may be incorporated into a photosensitive material. The bleaching accelerators are particularly effective for bleach-fix of color photosensitive materials for photography.

The total time of desilvering is preferably as short as possible as long as sufficient desilvering results. The preferred desilvering time is from 1 to 3 minutes. The desilvering temperature is from 25° to 50° C. preferably from 35° to 45° C.

It is desirable that desilvering be performed while enhancing stirring as much as possible. Methods or means for achieving enhanced stirring include a method in which a jet stream of a processing solution is made to strike against the surface of the emulsion layer of the photosensitive material as described in Japanese Patent Application Laid-Open (KOKAI) No. 62-183460 (1987). Such a stirring means is effective in any of the bleaching, bleach-fix and fixing baths.

After desilvering, the photosensitive material of the present invention is generally subjected to washing. Washing may be replaced with stabilization. In such stabilization processing, any of the known stabilizing techniques described, for example, in Japanese Patent Application Laid-Open (KOKAI) Nos. 57-8543 (1982), 58-14834 (1983) and 60-20345 (1985) can be utilized. Washing may be followed by stabilization using a stabilizing bath containing a dye stabilizer and a surface active agent as a final bath, which is usually used for color photosensitive materials for photography.

Washing water or a stabilizing bath may contain water softeners, e.g., inorganic phosphoric acids, polyaminocarboxylic acids, and organic aminophosphonic acids; bactericides, e.g., isothiazolone compounds and thiabendazole compounds; chlorine type bactericides, e.g., chlorinated sodium isocyanurate; metal salts, e.g., magnesium salts, aluminum salts, and bismuth salts; surface active agents; and hardening agents.

The amount of washing water used in the washing step is selected from a broad range depending on the characteristics of the photosensitive material (e.g., the kind of photosensitive material such as couplers), the end use of the photosensitive material, the temperature of the washing water, the number of washing tanks (the number of stages), the replenishing system (e.g., counter-flow system or direct-flow system), and other various conditions. For example, a relation between the number of washing tanks and the quantity of water in a multi-stage counter-flow system can be decided by the method described in Journal of the Society of Motion Picture and Television Engineers, Vol. 64, pp. 248–253 (May 1955). In addition, a method of reducing calcium and magnesium ions in the washing water as described in Japanese Patent Application Laid-Open (KOKAI) No. 62-288838 (1987) can be employed extremely effectively.

Washing water usually has a pH between 4 and 9, preferably between 5 and 8. Washing conditions, although varying depending on the characteristics or the end use of the photosensitive material and the like, are usually from 15° to 45° C. in temperature and from 20 seconds to 10 minutes in time, preferably from 25° to 40° C. in temperature and from 30 seconds to 5 minutes in time.

Dye stabilizers which can be used in the stabilizing bath include aldehydes (e.g., formalin and glutaraldehyde), N-methylol compounds (e.g., dimethylolurea), hexamethylenetetramine, and an aldehyde-sulfite adduct. If desired, the stabilizing bath may also contain pH buffering agents (e.g., boric acid, sodium hydroxide), chelating agents (e.g., 1-hydroxyethylidene-1,1-diphosphonic acid, ethylene-diaminetetraacetic acid), sulfiding inhibitors (e.g., alkanolamines), fluorescent brightening agents, and antifungal agents.

Overflow accompanying replenishment for washing and/or stabilization may be reused in other processing steps, for example, in a desilvering step.

For the purpose of simplifying and speeding up the processing, the photosensitive material of the present invention may contain a color developing agent, preferably in the form of a precursor thereof. Examples of color developing agent precursors include iodoaniline compounds described in U.S. Pat. No. 3,342,597, Schiff base compounds described in U.S. Pat. No. 3,342,597 and Research Disclosure Nos. 14,850 and 15,159, aldol compounds described in Research Disclosure No. 13,924, metal complex salts described in U.S. Pat. No. 3,719,492, and urethane compounds described in Japanese Patent Application Laid-Open (KOKAI) No. 53-135628 (1978).

If desired, the photosensitive material of the present invention may further contain various 1-phenyl-3-pyrazolidone compounds for the purpose of accelerating color development. Typical examples of these accelerators are described in Japanese Patent Application Laid-Open (KOKAI) Nos. 56-64339 (1981), 57-144547 (1982) and 58-115438 (1983).

Various kinds of processing solution employed in the present invention are used at a temperature of from 10° C. to 50° C.; in a standard manner, from 33° C. to 38° C. Higher processing temperatures may be employed for reducing the processing time, or lower temperatures may be employed for improving the image quality or stability of the processing solution.

The present invention will be described below in detail by way of Examples, but it should be understood that the present invention is not necessarily limited thereto.

EXAMPLE 1

Cyan dyes (A), (B), (C) and (E) were synthesized by using couplers (III)-1 and (II)-1 of the present invention, a comparative coupler (C-1) and (C-2), and a developing agent (D), and reduction potential was measured. A THF solution of each dye and Britton-Robinson buffer solution were mixed in a volume ratio of 3:2 to prepare a solution having a dye concentration of $1\times10^{-4}$ mol/liter and a pH of 7.0. With this solution, the reduction potential was measured (voltammetric analyzer P-1000: manufactured by Yanagimoto Seisakusho; dropping mercury electrode). The smaller the reduction potential value, the higher the resistance to reduction.

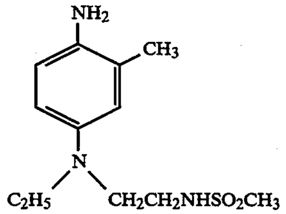

(D)

-continued
(A)
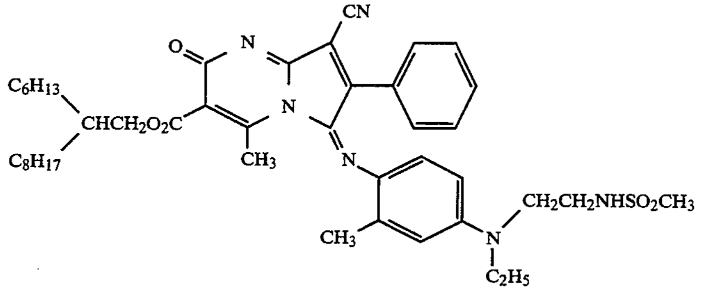
(B)
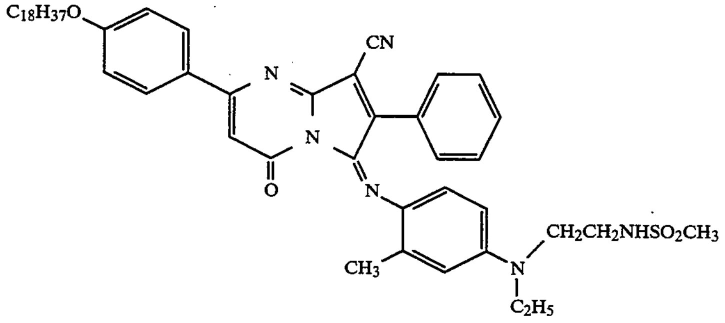
(C-1)
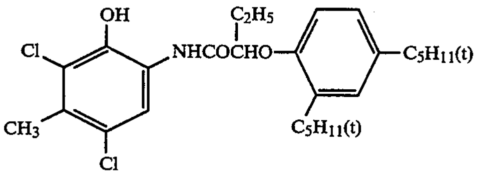
(C)
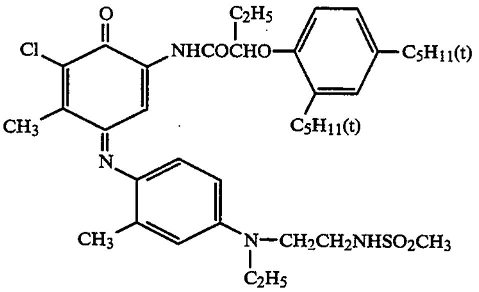
(C-2)
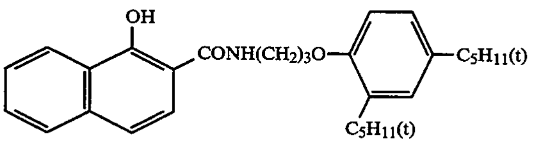
(E)
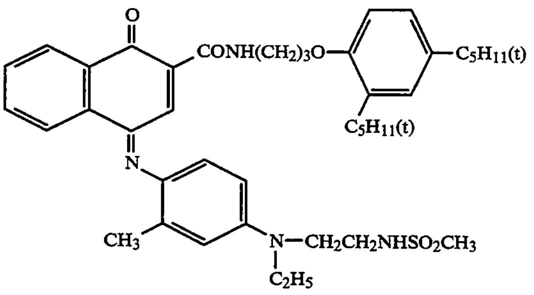

TABLE 6

| Dye | Potential E ½ (V vs S.C.E) | Remarks |
| --- | --- | --- |
| (A) | −0.33 | Present invention |
| (B) | −0.35 | Present invention |
| (C) | −0.11 | Comp. Example |
| (E) | −0.16 | Comp. Example |

It will be clear from Table 6 that the dyes obtained from the couplers of the present invention are not readily reduced.

It has heretofore been pointed out that dark fading of cyan dyes is likely to occur in a reducing atmosphere. However, the dyes obtained from the couplers of the present invention are superior in this point, as will be understood from Table 6.

EXAMPLE 2

Preparation of sample 101

Emulsion dispersion of coupler (I)-1 was prepared by the method described below.

1.03 g of coupler (I)-1 and 0.9 cc of tris(2-ethylhexyl)-phosphate were added to 10 cc of ethyl acetate and completely dissolved therein with the liquid temperature kept at about 40° C. (this is defined as an oil-phase solution).

Separately from the above, 4.2 g of gelatin was added to 26 cc of water and allowed to swell thoroughly at room temperature. Thereafter, the gelatin was completely dissolved with the liquid temperature kept at about 40° C. with the aqueous gelatin solution maintained at about 40° C., 3 cc of 5% sodium dodecylbenzenesulfonate and all the oil-phase solution, prepared in advance, were added to the aqueous gelatin solution and dispersed by using a homogenizer to obtain an emulsion dispersion . By using the emulsion dispersion , a coating solution having the following composition was prepared and then applied to a cellulose triacetate film base provided with an undercoat layer so that the amount of coupler applied was 1 mmol/m². Further, 1.5 g/m² of gelatin was coated on the resulting emulsion layer as a protective layer, thereby preparing sample 101.

| Coating solution: | |
| --- | --- |
| Emulsion (silver chlorobromide (Br: 30 mol%)) | 13 g |
| 10% gelatin | 28 g |
| Emulsion dispersion ① | 22 g |
| Water | 37 cc |
| Aqueous solution of 4% 1-oxy-3,5-dichloro-s-triazine sodium salt | 5 cc |

Preparation of samples 102 to 117

Samples 102 to 117 were prepared in the same manner as for sample 101 except that coupler (I)-1 was replaced with an equimolar amount of each of the couplers shown in Table 7 below.

Each of samples 102 to 117 was wedgewise exposed to white light and subjected to color development processing according to the following processing schedule (I).

Then, these samples were allowed to stand for 3 days at 80° C. and 70% RH to carry out forced testing. The density of a portion where the density before the testing was 1.0 was measured after the testing and used as a measure of image stability.

The results are shown in Table 7.

| | Processing Schedule (I) | |
| --- | --- | --- |
| Step | Temperature | Time |
| Color development | 35° C. | 1' |
| Bleach-fix | 30° C.–36° C. | 45" |
| Stabilization ① | 30° C.–37° C. | 20" |
| Stabilization ② | 30° C.–37° C. | 20" |
| Stabilization ③ | 30° C.–37° C. | 20" |
| Drying | 70° C.–85° C. | 60" |

(Stabilization was effected in a 4-tank counter-flow system: from tank ③ toward tank ①)

Each processing solution had the following composition.

| Color Developing Solution: | |
| --- | --- |
| Water | 800 ml |
| Ethylenediaminetetraacetic acid | 3.0 g |
| Triethanolamine | 8.0 g |
| Potassium chloride | 1.4 g |
| Potassium bromide | 0.6 g |
| Potassium carbonate | 25.0 g |
| N-ethyl-N-(β-methanesulfonamidoethyl)-3-methyl-4-aminoaniline sulfate | 5.0 g |
| N,N-diethylhydroxylamine | 4.2 g |
| 5,6-dihydroxybenzene-1,2,4-trisulfonic acid | 0.3 g |
| Fluorescent brightening agent (4,4'-diaminostilbene brightening agent) | 2.0 g |
| Water to make | 1000 ml |
| pH (25° C.) | 10.25 |
| Bleach-Fix Bath: | |
| Water | 400 ml |
| Ammonium thiosulfate (700 g/lit.) | 100 ml |
| Ammonium sulfite | 45 g |
| Ammonium (ethylenediaminetetra-acetato)iron(III) | 55 g |
| Disodium ethylenediaminetetraacetate | 3 g |
| Glacial acetic acid | 8 g |
| Water to make | 1000 ml |
| pH (25° C.) | 5.5 |
| Stabilizing Bath: | |
| Formalin (37%) | 0.1 g |
| Formalin-sulfurous acid additive | 0.7 g |
| 5-chloro-2-methyl-4-isothiazoline-3-one | 0.02 g |
| 2-methyl-4-isothiazoline-3-one | 0.01 g |
| Copper sulfate | 0.005 g |
| Water to make | 1000 ml |
| pH (25° C.) | 4.0 |

TABLE 7

| Sample | Coupler No. | Stability | Remarks |
| --- | --- | --- | --- |
| 101 | (III)-1 | 0.98 | Present invention |
| 102 | (III)-3 | 0.95 | " |
| 103 | (III)-4 | 0.94 | " |
| 104 | (III)-6 | 0.88 | " |
| 105 | (III)-7 | 0.98 | " |
| 106 | (III)-8 | 0.99 | " |
| 107 | (III)-11 | 0.93 | " |
| 108 | (III)-15 | 0.98 | " |
| 109 | (II)-1 | 0.97 | " |
| 110 | (II)-4 | 0.92 | " |
| 111 | (II)-5 | 0.96 | " |
| 112 | (II)-7 | 0.89 | " |
| 113 | (II)-9 | 0.99 | " |
| 114 | (II)-10 | 0.96 | " |
| 115 | (II)-11 | 0.97 | " |
| 116 | (II)-12 | 0.97 | " |
| 117 | C-1 | 0.68 | Comp. Example |

It will be clear from Table 7 that the couplers of the present invention have superior image stability.

Substantially the same results were also obtained with regard to couplers (IV)-2, (V)-2, (VI)-2, (VII)-2, (IX)-2, (X)-2, (XI)-2, (XII)-2, (XIII)-3, (XIV)-2, (XV)-2, (XVI)-

2, (XVII)-2, (XVIII)-2 and (XIX)-2 of the present invention.

EXAMPLE 3

On a cellulose triacetate film base provided with an undercoat layer, various layers having the following compositions were stacked up by coating to prepare sample 301 in the form of a multilayer color photosensitive material.

Composition of photosensitive layers

Principal materials used for the layers are classified as follows:

ExC: cyan coupler UV: ultraviolet absorbing agent
ExM: magenta coupler HBS: high-boiling organic solvent
ExY: yellow coupler H: gelatin hardening agent
ExS: sensitizing dye The numeral corresponding to each component represents the coating weight expressed in the unit of $g/m^2$. Regarding to silver halides, the coating weight in terms of silver is shown. However, with regard to sensitizing dyes, the coating weight per mol of silver halide in the same layer is shown in units of mol.

| Sample 301: | |
|---|---|
| 1st layer (antihalation layer) | |
| Black colloidal silver | silver 0.18 |
| Gelatin | 1.40 |
| ExM-1 | 0.18 |
| ExF-1 | $2.0 \times 10^{-3}$ |
| HBS-1 | 0.20 |
| 2nd layer (interlayer) | |
| Emulsion G | silver 0.065 |
| 2,5-di-t-pentadecylhydroquinone | 0.18 |
| ExC-2 | 0.020 |
| UV-1 | 0.060 |
| UV-2 | 0.080 |
| UV-3 | 0.10 |
| HBS-1 | 0.10 |
| HBS-2 | 0.020 |
| Gelatin | 1.04 |
| 3rd layer (low-sensitivity red-sensitive emulsion layer) | |
| Emulsion A | silver 0.25 |
| Emulsion B | silver 0.25 |
| ExS-1 | $6.9 \times 10^{-5}$ |
| ExS-2 | $1.8 \times 10^{-5}$ |
| ExS-3 | $3.1 \times 10^{-4}$ |
| ExC-1 | 0.17 |
| ExC-3 | 0.030 |
| ExC-4 | 0.10 |
| ExC-5 | 0.020 |
| ExC-7 | 0.0050 |
| ExC-8 | 0.010 |
| Cpd-2 | 0.025 |
| HBS-1 | 0.10 |
| Gelatin | 0.87 |
| 4th layer (medium-sensitivity red-sensitive emulsion layer) | |
| Emulsion D | silver 0.70 |
| ExS-1 | $3.5 \times 10^{-4}$ |
| ExS-2 | $1.6 \times 10^{-5}$ |
| ExS-3 | $5.1 \times 10^{-4}$ |
| ExC-1 | 0.13 |
| ExC-2 | 0.060 |
| ExC-3 | 0.0070 |
| ExC-4 | 0.090 |
| ExC-5 | 0.025 |
| ExC-7 | 0.0010 |
| ExC-8 | 0.0070 |
| Cpd-2 | 0.023 |
| HBS-1 | 0.10 |
| Gelatin | 0.75 |
| 5th layer (high-sensitivity red-sensitive emulsion layer) | |
| Emulsion E | silver 1.40 |
| ExS-1 | $2.4 \times 10^{-4}$ |
| ExS-2 | $1.0 \times 10^{-4}$ |
| ExS-3 | $3.4 \times 10^{-4}$ |
| ExC-1 | 0.12 |
| ExC-3 | 0.045 |
| ExC-6 | 0.020 |
| ExC-8 | 0.025 |
| Cpd-2 | 0.050 |
| HBS-1 | 0.22 |
| HBS-2 | 0.10 |
| Gelatin | 1.20 |
| 6th layer (interlayer) | |
| Cpd-1 | 0.10 |
| HBS-1 | 0.50 |
| Gelatin | 1.10 |
| 7th layer (low-sensitivity green-sensitive emulsion layer) | |
| Emulsion C | silver 0.35 |
| ExS-4 | $3.0 \times 10^{-5}$ |
| ExS-5 | $2.1 \times 10^{-4}$ |
| ExS-6 | $8.0 \times 10^{-4}$ |
| ExM-1 | 0.010 |
| ExM-2 | 0.33 |
| ExM-3 | 0.086 |
| ExY-1 | 0.015 |
| HBS-1 | 0.30 |
| HBS-3 | 0.010 |
| Gelatin | 0.73 |
| 8th layer (medium-sensitivity green-sensitive emulsion layer) | |
| Emulsion D | silver 0.80 |
| ExS-4 | $3.2 \times 10^{-5}$ |
| ExS-5 | $2.2 \times 10^{-4}$ |
| ExS-6 | $8.4 \times 10^{-4}$ |
| ExM-2 | 0.13 |
| ExM-3 | 0.030 |
| ExY-1 | 0.018 |
| HBS-1 | 0.16 |
| HBS-3 | $8.0 \times 10^{-3}$ |
| Gelatin | 0.90 |
| 9th layer (high-sensitivity green-sensitive emulsion layer) | |
| Emulsion E | silver 1.25 |
| ExS-4 | $3.7 \times 10^{-5}$ |
| ExS-5 | $8.1 \times 10^{-5}$ |
| ExS-6 | $3.2 \times 10^{-4}$ |
| ExC-1 | 0.010 |
| ExM-1 | 0.030 |
| ExM-4 | 0.040 |
| ExM-5 | 0.019 |
| Cpd-3 | 0.040 |
| HBS-1 | 0.25 |
| HBS-2 | 0.10 |
| Gelatin | 1.44 |
| 10th layer (yellow filter layer) | |
| Yellow colloidal silver | silver 0.030 |
| Cpd-1 | 0.16 |
| HBS-1 | 0.60 |
| Gelatin | 0.60 |
| 11th layer (low-sensitivity blue-sensitive emulsion layer) | |
| Emulsion C | silver 0.18 |
| ExS-7 | $8.6 \times 10^{-4}$ |
| ExY-1 | 0.020 |
| ExY-2 | 0.022 |
| ExY-3 | 0.050 |
| ExY-4 | 0.020 |
| HBS-1 | 0.28 |
| Gelatin | 1.10 |
| 12th layer (medium-sensitivity blue-sensitive emulsion layer) | |
| Emulsion D | silver 0.40 |
| ExS-7 | $7.4 \times 10^{-4}$ |
| ExC-7 | $7.0 \times 10^{-3}$ |
| ExY-2 | 0.050 |
| ExY-3 | 0.10 |
| HBS-1 | 0.050 |

-continued

| Sample 301: | |
|---|---|
| Gelatin | 0.78 |
| 13th layer (high-sensitivity blue-sensitive emulsion layer) | |
| Emulsion F | silver 1.00 |
| ExS-7 | $4.0 \times 10^{-4}$ |
| ExY-2 | 0.10 |
| ExY-3 | 0.10 |
| HBS-1 | 0.070 |
| Gelatin | 0.86 |
| 14th layer (1st protective layer) | |
| Emulsion G | silver 0.20 |
| UV-4 | 0.11 |
| UV-5 | 0.17 |
| BBS-1 | $5.0 \times 10^{-2}$ |
| Gelatin | 1.00 |
| 15th layer (2nd protective layer) | |
| H-1 | 0.40 |
| B-1 (diameter: 1.7 μm) | $5.0 \times 10^{-2}$ |
| B-2 (diameter: 1.7 μm) | 0.10 |
| B-3 | 0.10 |
| S-1 | 0.20 |
| Gelatin | 1.20 |

In addition, the layers contained proper additives, e.g., W-1 to W-3, B-4 to B-6, F-1 to F-17, iron salt, lead salt, gold salt, platinum salt, iridium salt, and rhodium salt for the purpose of improving storage properties, processability, pressure resistance, antifungal and antibacterial properties, antistatic properties and coating properties.

TABLE 8

| Emulsion | Mean AgI content (%) | Mean grain size (μm) | Coefficient of variation in grain size (%) | Diameter/thickness ratio | Silver content ratio [core/middle/shell] (AgI content) | Grain structure/shape |
|---|---|---|---|---|---|---|
| A | 4.0 | 0.45 | 27 | 1 | [1/3] (13/1) | Double octahedral grains |
| B | 8.9 | 0.70 | 14 | 1 | [3/7] (25/2) | Double octahedral grains |
| C | 2.0 | 0.55 | 25 | 7 | — | Homogeneous tabular grains |
| D | 9.0 | 0.65 | 25 | 6 | [12/59/29] (0/11/8) | Triple tabular grains |
| E | 9.0 | 0.85 | 23 | 5 | [8/59/33] (0/11/8) | Triple tabular grains |
| F | 14.5 | 1.25 | 25 | 3 | [37/63] (34/3) | Double tabular grains |
| G | 1.0 | 0.07 | 15 | 1 | — | Homogeneous fine grains |

In Table 8:

(1) Emulsions A to F had been subjected to reduction sensitization by using thiourea dioxide and thiosulfonic acid during the preparation of grains according to Example in Japanese Patent Application Laid-Open (KOKAI) No. 2-191938 (1990).

(2) Emulsions A to F had been subjected to gold sensitization and sulfur sensitization in the presence of the spectral sensitizing dyes, mentioned for each photosensitive layer, and sodium thiocyanate, according to Example in Japanese Patent Application Laid-Open (KOKAI) No. 3-237450 (1991).

(3) For the preparation of tabular grains, a low-molecular weight gelatin was used according to Example in Japanese Patent Application Laid-Open (KOKAI) No. 1-158426 (1989).

(4) A dislocation line such as that described in Japanese Patent Application Laid-Open (KOKAI) No. 3-237450 (1991) was observed in the tabular grains and the grains having a normal crystal form by using a high-voltage electron microscope.

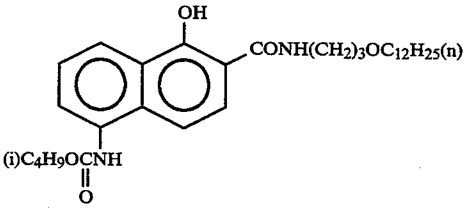

ExC-1

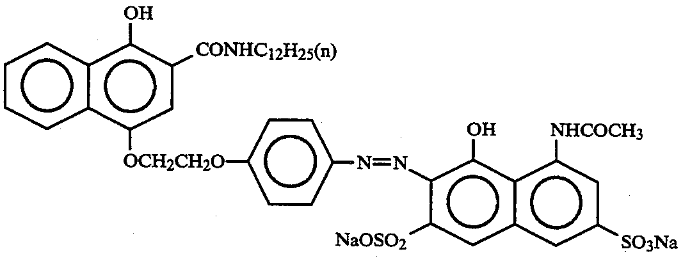

ExC-2

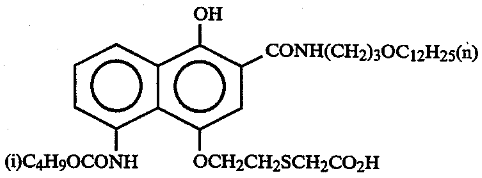

ExC-3

-continued
ExC-4
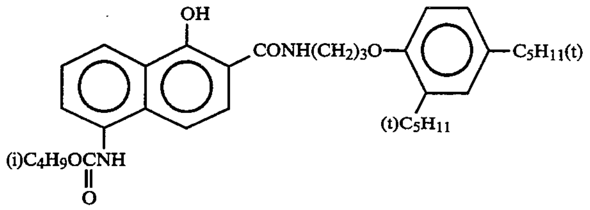
ExC-5
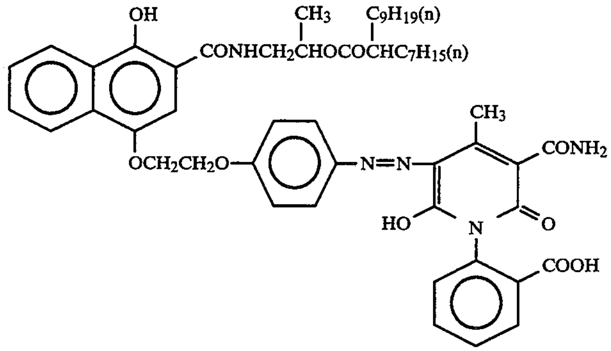
ExC-6
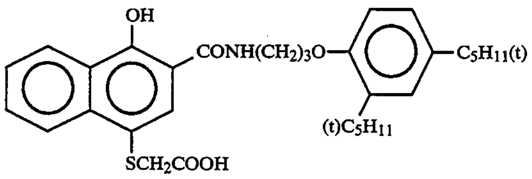
ExC-7
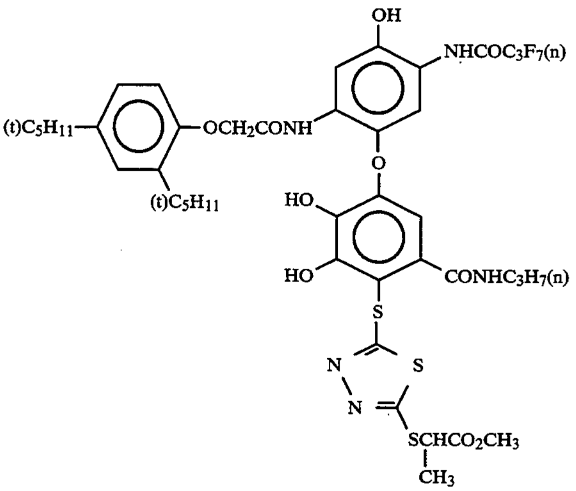
ExC-8
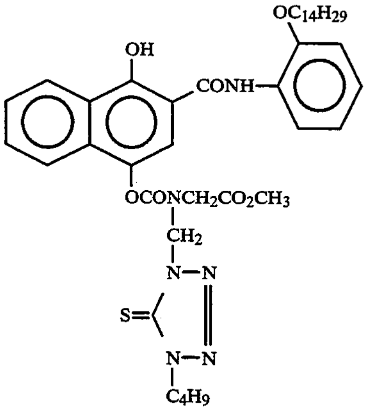

-continued
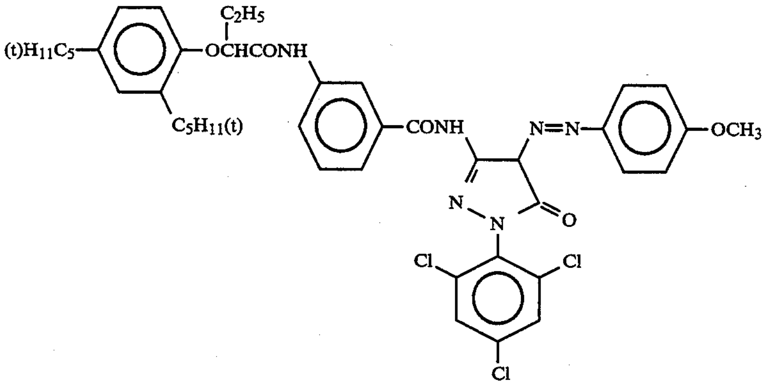
ExM-1
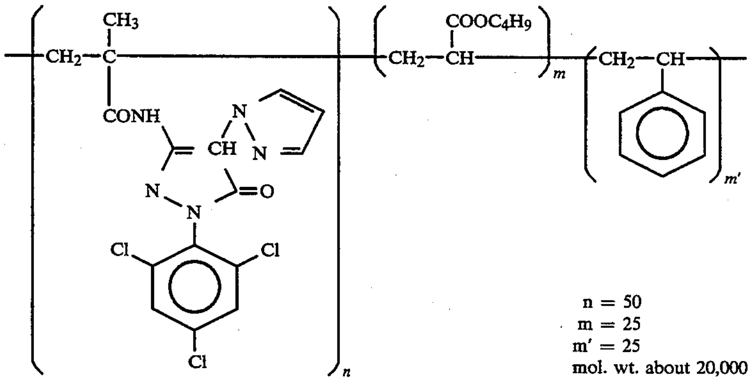
ExM-2
n = 50
m = 25
m' = 25
mol. wt. about 20,000
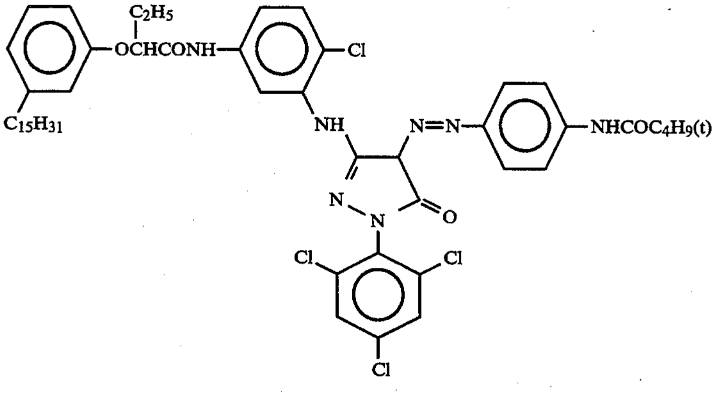
ExM-3
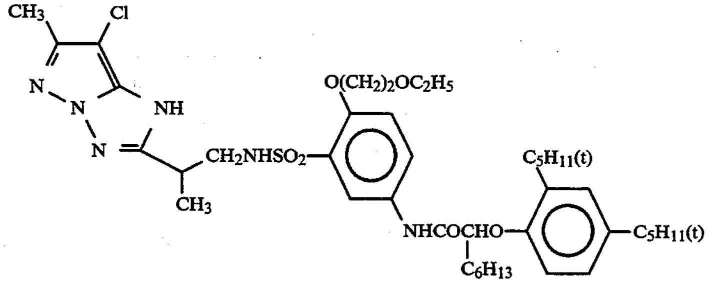
ExM-4

-continued
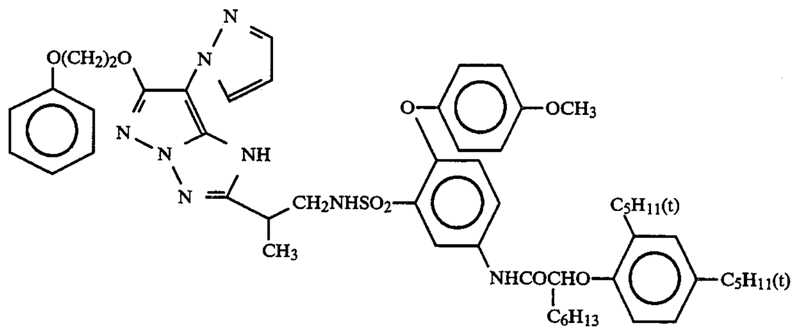
ExM-5
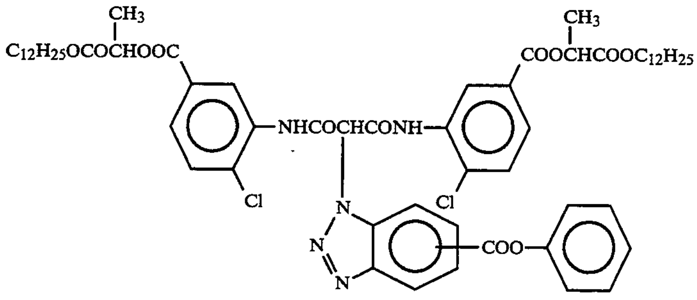
ExY-1
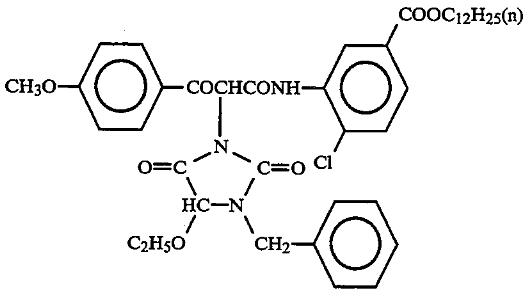
ExY-2
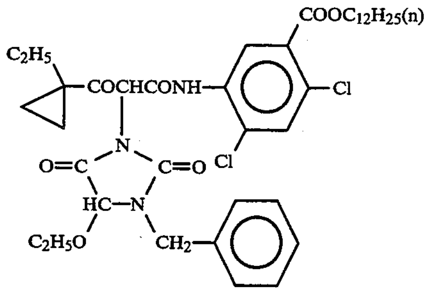
ExY-3
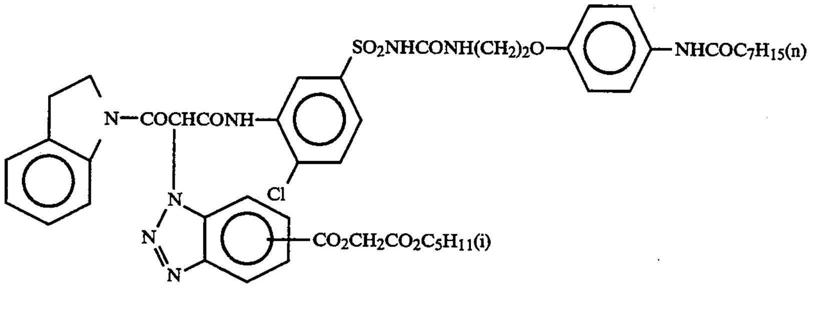
ExY-4

-continued
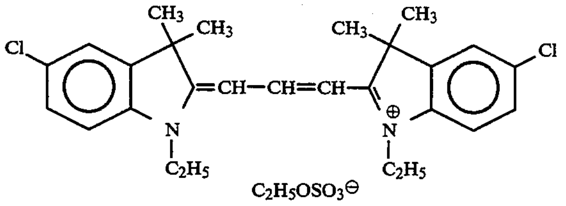
ExF-1
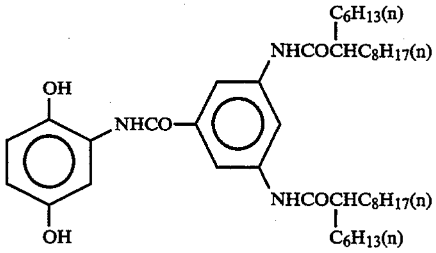
Cpd-1
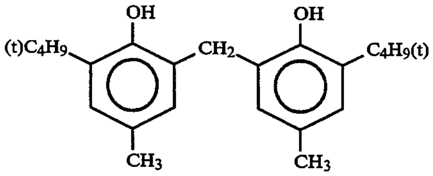
Cpd-2
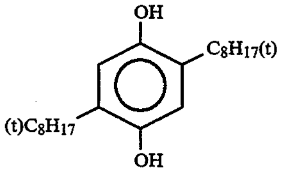
Cpd-3
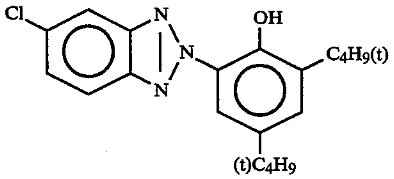
UV-1
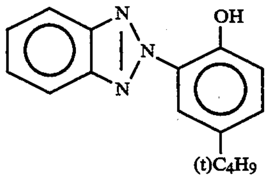
UV-2
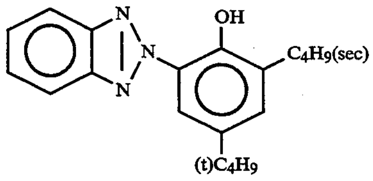
UV-3
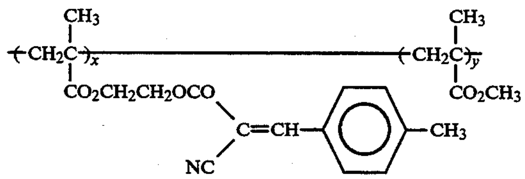
x:y = 70:30 (wt %)
UV-4

-continued
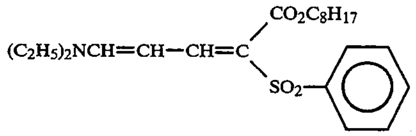
UV-5
tricresyl phosphate HBS-1
di-n-butylphthalate HBS-2
HBS-3
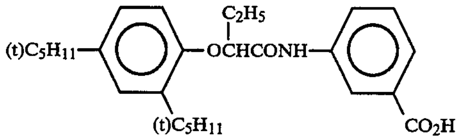
ExS-1
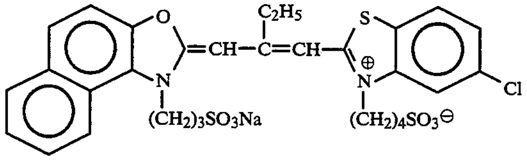
ExS-2
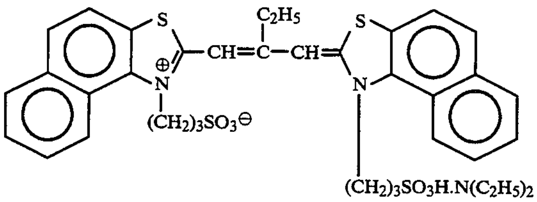
ExS-3
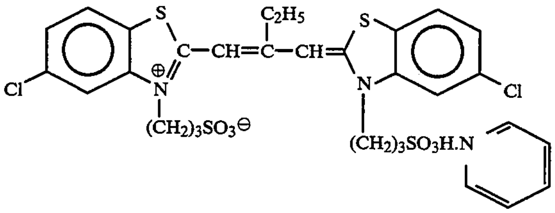
ExS-4
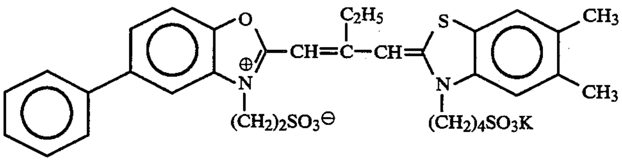
ExS-5
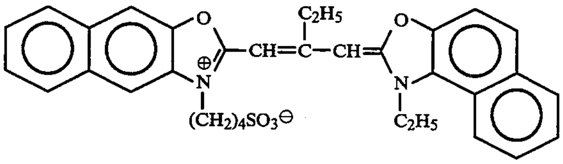
ExS-6
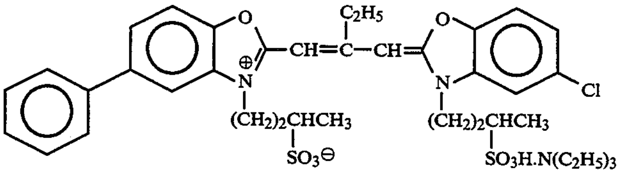

-continued
ExS-7
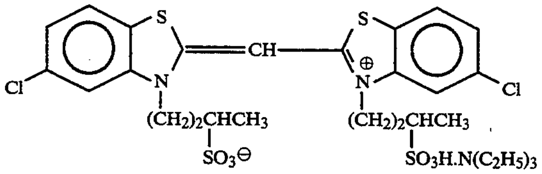
S-1
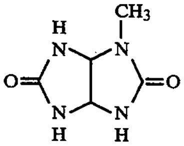
H-1
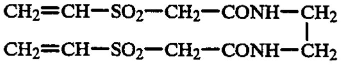
B-1
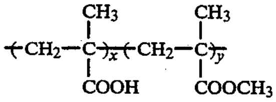
x/y = 10/90
B-2
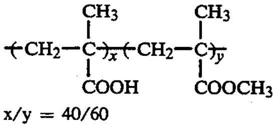
x/y = 40/60
B-3
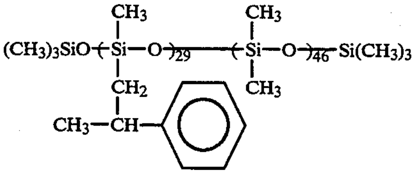
B-4
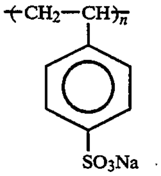
B-5
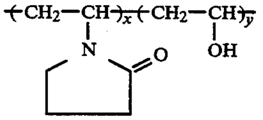
x/y = 70/30
B-6
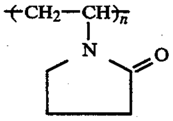
(mol. wt. ab. 10,000)
W-1
$C_8F_{17}SO_2NHCH_2CH_2CH_2OCH_2CH_2\overset{\oplus}{N}(CH_3)_3$
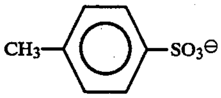

-continued
W-2
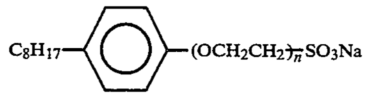
n = 2~4
W-3
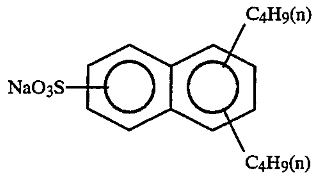
F-1
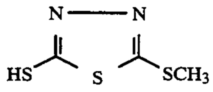
F-2
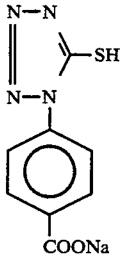
F-3
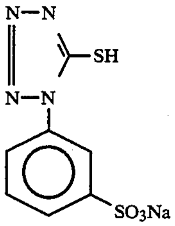
F-4
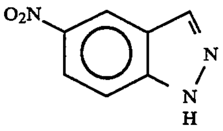
F-5
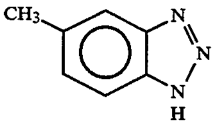
F-6
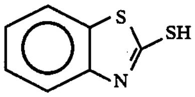
F-7
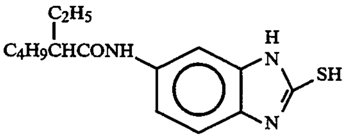

-continued

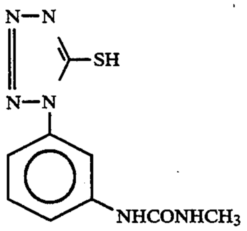

F-8

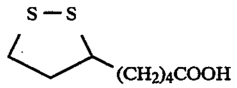

F-9

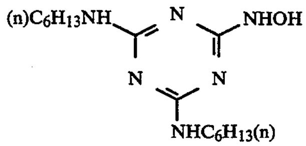

F-10

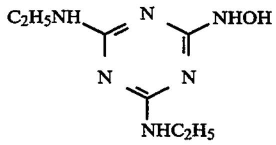

F-11

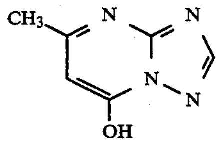

F-12

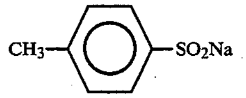

F-13

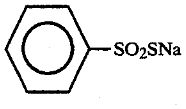

F-14

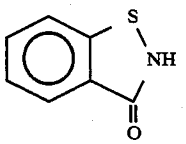

F-15

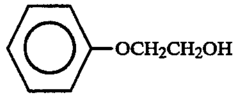

F-16

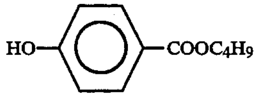

F-17

Next, samples 302 to 310 were prepared in the same manner as for sample 301 except that cyan couplers ExC-1 and ExC-4 in the 3rd, 4th and 5th layers were replaced with an equimolar amount of each of the couplers shown in Table 9. Each of samples 301 to 310 was gradationally exposed to red light and then processed by using an automatic processor according to the following processing schedule (II).

Processing Schedule (II)

| Step | Time | Temperature | Replenishment rate* | Tank capacity |
|---|---|---|---|---|
| Color development | 3'05" | 38° C. | 600 ml | 17 lit. |
| Bleach | 50" | 38° C. | 140 ml | 5 lit. |
| Bleach-fix | 50" | 38° C. | — | 5 lit. |

-continued

| Processing Schedule (II) | | | | |
|---|---|---|---|---|
| Step | Time | Temperature | Replenishment rate* | Tank capacity |
| Fixing | 50" | 38° C. | 420 ml | 5 lit. |
| Washing | 30" | 38° C. | 980 ml | 3 lit. |
| Stabilization (1) | 20" | 38° C. | — | 3 lit. |
| Stabilization (2) | 20" | 38° C. | 560 ml | 3 lit. |
| Drying | 60" | 60° C. | | |

*Replenishment rate: the amount of replenisher per $m^2$ of the photosensitive material.

Stabilization was effected in a 2-tank counter-flow system: from tank (2) toward tank (1). Overflow of washing water was all introduced into the fixing bath. Replenishment to the bleach-fix bath was effected by providing cut portions in the respective upper parts of the bleaching and fixing tanks of the automatic processor so that all the overflow resulting from the supply of the replenisher into the bleaching and fixing tanks was allowed to flow into the bleach-fix bath. The amount of developing bath carried to the bleach step, the amount of bleaching bath carried to the bleach-fix step, the amount of bleach-fix bath carried to the fixing step, and the amount of fixing bath carried to the washing step were respectively 65 ml, 50 ml, 50 ml, and 50 ml per $m^2$ of the photosensitive material. The crossover time was 6 sec. each, which was included in the processing time in the preceding step.

As each replenisher, the same processing solution as that in the corresponding tank was used.

Each processing solution had the following composition.

| | | |
|---|---|---|
| Color Developing Solution: | | |
| Diethylenetriaminepentaacetic acid | 2.0 | g |
| 1-hydroxyethylidene-1,1-diphosphonic acid | 3.3 | g |
| Sodium sulfite | 3.9 | g |
| Potassium carbonate | 37.5 | g |
| Potassium bromide | 1.4 | g |
| Potassium iodide | 1.3 | mg |
| Hydroxylamine.sulfate | 2.4 | g |
| 2-methyl-4-[N-ethyl-N-(β-hydroxyethyl)amino] aniline sulfate | 4.5 | g |
| Water to make | 1.0 | lit. |
| pH | 10.15 | |
| Bleaching Bath: | | |
| Ammonium 1,3-(diaminopropanetetraaceto) iron(II) monohydrate | 130 | g |
| Ammonium bromide | 80 | g |
| Ammonium nitrate | 15 | g |
| Hydroxyacetic acid | 50 | g |
| Acetic acid | 40 | g |
| Water to make | 1.0 | lit. |
| pH (adjusted with aqueous ammonia) | 4.4 | |

Bleach-Fix Bath

A mixture in the volume ratio of 15:85 of the above-described bleaching bath and the following fixing solution (pH: 7.0).

| | | |
|---|---|---|
| Fixing solution: | | |
| Ammonium sulfite | 19 | g |
| Aqueous ammonium thiosulfate (700 g/lit.) | 280 | ml |
| Imidazole | 15 | g |
| Ethylenediaminetetraacetic acid | 15 | g |
| Water to make | 1.0 | lit. |
| pH (adjusted with aqueous ammonium and acetic acid) | 7.4 | |

Washing Water

Tap water was passed through a mixed bed column packed with an H-type strongly acidic cation exchange resin Amberlite IR-120B (manufactured by Rohm & Haas Co.) and an OH-type strongly basic anion exchange resin Amberlite IR-400 (manufactured by Rohm a Haas Co.) to reduce calcium and magnesium ions to 3 mg/lit. or less, respectively. To the thus treated water were added 20 mg/lit. of sodium isocyanurate dichloride and 150 mg/lit. of sodium sulfate. The resulting washing water had a pH between 6.5 and 7.5.

| | | |
|---|---|---|
| Stabilizing Bath: | | |
| Sodium p-toluenesulfinate | 0.03 | g |
| Polyoxyethylene-p-monononyl phenyl ether (average degree of polymerization: 10) | 0.2 | g |
| Disodium ethylenediaminetetraacetate | 0.05 | g |
| 1,2,4-triazole | 1.3 | g |
| 1,4-bis(1,2,4-triazole-1-ylmethyl)piperazine | 0.75 | g |
| Water to make | 1.0 | lit. |
| pH | 8.5 | |

Samples 301 to 310 that developed color were measured for the red density with a Fuji-type densitometer. The activity was evaluated by obtaining the gradient G of the straight line connecting two points where the cyan dye density corresponded to fog densities +0.5 and +1.0, respectively, and expressing it in a value relative to the gradient G of sample 301 as a standard (G=1.00). Regarding the dye image storage characteristics, evaluation was made in the same way as in Example 1 except that the value measured at a point of cyan density 1.5 was used as a measure of image storage characteristics. The results are shown in Table 9 below.

TABLE 9

| Sample No. | Coupler | Relative activity | Image storage characteristics |
|---|---|---|---|
| 301 | EX-2 | 1.00 | 97% |
| 302 | (III)-1 | 1.15 | 97% |
| 303 | (III)-6 | 1.14 | 95% |
| 304 | (III)-8 | 1.17 | 99% |
| 305 | (III)-19 | 1.29 | 97% |
| 306 | (II)-1 | 1.17 | 97% |
| 307 | (II)-7 | 1.14 | 94% |
| 308 | (II)-9 | 1.21 | 99% |
| 309 | (II)-12 | 1.27 | 96% |
| 310 | (II)-17 | 1.23 | 97% |

It will be understood from Table 9 that the cyan couplers of the present invention have high relative activities and excellent dye image storage characteristics even in the case of a multilayer color photosensitive material for photography (color negative film).

Substantially the same results were also obtained with regard to couplers (IV)-3, (V)-3, (VI)-3, (VII)-3, (IX)-3, (X)-3, (XI)-3, (XII)-3, (XIII)-3, (XIV)-3, (XV)-3, (XVI)-3, (XVII)-3, (XVIII)-3 and (XIX)-3.

EXAMPLE 4

Preparation of Sample 401

After the surface of a double-side polyethylene laminated paper support was treated with corona discharge, a gelatin undercoat layer containing sodium dodecylbenzenesulfonate was provided thereon, and further various photographic constituent layers were coated thereon, thereby preparing a multilayer color photographic paper (sample 401) having the following layer configuration. The coating solutions were prepared as follows.

Preparation of 1st layer coating solution 153.0 g of yellow coupler (ExY), 15.0 g of dye image stabilizing agent (Cpd-1), 7.5 g of dye image stabilizing agent (Cpd-2), 16.0 g of dye image stabilizing agent (Cpd-3), 25 g of solvent (Solv-1), and 25 g of solvent (Solv-2) were dissolved in 180 cc of ethyl acetate, and the resulting solution was dispersed in 1,000 g of 10% gelatin aqueous solution containing 60 cc of 10% sodium dodecylbenzenesulfonate and 10 g of citric acid to prepare an emulsion dispersion A. In the meantime, a silver chlorobromide emulsion A was prepared (a mixture in the silver molar ratio of 3:7 of a large-sized emulsion A of cubic grains having a mean grain size of 0.88 μm and a small-sized emulsion A having a mean grain size of 0.70 μm; the coefficients of variation in the grain size distribution were 0.08 and 0.10, respectively; and each of the large- and small-sized emulsions had 0.3 mol % silver bromide localized in a part of the grain surface). The emulsion had the following blue-sensitive sensitizing dyes A and B each added thereto in an amount of $2.0\times10^{-4}$ mol per mol of silver for the large-sized emulsion A and $2.5\times10^{-4}$ mol per mol of silver for the small-sized emulsion A. Chemical ripening for this emulsion was effected by adding sulfur and gold sensitizing agents. The above-described emulsion dispersion A and the silver chlorobromide emulsion A were mixed and dissolved to prepare a 1st layer coating solution having the composition described later.

Preparation of 5th layer coating solution 33.0 g of cyan coupler (ExC), 18.0 g of ultraviolet absorbing agent (UV-2), 30.0 g of dye image stabilizing agent (Cpd-1), 15.0 g of dye image stabilizing agent (Cpd-9), 15.0 g of dye image stabilizing agent (Cpd-10), 1.0 g of dye image stabilizing agent (Cpd-11), 1.0 g of dye image stabilizing agent (Cpd-8), 1.0 g of dye image stabilizing agent (Cpd-6), 22 g of solvent (Solv-6), and 1.0 g of solvent (Solv-1) were dissolved in 60 cc of ethyl acetate, and the resulting solution was added to 500 cc of 20% gelatin aqueous solution containing 8 cc of sodium dodecylbenzenesulfonate and then dispersed by an ultrasonic homogenizer to prepare an emulsion dispersion C. In the meantime, a silver chlorobromide emulsion C was prepared (a mixture in the Ag molar ratio of 1:4 of a large-sized emulsion C of cubic grains having a mean grain size of 0.50 μm and a small-sized emulsion C having a mean grain size of 0.41 μm; the coefficients of variation in the grain size distribution were 0.09 and 0.11, respectively; and each of the large- and small-sized emulsions had 0.8 mol % AgBr localized in a part of the grain surface). The emulsion C had red-sensitive sensitizing dye E added thereto in an amount of $0.9\times10^{-4}$ mol per mol of silver for the large-sized emulsion C and $1.1\times10^{-4}$ mol per mol of silver for the small-sized emulsion C. Further, compound F was added thereto in an amount of $2.6\times10^{-3}$ mol per mol of silver halide. Chemical ripening for this emulsion C was effected by adding sulfur and gold sensitizing agents. The above-described emulsion dispersion and the red-sensitive silver chlorobromide emulsion C were mixed and dissolved to prepare a 5th layer coating solution having the composition described later.

Coating solutions for the 2nd to 4th layers and 6th and 7th layers were prepared in the same manner as in the case of the 1st layer coating solution. As a gelatin hardening agent for each layer, 1-oxy-3,5-dichloro-s-triazine sodium salt was employed.

In addition, Cpd-14 and Cpd-15 were added to each layer so that the total amounts of Cpd-14 and Cpd-15 were 25.0 $mg/m^2$ and 50 $mg/m^2$, respectively.

The spectral sensitizing dyes employed in the silver chlorobromide emulsions for the photosensitive emulsion layers are shown below:

TABLE 10

Blue-sensitive emulsion layer

Sensitizing dye A

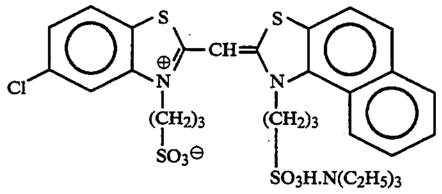

and

Sensitizing dye B

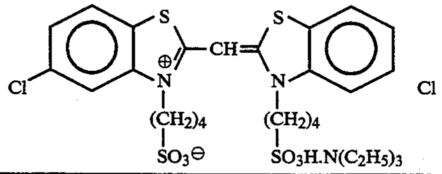

TABLE 11

Green-sensitive emulsion layer

Sensitizing dye C

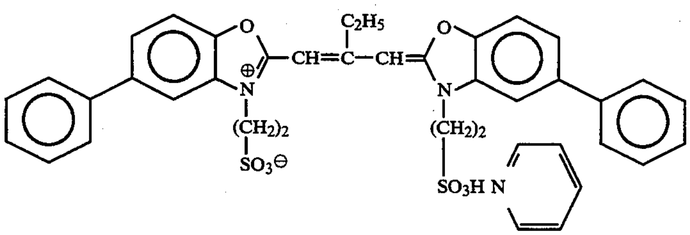

($4.0\times10^{-4}$ mol for large-sized emulsion B, and $5.6\times10^{-4}$ mol for small-sized emulsion B, per mol of silver halide)

Sensitizing dye D

TABLE 11-continued

| Green-sensitive emulsion layer |
| --- |
| 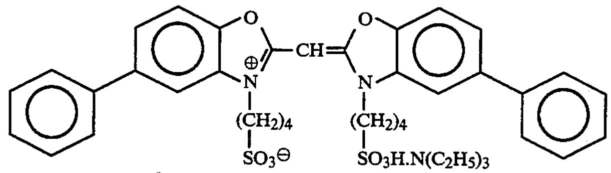 |
| ($7.0 \times 10^{-5}$ mol for large-sized emulsion B, and $1.0 \times 10^{-5}$ mol for small-sized emulsion B, per mol of silver halide) |

TABLE 12

| Red-sensitive emulsion layer |
| --- |
| Sensitizing dye E |
| 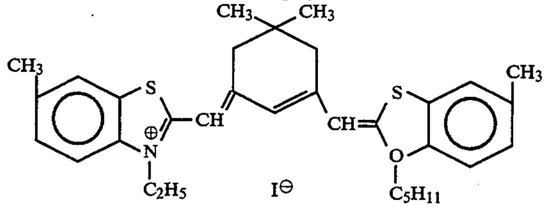 |
| Compound F |
| 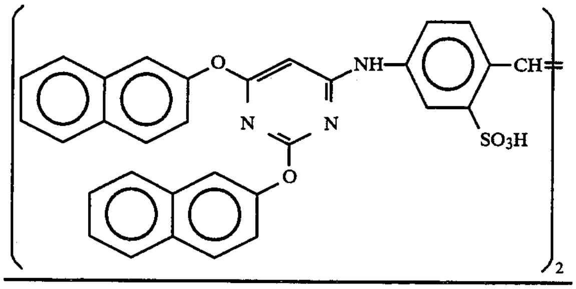 |

Further, 1-(5-methylureidophenyl)-5-mercaptotetrazole was added to the blue-, green- and red-sensitive emulsion layers in amounts of $8.5\times10^{-5}$ mol, $7.7\times10^{-4}$ mol and $2.5\times10^{-4}$, respectively, per mol of silver halide.

In addition, 4-hydroxy-6-methyl-1,3,3a,7-tetrazinedene was added to the blue- and green-sensitive emulsion layers in amounts of $1\times10^{-4}$ and $2\times10^{-4}$, respectively, per mol of silver halide.

Further, the following dyes (each value in parentheses represents coating weight) were added to the emulsion layers for the purpose of irradiation prevention.

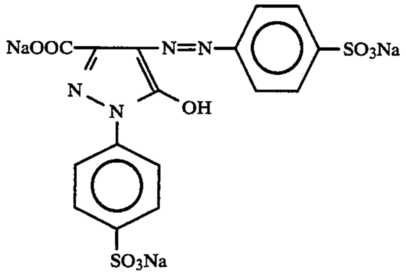

(10 mg/m$^2$)

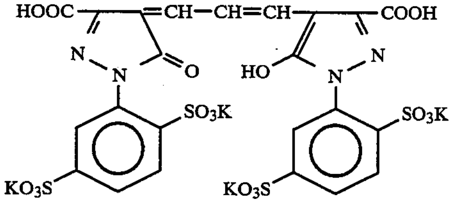

(10 mg/m$^2$)

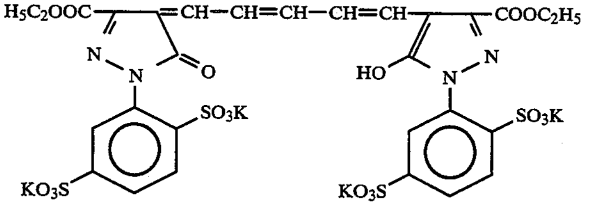

(40 mg/m$^2$)

-continued and

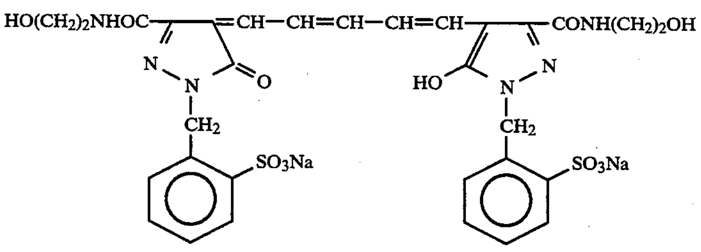

(20 mg/$m^2$)

Layer configuration

The composition of each layer will be shown below. The numerals represent coating weight (g/$m^2$). For the silver halide emulsions, the numerals represent coating weight in terms of silver.

TABLE 13

| | |
|---|---|
| Support | |
| Polyethylene laminated paper [polyethylene on the 1st layer side contained white pigment ($TiO_2$) and bluing dye (ultramarine)] | |
| 1st layer (blue-sensitive emulsion layer) | |
| The above-described silver chlorobromide emulsion A | 0.27 |
| Gelatin | 1.36 |
| Yellow coupler (ExY) | 0.79 |
| Dye image stabilizing agent (Cpd-1) | 0.08 |
| Dye image stabilizing agent (Cpd-2) | 0.04 |
| Dye image stabilizing agent (Cpd-3) | 0.08 |
| Solvent (Solv-1) | 0.13 |
| Solvent (Solv-2) | 0.13 |
| 2nd layer (color amalgamation preventing layer) | |
| Gelatin | 1.00 |
| Color amalgamation preventing agent (Cpd-4) | 0.06 |
| Solvent (Solv-7) | 0.03 |
| Solvent (Solv-2) | 0.25 |
| Solvent (Solv-3) | 0.25 |

TABLE 14

| | |
|---|---|
| 3rd layer (green-sensitive emulsion layer) | |
| Silver chlorobromide emulsion (mixture in the Ag molar ratio of 1:3 of large-sized emulsion B of cubic grains having a mean grain size of 0.55 μm and small-sized emulsion B having a mean grain size of 0.39 μm; coefficients of variation in grain size distribution were 0.10 and 0.08, respectively; and each of large- and small-sized emulsions had 0.8 mol % AgBr localized in a part of grain surface) | 0.13 |
| Gelatin | 1.45 |
| Magenta coupler (ExM) | 0.16 |
| Dye image stabilizing agent (Cpd-5) | 0.15 |
| Dye image stabilizing agent (Cpd-2) | 0.03 |

TABLE 14-continued

| | |
|---|---|
| Dye image stabilizing agent (Cpd-6) | 0.01 |
| Dye image stabilizing agent (Cpd-7) | 0.01 |
| Dye image stabilizing agent (Cpd-8) | 0.08 |
| Solvent (Solv-3) | 0.50 |
| Solvent (Solv-4) | 0.15 |
| Solvent (Solv-5) | 0.15 |
| 4th layer (color amalgamation preventing layer) | |
| Gelatin | 0.70 |
| Color amalgamation preventing agent (Cpd-4) | 0.04 |
| Solvent (Solv-7) | 0.02 |
| Solvent (Solv-2) | 0.18 |
| Solvent (Solv-3) | 0.18 |

TABLE 15

| | |
|---|---|
| 5th layer (red-sensitive emulsion layer) | |
| Silver chlorobromide emulsion C | 0.20 |
| Gelatin | 0.85 |
| Cyan coupler (ExC) | 0.33 |
| Ultraviolet absorbing agent (UV-2) | 0.18 |
| Dye image stabilizing agent (Cpd-1) | 0.30 |
| Dye image stabilizing agent (Cpd-9) | 0.15 |
| Dye image stabilizing agent (Cpd-10) | 0.15 |
| Dye image stabilizing agent (Cpd-11) | 0.01 |
| Solvent (Solv-6) | 0.20 |
| Dye image stabilizing agent (Cpd-8) | 0.01 |
| Dye image stabilizing agent (Cpd-6) | 0.01 |
| Solvent (Solv-1) | 0.01 |
| 6th layer (ultraviolet absorbing layer) | |
| Gelatin | 0.55 |
| Ultraviolet absorbing agent (UV-1) | 0.38 |
| Dye image stabilizing agent (Cpd-12) | 0.15 |
| Dye image stabilizing agent (Cpd-5) | 0.02 |

TABLE 16

| 7th layer (protective layer) | |
|---|---|
| Gelatin | 1.13 |
| Acryl modified copolymer of polyvinyl alcohol (degree of modification: 17%) | 0.05 |
| Liquid paraffin | 0.02 |
| Dye image stabilizing agent (Cpd-5) | 0.01 |

(ExY) Yellow coupler: mixture in the molar ratio of 1:1 of

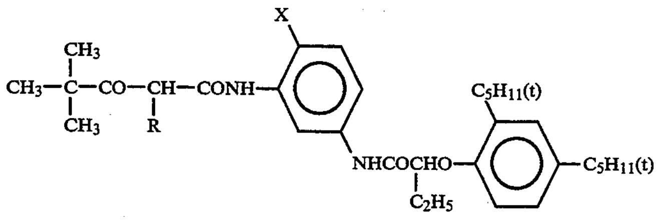

-continued
R = 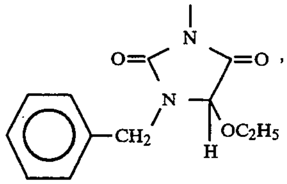 , X = Cl and
R = 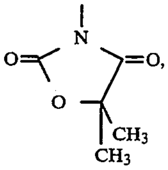, $X = OCH_3$
(ExM) Magenta coupler
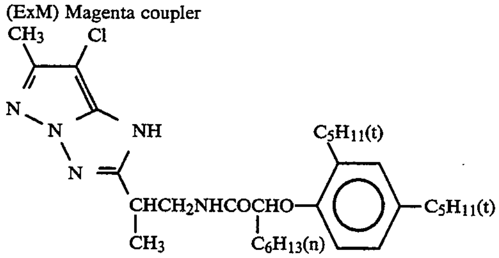
(ExC) Cyan coupler: mixture in the molar ratio of 3:7 of
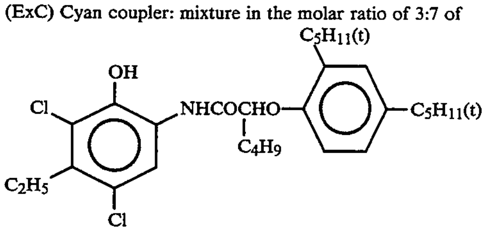
and
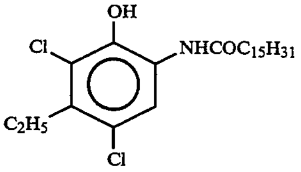
(Cpd-1) Dye image stabilizing agent
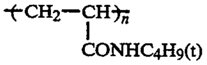
mean mol. wt. 60,000
(Cpd-2) Dye image stabilizing agent
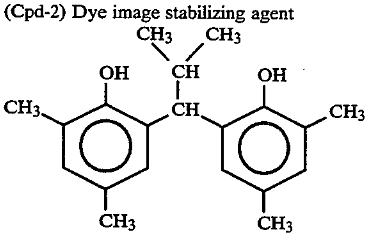
(Cpd-3) Dye image stabilizing agent
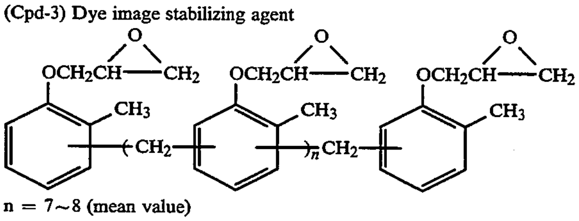
n = 7~8 (mean value)

-continued
(Cpd-4) Color amalgamation preventing agent
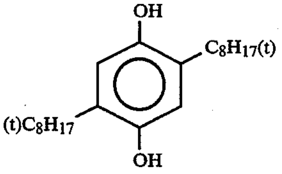
(Cpd-5) Dye image stabilizing agent
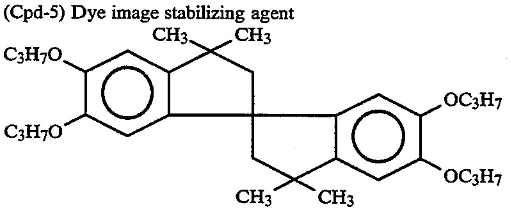
(Cpd-6)
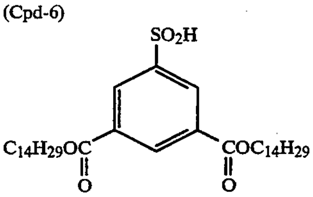
(Cpd-7)
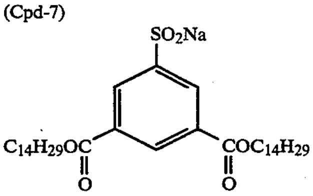
(Cpd-8) Dye image stabilizing agent
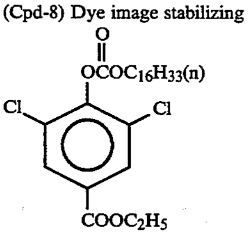
(Cpd-9) Dye image stabilizing agent
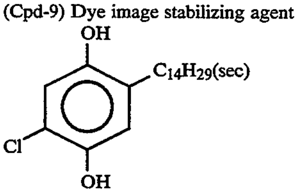
(Cpd-10) Dye image stabilizing agent
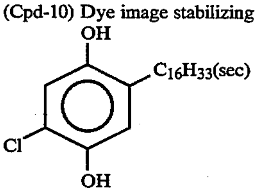
(Cpd-11)
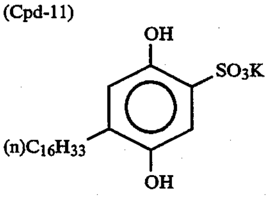

-continued
(Cpd-12)
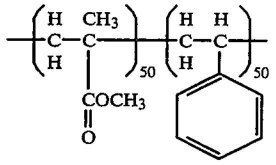
mean mol. wt. 60,000
(Cpd-13)
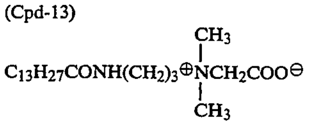
(Cpd-14) Antiseptic
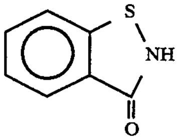
(Cpd-15) Antiseptic
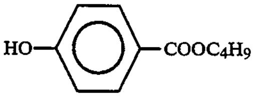
(UV-1) Ultraviolet absorbing agent:
mixture in the weight ratio of 10:5:1:5 of
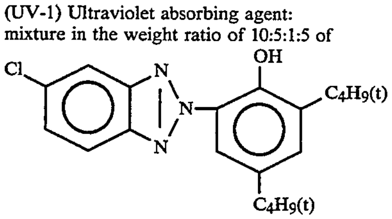
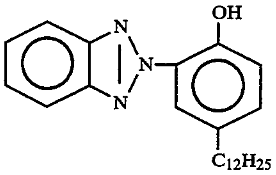
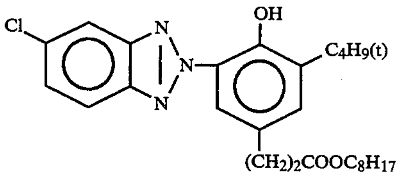
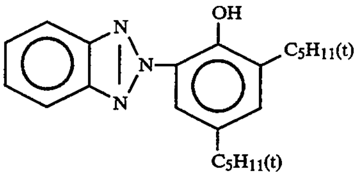
(UV-2) Ultraviolet absorbing agent:
mixture in the weight ratio of 1:2:2 of
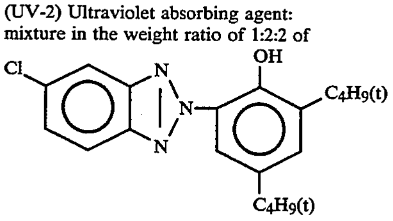

-continued

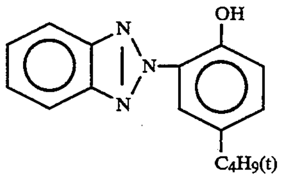

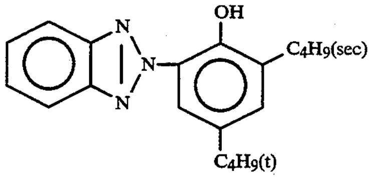

(Solv-1)

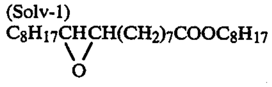

(Solv-2) Solvent

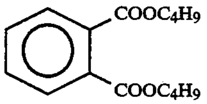

(Solv-3) Solvent

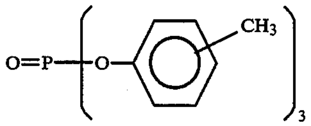

(Solv-4) Solvent

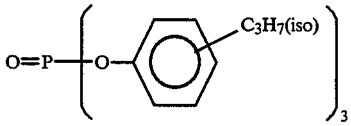

(Solv-5) Solvent

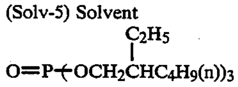

(Solv-6) Solvent

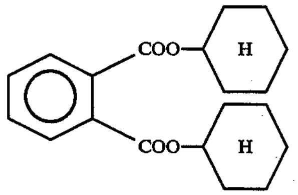

(Solv-7) Solvent

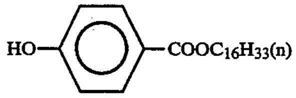

Preparation of samples 402 to 407

Samples 402 to 407 were prepared in the same manner as for sample 401 except that cyan coupler ExC of sample 401 was replaced with an equimolar amount of each of the cyan couplers shown in Table 20 below.

Each of samples 401 to 407 was exposed according to the method described in Example 1 (exposure was carried out with red light). After the completion of the exposure, sample 401 was continuously processed (running test) in the subsequent processing step (III) by using a paper processor until the amount of replenisher supplied became double the capacity of the tank for color development.

After the completion of the running test, samples 401 to 407 were processed for evaluation. Then, color generation and image stability were evaluated in the same manner as in Example 1. The results are shown in Table 20.

TABLE 17

| Step | Temperature | Time | Replenishment rate* | Tank capacity |
|---|---|---|---|---|
| Color development | 35° C. | 45" | 161 ml | 17 lit. |
| Bleach-fix | 30–35° C. | 45" | 215 ml | 17 lit. |
| Rinsing | 30° C. | 90" | 350 ml | 10 lit. |
| Drying | 70–80° C. | 60" | | |

*Replenishment rate: the amount of replenisher per $m^2$ of the photosensitive material.

The composition of each processing solution was as follows:

TABLE 18

| Color Developing Solution | Tank solution | Replenisher |
|---|---|---|
| Water | 800 ml | 800 ml |
| Ethylenediamine-N,N,N',N'-tetramethylenephosphonic acid | 1.5 g | 2.0 g |
| Potassium bromide | 0.015 g | |
| Triethanolamine | 8.0 g | 12.0 g |
| Sodium chloride | 1.4 g | |
| Potassium carbonate | 25 g | 25 g |
| N-ethyl-N-(β-methanesulfon amidoethyl)-3-methyl-4-aminoaniline sulfate | 5.0 g | 7.0 g |
| N,N-bis(carboxymethyl)hydrazine | 4.0 g | 5.0 g |
| N,N-di(sulfoethyl)hydroxyamine 1Na | 4.0 g | 5.0 g |
| Fluorescent brightening agent (WHITEX 4B, manufactured by Sumitomo Chemical Co.r Ltd.) | 1.0 g | 2.0 g |
| Water to make | 1000 ml | 1000 ml |
| pH (25° C.) | 10.05 | 10.05 |

TABLE 19

| Bleach-Fix Bath (replenisher: the same as tank solution) | |
|---|---|
| Water | 400 ml |
| Ammonium thiosulfate (700 g/lit.) | 100 ml |
| Sodium sulfite | 17 g |
| Ammonium (ethylenediaminetetra-acetato) iron (III) | 55 g |
| Disodium ethylenediaminetetraacetate | 5 g |
| Ammonium bromide | 40 g |
| Water to make | 1000 ml |
| pH (25° C.) | 6.0 |
| Rinsing Bath (replenisher: the same as tank solution) | |
| Ion-exchanged water (calcium and magnesium ions were reduced to not higher than 3 ppm, respectively). | |

TABLE 20

| Sample No. | Cyan coupler in 5th layer | Color generation* | Image stability | Remarks |
|---|---|---|---|---|
| 401 | ExC | 0.6 | 0.68 | Comp. Example |
| 402 | coupler (III)-1 | 1.0 | 0.98 | Invention |
| 403 | coupler (III)-6 | 0.9 | 0.99 | " |
| 404 | coupler (III)-8 | 1.0 | 0.97 | " |
| 405 | coupler (II)-5 | 1.2 | 0.99 | " |
| 406 | coupler (II)-9 | 1.2 | 0.99 | " |
| 407 | coupler (II)-12 | 1.1 | 0.99 | " |

*Expressed in values relative to the color generation of sample 402 as a standard (1.0).

It will be understood from Table 20 that even if a color developer with benzyl alcohol removed therefrom is used, the color print papers employing the couplers of the present invention are superior in both color generation and image stability.

Processing (VI) was carried out in the same way as the processing step (III) except that the pH of the bleach-fix bath in the processing step (III) was adjusted to 5.0. The difference between the maximum density value of each sample and the maximum density value thereof in the processing where the pH of the bleach-fix bath was 6.0 was obtained and used as a measure of leuco dye reciprocity characteristics. The results are shown in Table 21.

TABLE 21

| Sample No. | ΔDmax(Dmax(pH 5.0) − Dmax (pH 6.0)) | Remarks |
|---|---|---|
| 401 | −0.32 | Comp. Example |
| 402 | ±0.0 | Invention |
| 403 | ±0.0 | Invention |
| 404 | ±0.0 | Invention |
| 405 | ±0.0 | Invention |
| 406 | ±0.0 | Invention |
| 407 | ±0.0 | Invention |

It will be understood from the above results that the photosensitive materials employing the couplers of the present invention exhibit superior leuco dye reciprocity characteristics even when a processing solution having bleaching power having declined in oxidizing power is used.

Substantially the same results were obtained with regard to (IV)-2, (V)-2, (VI)-2, (VII)-2, (IX)-2, (X)-2, (XI)-2, (XII)-2, (XIII)-2, (XIX)-2, (XV)-2, (XVI)-2, (XVII)-2, (XVIII)-2 and (XIX)-2.

EXAMPLE 5

A sample 501 having the same arrangement as that of the photosensitive material shown as sample 601 in Example 6 described in Japanese Patent Application Laid-Open (KOKAI) No. 2-139544 (1990) was prepared. Next, samples 502 to 507 were prepared in the same way except that cyan couplers C-1, C-2 and C-3 in the 4th, 5th and 6th layers of sample 501 were replaced with the couplers shown in Table 22 below, and evaluation was made in the same way as in Example 1.

TABLE 22

| Sample No. | Coupler in 4th, 5th & 6th layers | Color generation* | Image stability | Remarks |
|---|---|---|---|---|
| 501 | C-1,C-2,C-3,C-9 | 0.40 | 0.55 | Comp. Example |
| 502 | coupler (III)-1 | 1.00 | 0.97 | Invention |
| 503 | coupler (III)-3 | 0.98 | 0.98 | " |
| 504 | coupler (III)-6 | 1.00 | 0.96 | " |
| 505 | coupler (II)-1 | 1.20 | 0.99 | " |
| 506 | coupler (II)-6 | 0.98 | 0.94 | " |
| 507 | coupler (II)-8 | 1.20 | 0.99 | " |

*Expressed in values relative to the color generation of sample 502 as a standard (1.0).

Further, samples were prepared in such a manner that C-6 in the 16th and 17th layers in the above-described samples was replaced with an equimolar amount of C-10, and C-4 and C-7 in the 9th to 11th layers were replaced with C-8 so that the total amount was 80 mol %, and evaluation was made in the same way as the above. In this case also, substantially the same results were obtained.

C-8

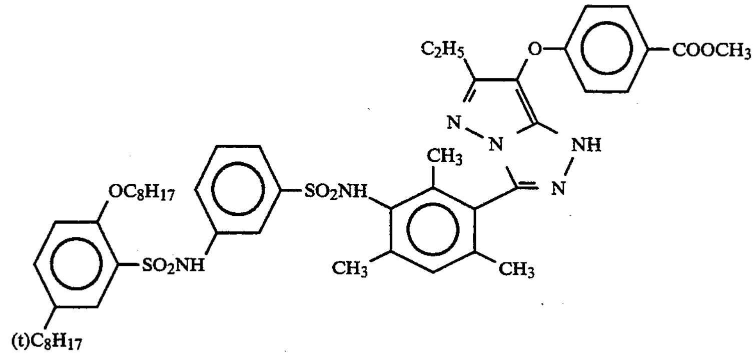

C-10

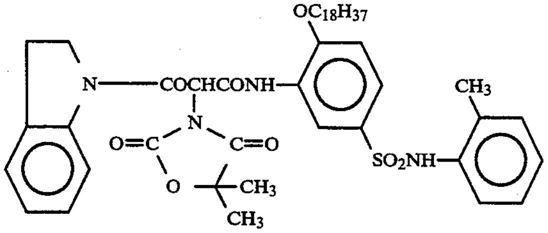

Thus, it will be understood that the color reversal photosensitive materials using the cyan couplers of the present invention are also superior in both color generation and dye image stability.

Substantially the same results were obtained with regard to (IV)-1, (V)-1, (VI)-1, (VII)-1, (IX)-1, (X)-1, (XI)-1, (XII)-1, (XIII)-1, (XIX)-1, (XV)-1, (XVI)-1, (XVII)-1, (XVIII)-1 and (XIX)-1.

EXAMPLE 6

FIG. 1 shows an absorption spectrum in ethyl acetate of a dye produced by an oxidative coupling reaction of compound of formula (XX), (e.g., Compound 1), and 2-methyl-4-(N-ethyl-N-methanesulfonylethylamino) aniline: $\lambda max = 668$ nm and $\epsilon = 3.9 \times 10^4$. The dye formed from coupler of formula (XX) (e.g., Compound 1) of the present invention has a molar extinction coefficient which is 1.5 or more times that of the conventional coupler (A-1) described below. The reactivity in the oxidative coupling was also extremely high.

EXAMPLE 7

Preparation of Sample 701

A sample 701 with a layer structure described below was formed on a cellulose triacetate film base. The first layer coating solution was prepared as follows:

Preparation of 1st Layer Coating Solution

To 10.0 cc of ethyl acetate were added 0.61 g of cyan coupler (A-1) and 1.18 g of dibutyl phthalate and they were completely dissolved therein. The resulting coupler solution in ethyl acetate was added to 42 g of aqueous solution of 10% gelatin (containing 7 g of sodium dodecylbenzenesulfonate per liter) and emulsified in a homogenizer. After the emulsification, distilled water was added to the resulting emulsion dispersion so that the total weight was 100 g. Then, 100 g of emulsion dispersion and 8.2 g of high silver chloride emulsion (silver bromide content: 0.5 mol %) were mixed thoroughly to prepare a 1st layer coating solution with a composition shown below.

As a gelatin hardening agent, 1-oxy-3,5-dichloro-s-triazine sodium salt was employed.

Layer Structure

The layer structure of each layer will be shown below.

Support

Cellulose triacetate film.

| | |
|---|---|
| 1st Layer (Emulsion Layer): | |
| Light silver chloride emulsion | 0.23 g/m$^2$ as Ag |
| Gelatin | 2.20 g/m$^2$ |
| Cyan coupler (A-1) | 0.29 g/m$^2$ |
| Dibutyl phthalate | 0.58 g/m$^2$ |
| 2nd Layer (Protecive Layer): | |
| Gelatin | 1.40 g/m$^2$ |

Preparation of Samples 702 to 706

Samples 702 to 706 were prepared in the same manner as for sample 701 except that cyan coupler (A-1) was replaced with an equimolar amount of each of the couplers shown in Table 23 below.

Cyan Coupler (A-1):

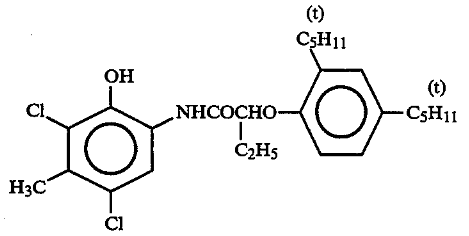

Each of samples 701 to 706was wedgewise exposed to white light and subjected to color development processing according to the following processing schedule.

Evaluation of Color Developability

After development processing, the density of each sample was measured to evaluate the color developability by the maximum density.

Evaluation of Image Stability

Each processed sample was allowed to stand at 75° C. for days to perform a fading test. The cyan density ($D_R$) after the fading test at a portion whose cyan density before the test was 0.8 was measured, and a rate of residual dye was obtained on the basis of the cyan density ($D_R$) according to the following equation, thereby evaluating the image stability of each sample. The results are shown in Table 23.

Rate of residual dye$=\{(D_R)/0.8\}\times 100$

| Processing Schedule | | |
|---|---|---|
| Step | Temperature | Time |
| Color development | 38° C. | 45" |
| Bleach-fix | 35° C. | 45" |
| Rinsing ① | 35° C. | 30" |
| Rinsing ② | 35° C. | 30" |
| Rinsing ③ | 35° C. | 30" |
| Drying | 80° C. | 60" |

(Rinsing was effected in a 3-tank counter-flow system: from tank ③ toward tank ①)

Each processing solution had the following composition.

| | | |
|---|---|---|
| Color Developing Solution: | | |
| Water | 800 | ml |
| Ethylenediamine-N,N,N,N-tetramethylene-phosphonic acid | 3.0 | g |
| Triethanolamine | 8.0 | g |
| Potassium chloride | 3.1 | g |
| Potassium bromide | 0.015 | g |
| Potassium carbonate | 25.0 | g |
| Hydrazinodiacetic acid | 5.0 | g |
| N-ethyl-N-(β-methanesulfonamidoethyl)-3-methyl-4-aminoaniline sulfate | 5.0 | g |
| Fluorescent brightening agent (WHITEX-4 manufactured by Sumitomo Chemical Co., Ltd.) | 2.0 | g |
| Water to make | 1000 | ml |
| pH (adjusted with potassium hydroxide) | 10.05 | |
| Bleach-Fix Bath: | | |
| Water | 400 | ml |
| Ammonium thiosulfate (700 g/l) | 100 | ml |
| Ammonium sulfite | 45 | g |
| Ammonium (ethylenediaminetetra-acetato)iron(III) | 55 | g |
| Ethylenediaminetetraacetic acid | 3 | g |
| Ammonium bromide | 30 | g |
| Nitric acid (67%) | 27 | g |
| Water to make | 1000 | ml |
| pH | 5.7 | |

Rinsing Bath

Ion-exchanged water (calcium and magnesium ions were reduced to not higher than 3 ppm, respectively).

TABLE 23

| Sample No. | Coupler No. | Maximum density difference* | Stability to heat | Remarks |
|---|---|---|---|---|
| 701 | A-1 | 1.00 | 72% | Comparison |
| 702 | (1) | 1.62 | 91% | Invention |
| 703 | (2) | 1.61 | 90% | " |
| 704 | (3) | 1.66 | 94% | " |
| 705 | (4) | 1.62 | 91% | " |
| 706 | (5) | 1.63 | 92% | " |

*Expressed in values relative to the maximum density of sample 701 as a standard (1.00).

It will be clear from Table 23 that the samples according to the present invention have high maximum density values and superior stability to heat.

Accordingly, it will be understood that the couplers of the present invention, when employed in a multilayer photosensitive material, enable a reduction in the amount of coupler used to attain the same level of density as that in the prior art and hence permit a reduction in the overall layer thickness, thus allowing an improvement in the sharpness.

EXAMPLE 8

Samples were prepared in the same manner as in Example 7 except that a silver iodobromide (6.5 mol of silver iodide) emulsion was employed in place of the high silver chloride emulsion. The samples thus prepared were subjected to color development processing according to the following processing schedule, and evaluation was made in the same manner as in Example 6.

Samples in Example 8, corresponding to samples 701 to 706 in Example 7, were denoted by 801 to 806, respectively.

The results of the evaluation revealed that the couplers of the present invention had high color densities and superior stability to heat.

Accordingly, the couplers of the present invention enable a reduction in the amount of coupler used to attain the same level of density as that in the prior art and hence permit a reduction in the overall layer thickness.

| Processing Schedule | | |
|---|---|---|
| Step | Time | Temperature |
| Color development | 3'15" | 38° C. |
| Bleach | 1'00" | 38° C. |
| Bleach-fix | 3'15" | 35° C. |
| Washing ① | 40" | 35° C. |
| Washing ② | 1'00" | 35° C. |
| Stabilization | 40" | 38° C. |
| Drying | 1'15" | 55° C. |

Each processing solution had the following composition.

| | | |
|---|---|---|
| Color Developing Solution: | | |
| Diethylenetriaminepentaacetic acid | 1.0 | g |
| 1-hydroxyethylidene-1,1-diphosphonic acid | 3.0 | g |
| Sodium sulfite | 4.0 | g |
| Potassium carbonate | 30.0 | g |
| Potassium bromide | 1.4 | g |
| Potassium iodide | 1.5 | mg |
| Hydroxylamine sulfate | 2.4 | g |
| 4-[N-ethyl-N-β-hydroxyethylamino-2-methylaniline sulfate | 4.5 | g |
| Water to make | 1.0 | l |
| pH | 10.05 | |
| Bleaching Bath: | | |
| Ammonium (ethylenediaminetetra-aceto)iron(II) dihydrate | 120.0 | g |
| Disodium ethylenediaminetetraacetate | 10.0 | g |
| Ammonium bromide | 100.0 | g |

-continued

| | | |
|---|---|---|
| Ammonium nitrate | 10.0 | g |
| Bleaching accelerator | 0.005 | mol |
| 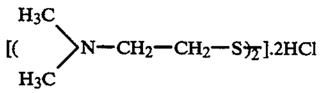 | | |
| Aqueous ammonia (27%) | 15.0 | ml |
| Water to make | 1.0 | l |
| pH | 6.3 | |
| Bleach-Fix Bath: | | |
| Ammonium (ethylenediaminetetra-aceto)iron(II) dihydrate | 50.0 | g |
| Disodium ethylenediaminetetraacetate | 5.0 | g |
| Sodium sulfite | 12.0 | g |
| Aqueous ammonium thiosulfate (700 g/l) | 240.0 | ml |
| Aquous ammonia (27%) | 6.0 | ml |
| Water to make | 1.0 | l |
| pH | 7.2 | |

Washing Water

Tap water was passed through a mixed bed column packed with an H-type strongly acidic cation exchange resin Amberlite IR-120B (manufactured by Rohm & Haas Co.) and an OH-type strongly basic anion exchange resin Amberlite IRA-400 (manufactured by Rohm & Haas Co.) to reduce calcium and magnesium ions to 3 mg/l or less, respectively. To the thus treated water were added 20 mg/l of sodium isocyanurate dichloride and 0.15 g/l of sodium sulfate. The resulting washing water had a pH between 6.5 and 7.5.

| Stabilizing Bath: | | |
|---|---|---|
| Formalin (37%) | 2.0 | ml |
| Polyoxyethylene-p-monononyl phenyl ether (average degree of polymerization: 10) | 0.3 | g |
| Disodium ethylenediaminetetraacetate | 0.05 | g |
| Water to make | 1.0 | l |
| pH | 5.0-8.0 | |

EXAMPLE 9

Testing and evaluation were carried out in the same manner as in Example 8 except for the processing schedule.

The results are shown in Table 24 below.

| | Processing Schedule | |
|---|---|---|
| Step | Time (min) | Temperature (°C.) |
| 1st development | 6 | 38 |
| Washing | 2 | " |
| Reversing | 2 | " |
| Color Development | 6 | " |
| Compensation | 2 | " |
| Bleach | 6 | " |
| Fixing | 4 | " |
| Washing | 4 | " |
| Stabilization | 1 | room temperature |
| Drying | 2 | 50 |

Each processing solution had the following composition.

| | | |
|---|---|---|
| 1st Developing Solution: | | |
| Water | 700 | ml |
| Pentasodium nitrilo-N,N,N-trimethylenephosphonate | 2 | g |
| Sodium sulfite | 20 | g |

-continued

| | | |
|---|---|---|
| Hydroquinone monosulfonate | 30 | g |
| Sodium carbonate (monohydrate) | 30 | g |
| 1-phenyl-4-methyl-4-hydroxymethyl-3-pyrazolidone | 2 | g |
| Potassium bromide | 2.5 | g |
| Potassium thiocyanate | 1.2 | g |
| Potassium iodide (0.1% solution) | 2 | ml |
| Water to make | 1000 | ml |
| pH | 9.60 | |
| Reversing Bath: | | |
| Water | 700 | ml |
| Pentasodium nitrilo-N,N,N-trimethylenephosphonate | 3 | g |
| Stannous chloride dihydrate | 1 | g |
| p-aminophenol | 0.1 | g |
| Sodium hydroxide | 8 | g |
| Glacial acetic acid | 15 | ml |
| Water to make | 1000 | ml |
| pH | 6.00 | |
| Color Developing Solution: | | |
| Water | 700 | ml |
| Pentasodium nitrilo-NrN,N-trimethylenephosphonate | 3 | g |
| Sodium sulfite | 7 | g |
| Sodium tertiary phosphate dodecahydrate | 36 | g |
| Potassium bromide | 1 | g |
| Postassim iodide (0.1% solution) | 90 | ml |
| Sodium hydroxide | 3 | g |
| Citrazinic acid | 1.5 | g |
| N-ethyl-N-(β-methanesulfonamidoethyl)-3-methyl-4-aminoaniline sulfate | 11 | g |
| 3,6-dithiaoctane-1,8-diol | 1 | g |
| Water to make | 1000 | ml |
| pH | 11.80 | |
| Compensating Solution: | | |
| Water | 700 | ml |
| Sodium sulfite | 12 | g |
| Sodium ethylenediaminetetraacetate dihydrate | 8 | g |
| Thioglycerin | 0.4 | ml |
| Glacial acetic acid | 3 | ml |
| Water to make | 1000 | ml |
| pH | 6.60 | |
| Bleaching Bath: | | |
| Water | 800 | ml |
| Sodimum ethylenediaminetetraacetate dihydrate | 2 | g |
| Ammonium (ethylenediaminetetraacetato)-iron(III) dihydrate | 120 | g |
| Potassium bromide | 100 | g |
| Water to make | 1000 | ml |
| pH | 5.70 | |
| Fixing Bath: | | |
| Water | 800 | ml |
| Sodium thiosulfate | 80.0 | g |
| Sodium sulfite | 5.0 | g |
| Sodium bisulfite | 5.0 | g |
| Water to make | 1000 | ml |
| pH | 6.60 | |
| Stabilizing Bath: | | |
| Water | 800 | ml |
| Formalin (37 wt%) | 5.0 | ml |
| Fuji Dry Well (surface active agent manufactured by Fuji Photo Film Co., Ltd.) | 5.0 | ml |
| Water to make | 1000 | ml |
| pH | 7.0 | |

TABLE 24

| Sample No. | Coupler No. | Maximum density difference* | Stability to heat | Remarks |
|---|---|---|---|---|
| 801 | A-1 | 1.00 | 75% | Comparison |
| 802 | (1) | 1.64 | 92% | Invention |
| 803 | (2) | 1.63 | 91% | " |
| 804 | (3) | 1.68 | 95% | " |
| 805 | (4) | 1.63 | 92% | " |

TABLE 24-continued

| Sample No. | Coupler No. | Maximum density difference* | Stability to heat | Remarks |
|---|---|---|---|---|
| 806 | (5) | 1.64 | 93% | " |

*Expressed in values relative to the maximum density of sample 801 as a standard (1.00).

It will be clear from Table 24 that the samples according to the present invention have high maximum density values and superior stability to heat.

EXAMPLE 10

As a silver halide color photosensitive material, sample No. 214 (multilayer color print paper) described in Example 2 in European Patent No. EPO,355,660A2 (corresponding to Japanese Patent Application Laid-Open (KOKAI) No. 02-139544 (1990) and U.S. Ser. No. 07/393,747) was used.

However, as a bisphenol compound, III-23 described in the above-described publication was replaced with III-10 of the above described publication.

The yellow coupler (ExY), dye image stabilizing agent (Cpd-8), solvent (Solv-6) and oxonol dye were changed to the following compounds, respectively. In addition, as a preservative (antiseptic and antifungal agent), the following compound was used, and the 5th layer cyan coupler was replaced with an equimolar amount of each of couplers (1), (2), (3), (4) and (5).

(Exy) Yellow Coupler

A mixture in the molar ratio of 1:1 of

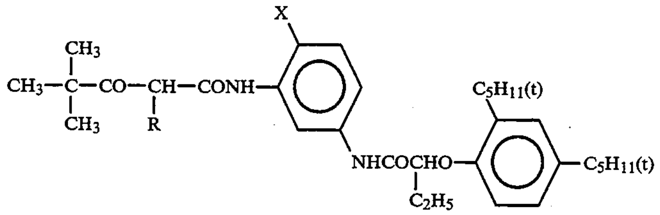

R = 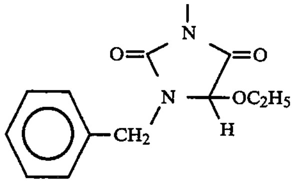 X = Cl and

R = 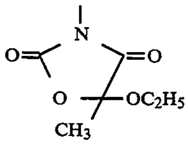 X = $OCH_3$ (Cpd-8) Dye Image Stabilizing Agent

A mixture in the molar ratio of 1:1 of

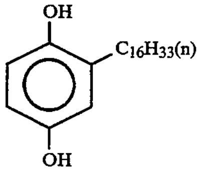 and 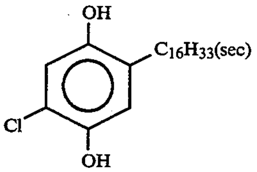

(Cpd-10) Preservative:

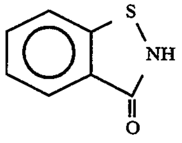

(25.0 mg/m²)

(Cpd-11) Preservative:

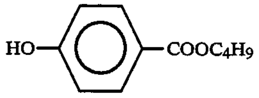

(50.0 mg/m²)

(Solv-6) Solvent

A mixture in the weight ratio of 9:1 of

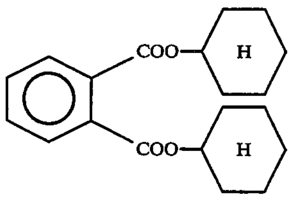

and

-continued

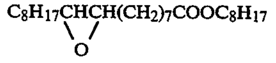

(Oxonol dye)

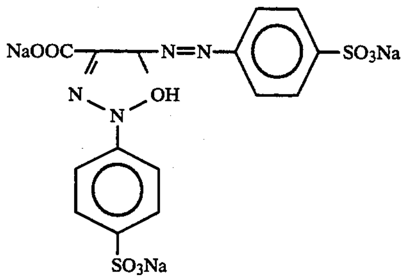

(10 mg/m²)

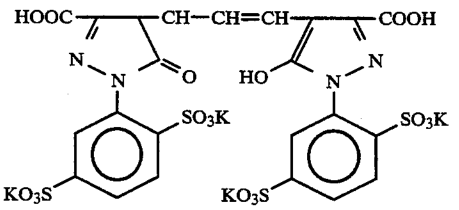

(10 mg/m²)

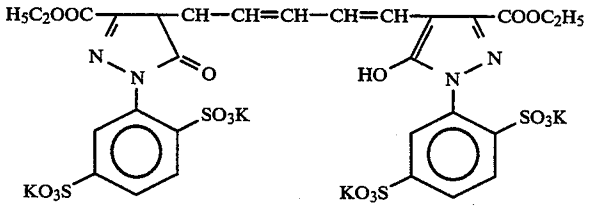

(40 mg/m²)

and

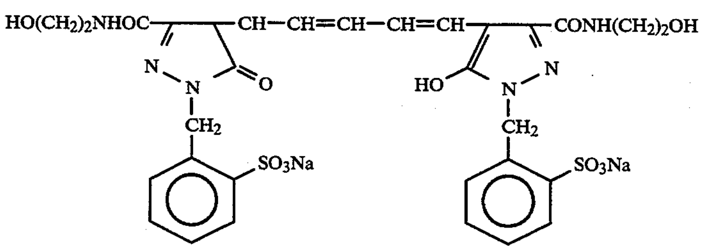

(20 mg/m²)

The color photosensitive materials were subjected to color development processing in the-same manner as in Example 7.

The results revealed that the color photosensitive materials of the present invention had excellent color developability (particularly in green) and superior stability to heat.

What is claimed is:

1. A silver halide color photosensitive material comprising a support having thereon at least one hydrophilic colloidal layer containing at least one coupler represented by formula (I):

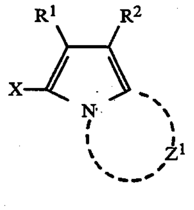

(I)

wherein $R^1$ and $R^2$ each represents an electron withdrawing group having a Hammett's $\sigma p$ value of 0.35 or higher; X represents hydrogen atom or a group releasable on a coupling reaction with an oxidation product of a color developing agent; $Z^1$ represents a nonmetallic atom group necessary for forming a nitrogen-containing, six-membered, heterocyclic ring which has at least one dissociative group: $Z^1$ cannot be —C(=O)—N(-R)—C(=O)—NH—; and R represents a substituent.

2. A silver halide color photosensitive material according to claim 1, wherein the substituents represented by $R^1$ and $R^2$ are selected from the group consisting of an aryl group, an alkyl group, a cyano group, an acyl group, a carbamoyl group, an alkoxycarbonyl group, an aryloxycarbonyl group, formylamino group, an acylamino group, an alkoxycarbonylamino group, an aryloxycarbonylamino group, a sulfonamido group, an ureido group, a sulfamoylamino group, an alkylamino group, an arylamino group, a sulfamoyl group, and a sulfonyl group.

3. A silver halide color photosensitive material according to claim 1, wherein X is selected from the group consisting of a hydrogen atom, a halogen atom, an alkoxy group, an aryloxy group, an alkyl, aryl or heteryl acyloxy group, an alkyl, aryl or heteryl sulfonyloxy group, an acylamino group, a sulfonamido group, an alkoxycarbonyloxy group, an aryloxycarbonyloxy group, an alkylthio group, an arylthio group, a heterocyclic thio group, a carbamoylamino group, a 5- or 6-membered nitrogen-containing heterocyclic group, an imido group, an aryl azo group, an alkyl, aryl or heteryl sulfinyl group and an alkyl, aryl or heteryl sulfonyl group.

4. A silver halide color photosensitive material according to claim 1, wherein the nitrogen-containing, six-membered, heterocyclic ring is formed by four divalent groups selected from the group consisting of —NH—, —N(R)—, —N=, —CH(R)—, —CH=, —C(R)=, —CO—, —S—, —SO—, and $—SO_2—$ (wherein R represents a substituent), and the dissociative group is selected from among —NH— and —CH(-R)—.

5. A silver halide color photosensitive material according to claim 1, wherein $R^1$ represents an electron withdrawing group having a Hammett's $\sigma p$ value of 0.60 or higher.

6. A silver halide color photosensitive material according to claim 1, wherein the electron withdrawing group having a Hammett's $\sigma p$ value of 0.35 or higher is selected from the group consisting of a cyano group, a nitro group, a carboxyl group, a perfluoroalkyl group, an acyl group, a formyl group, a sulfonyl group, a sulfinyl group, a carbamoyl group, an alkoxycarbonyl group, an aryloxycarbonyl group, a heterocyclic group, an alkylsulfonyloxy group, a phosphoryl group, a sulfamoyl group, a pentachlorophenyl group, a pentafluorophenyl group and a sulfonyl group substituted phenyl group.

7. A silver halide color photosensitive material according to claim 1, wherein the coupler represented by formula (I) is contained in an amount of from $1\times10^{-3}$ to 1 mol per mol of silver halide.

8. A silver halide color photosensitive material according to claim 1, wherein the coupler represented by formula (I) is a cyan coupler.

9. A silver halide color photosensitive material according to claim 1, wherein the hydrophilic colloidal layer is a red-sensitive silver halide emulsion layer.

10. A silver halide color photosensitive material according to claim 1, wherein the coupler of formula (I) is a coupler represented by one of formula (II) to (VII) and (IX) to (XIX):

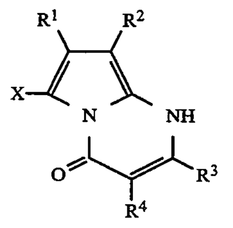
(II)

-continued

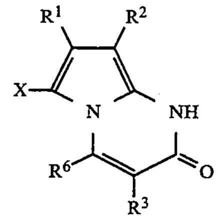
(III)

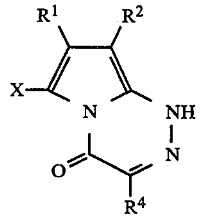
(IV)

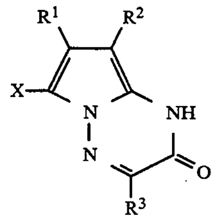
(V)

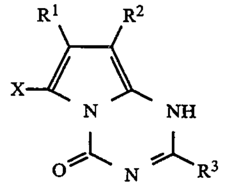
(VI)

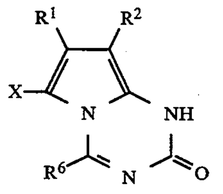
(VII)

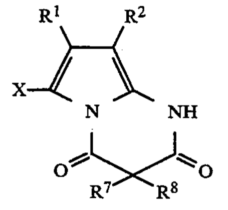
(IX)

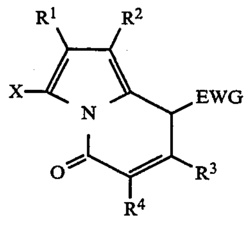
(X)

-continued

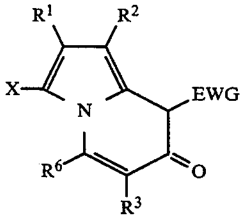

(XI)

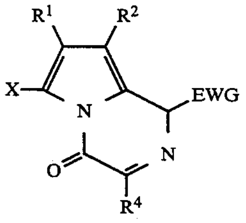

(XII)

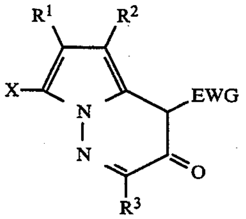

(XIII)

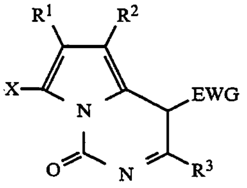

(XIV)

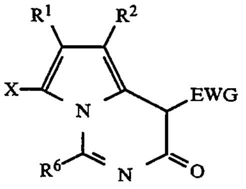

(XV)

-continued

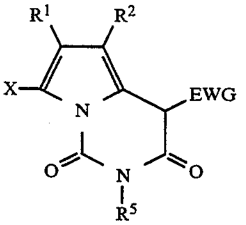

(XVI)

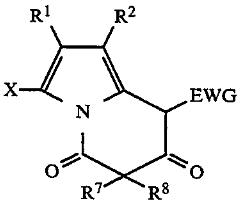

(XVII)

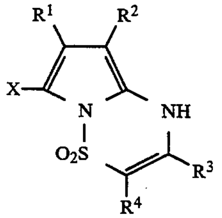

(XVIII)

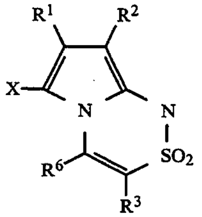

(XIX)

wherein in the above formulae (II) to (VII) and (IX) to (XIX), $R^1$ and $R^2$ have the same meaning as $R^1$ and $R^2$ in formula (I), $R^3$, $R^5$, $R^6$, $R^7$ and $R^8$ each represents a hydrogen atom or a substituent, $R^4$ represents a substituent, and EWG represents an electron withdrawing group having a Hammett's $\sigma p$ value of 0.35 or higher.

* * * * *